(12) United States Patent
Bolton et al.

(10) Patent No.: US 6,833,134 B2
(45) Date of Patent: Dec. 21, 2004

(54) **IMMUNIZATION OF DAIRY CATTLE WITH GAPC PROTEIN AGAINST *STREPTOCOCCUS* INFECTION**

(75) Inventors: Alexandra J. Bolton, Calgary (CA); Jose Perez-Casal, Saskatoon (CA); Michael Fontaine, West Lothian (GB); Andrew A. Potter, Saskatoon (CA)

(73) Assignee: University of Saskacthewan (CA)

( * ) Notice: Subject to any disclaimer, the term of this patent is extended or adjusted under 35 U.S.C. 154(b) by 113 days.

(21) Appl. No.: 10/134,297

(22) Filed: Apr. 26, 2002

(65) Prior Publication Data

US 2003/0165524 A1 Sep. 4, 2003

Related U.S. Application Data

(63) Continuation-in-part of application No. 09/878,781, filed on Jun. 11, 2001.
(60) Provisional application No. 60/211,022, filed on Jun. 12, 2000.

(51) Int. Cl.[7] .................. A61K 39/09; A61K 30/02; A61K 39/38; A61K 38/00; C07K 1/00
(52) U.S. Cl. .................. 424/244.1; 424/234.1; 424/190.1; 424/184.1; 530/350; 530/300; 530/825; 514/2
(58) Field of Search .................. 530/350, 300, 530/825; 424/234.1, 244.1, 190.1; 514/2

(56) References Cited

U.S. PATENT DOCUMENTS

| | | | |
|---|---|---|---|
| 4,954,618 A | 9/1990 | Fahnestock | 530/387 |
| 4,977,082 A | 12/1990 | Boyle et al. | 435/71.1 |
| 5,108,894 A | 4/1992 | Bjorck et al. | 435/6 |
| 5,237,050 A | 8/1993 | Boyle et al. | 530/350 |
| 5,328,996 A | 7/1994 | Boyle et al. | 536/23.1 |
| 5,721,339 A | 2/1998 | Boyle et al. | 530/350 |
| 5,863,543 A | 1/1999 | Jiang et al. | 424/244.1 |
| 2003/0072765 A1 | 4/2003 | Potter et al. | |

FOREIGN PATENT DOCUMENTS

| | | |
|---|---|---|
| EP | 0 887 410 | 12/1998 |
| WO | WO 96/40928 | 12/1996 |
| WO | WO 96/41879 | 12/1996 |
| WO | WO 98/18930 | 5/1998 |
| WO | WO 99/42588 | 8/1999 |
| WO | WO 00/39299 | 7/2000 |
| WO | WO 01/96381 | 12/2001 |

OTHER PUBLICATIONS

Fontaine et al., "Immunization of Dairy Cattle with Recombinant *Streptococcus Uberis* GAPC or a Chimeric Camp Antigen Confers Protection Against Heterologous Bacterial Challenge," Vaccine 20(17–18):2278–2286 (2002).
Leigh, Immunization of Dairy Cattle with Recombinant *Streptococcus Uberis* GAPC or a Chimeric Camp Antigen Confers Protection Against Heterologous Bacterial Challenge, M.C. Fontaine et al., Vaccine 20:2278–2286, Vaccine, Butterworth Scientific. Guilford, GB, 20:25–26 (2002).
Baird et al., "Epitopes of Group A Streptoocal M Protein Shared With Antigens of Articular Cartilage and Synovium," The Journal of Immunology 146(9):3132–3137 (1991).
Bisno, Alan. L., "Group A Streptococcal Infections and Acute Rheumatic Fever," New Eng J. Med. 325:783–793 (1991).
Bronze et al., "Epitopes of Streptococcal M Proteins that Evoke Antibodies That Cross–React with Human Brain," The Journal of Immunology 151(5):2820–2828 (1993).
Cunningham et al., "Study of Heart–Reactive Antibody in Antisera and Hybridoma Culture Fluids Against Group A Strepatococci," Infection and Immunity 42(2):531–538 (1983).
Dale, J. L., "Multivalent Group A Streptococcal Vaccine Designed to Optimize the Immunogenicity of Six Tandem M Protein Fragments," Vaccine 17(2):193–200 (1999).
Dale, J. L. and Beachy, G. H., "Multiple, Heart–Cross Reactive Epitopes of Streptococcal M Proteins," J. Exp. Med. 161:113–122 (1995).
Dale, J. L. and Beachy, G. H., "Protective Antigenic Determinant of Streptococcal M Protein Shared With Sarcolemmal Membrane Protein of Human Heart," J. Exp. Med. 156:1165–1176 (1985).
Finch et al., "Further Studies on the Efficacy of a Live Vaccine Against Mastitis Caused by *Streptococcus Uberis*," Vaccine 15(10):1138–1143 (1997).
Froude et al., "Cross–Reactivity Between Streptococcus and Human Tissue: A Model of Molecular Mimicry and Autoimmunity," Microbiology and Immunology 145:5–26 (1989).
Gase et al., "Cloning Sequencing and Functional Overexpression of the *Streptococcus Equisimilis* H46A gapC Gene Encoding a Glyceraldehyde–3–Phosphate Dehydrogenase that also Functions as a Plasmin(ogen)–Binding Protein. Purification and Biochemical Characterization of the Protein," European Journal of Biochemistry 239(1):42–51 (1996).
Kehoe, Michael A., "Group A Streptococcal Antigens and Vaccine Potential," Vaccine 9:797–806 (1991).
Lancefield, Rebecca C., "Current Knowledge of Type–Specific M Antigens of Group A Streptococci," J. of Immunology 89:307–313 (1962).
Langone, John J., "Protein A of *Staphylococcus aureus* and Related Immunoglobulin Receptors Produced by Streptococcio and Pneumonococci," Advances in Immunology 32:167 (1982).
Liljeqvist et al., "Surface Display of Functional Fibronectin–Binding Domains on *Staphylococcus carnosus*," FEBS Letters 446:299–304 (1999).
Stollerman, G. H., "Rheumatogenic Streptococci and Autouimmunity," Clin. Immunol. Immunopathology, 61:131–142 (1991).

Primary Examiner—S. Devi
(74) Attorney, Agent, or Firm—Robins & Pasternak LLP

(57) ABSTRACT

The GapC plasmin binding protein genes of *Streptococcus dysgalactiae* (S. dysgalactiae), *Streptococcus agalactiae* (S. agalactiae), *Streptococcus uberis* (S. uberis), *Streptococcus parauberis* (S. parauberis), and *Streptococcus iniae* (S. iniae) are described, as well as the recombinant production of the GapC proteins therefrom. Also described is the use of the GapC proteins from those species in vaccine compositions to prevent or treat bacterial infections in general, and mastitis in particular.

5 Claims, 35 Drawing Sheets

```
atg gta gtt aaa gtt ggt att aac ggt ttc ggt cgt atc gga cgt ctt      48
Met Val Val Lys Val Gly Ile Asn Gly Phe Gly Arg Ile Gly Arg Leu
 1            5                  10                 15 gca ttc cgt cgt att caa aat gtt gaa ggt gtt gaa gta act cgt atc      96
Ala Phe Arg Arg Ile Gln Asn Val Glu Gly Val Glu Val Thr Arg Ile
             20                  25                 30 aac gac ctt aca gat cca aac atg ctt gca cac ttg ttg aaa tac gat     144
Asn Asp Leu Thr Asp Pro Asn Met Leu Ala His Leu Leu Lys Tyr Asp
         35                  40                 45 aca act caa gga cgt ttt gac gga act gtt gaa gtt aaa gaa ggt gga     192
Thr Thr Gln Gly Arg Phe Asp Gly Thr Val Glu Val Lys Glu Gly Gly
     50                  55                 60 ttt gaa gta aac gga aac ttc atc aaa gtt tct gct gaa cgt gat cca     240
Phe Glu Val Asn Gly Asn Phe Ile Lys Val Ser Ala Glu Arg Asp Pro
 65                  70                 75                 80 gaa aac atc gac tgg gca act gac ggt gtt gaa atc gtt ctg gaa gca     288
Glu Asn Ile Asp Trp Ala Thr Asp Gly Val Glu Ile Val Leu Glu Ala
             85                  90                 95 act ggt ttc ttt gct aaa aaa gaa gct gct gaa aaa cac tta cat gct     336
Thr Gly Phe Phe Ala Lys Lys Glu Ala Ala Glu Lys His Leu His Ala
            100                 105                110 aac ggt gct aaa aaa gtt gtt atc aca gct cct ggt gga aac gac gtt     384
Asn Gly Ala Lys Lys Val Val Ile Thr Ala Pro Gly Gly Asn Asp Val
        115                 120                 125 aaa aca gtt gtt ttc aac act aac cac gac att ctt gac ggt act gaa     432
Lys Thr Val Val Phe Asn Thr Asn His Asp Ile Leu Asp Gly Thr Glu
    130                 135                 140 aca gtt atc tca ggt gct tca tgt act aca aac tgt tta gct cct atg     480
Thr Val Ile Ser Gly Ala Ser Cys Thr Thr Asn Cys Leu Ala Pro Met
145                 150                 155                 160 gct aaa gct ctt cac gat gca ttt ggt atc caa aaa ggt ctt atg act     528
Ala Lys Ala Leu His Asp Ala Phe Gly Ile Gln Lys Gly Leu Met Thr
                165                 170                 175 aca atc cac gct tat act ggt gac caa atg atc ctt gac gga cca cac     576
Thr Ile His Ala Tyr Thr Gly Asp Gln Met Ile Leu Asp Gly Pro His
            180                 185                 190 cgt ggt ggt gac ctt cgt cgt gct cgt gct ggt gct gca aac att gtt     624
Arg Gly Gly Asp Leu Arg Arg Ala Arg Ala Gly Ala Ala Asn Ile Val
        195                 200                 205
```

FIG. 1A

```
cct aac tca act ggt gct gct aaa gct atc ggt ctt gtt atc cca gaa    672
Pro Asn Ser Thr Gly Ala Ala Lys Ala Ile Gly Leu Val Ile Pro Glu
    210                 215                 220 ttg aat ggt aaa ctt gat ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gag ttg gtt gta act ctt gat aaa aac gtt tct gtt    768
Gly Ser Val Thr Glu Leu Val Val Thr Leu Asp Lys Asn Val Ser Val
                245                 250                 255 gac gaa atc aac gct gct atg aaa gct gct tca aac gac agt ttc ggt    816
Asp Glu Ile Asn Ala Ala Met Lys Ala Ala Ser Asn Asp Ser Phe Gly
            260                 265                 270 tac act gaa gat cca att gtt tct tca gat atc gta ggc gtg tca tac    864
Tyr Thr Glu Asp Pro Ile Val Ser Ser Asp Ile Val Gly Val Ser Tyr
        275                 280                 285 ggt tca ttg ttt gac gca act caa act aaa gtt atg gaa gtt gac gga    912
Gly Ser Leu Phe Asp Ala Thr Gln Thr Lys Val Met Glu Val Asp Gly
    290                 295                 300 tca caa ttg gtt aaa gtt gta tca tgg tat gac aat gaa atg tct tac    960
Ser Gln Leu Val Lys Val Val Ser Trp Tyr Asp Asn Glu Met Ser Tyr
305                 310                 315                 320 act gct caa ctt gtt cgt aca ctt gag tac ttt gca aaa atc gct aaa   1008
Thr Ala Gln Leu Val Arg Thr Leu Glu Tyr Phe Ala Lys Ile Ala Lys
                325                 330                 335 taa                                                                1011
```

FIG. 1B

```
atg gta gtt aaa gtt ggt att aac ggt ttc ggt cgt atc ggt cgt ctt      48
Met Val Val Lys Val Gly Ile Asn Gly Phe Gly Arg Ile Gly Arg Leu
 1               5                  10                  15 gca ttc cgt cgc atc caa aac gta gaa ggt gtt gaa gtt act cgt atc      96
Ala Phe Arg Arg Ile Gln Asn Val Glu Gly Val Glu Val Thr Arg Ile
                20                  25                  30 aac gac ctt aca gat cca aac atg ctt gca cac ttg ttg aaa tat gac     144
Asn Asp Leu Thr Asp Pro Asn Met Leu Ala His Leu Leu Lys Tyr Asp
                35                  40                  45 aca act caa ggt cgt ttc gac ggt act gtt gaa gtt aaa gaa ggt gga     192
Thr Thr Gln Gly Arg Phe Asp Gly Thr Val Glu Val Lys Glu Gly Gly
        50                  55                  60 ttc gaa gtt aac ggt caa ttt gtt aaa gtt tct gct gaa cgc gaa cca     240
Phe Glu Val Asn Gly Gln Phe Val Lys Val Ser Ala Glu Arg Glu Pro
 65                  70                  75                  80 gca aac att gac tgg gct act gat ggc gta gaa atc gtt ctt gaa gca     288
Ala Asn Ile Asp Trp Ala Thr Asp Gly Val Glu Ile Val Leu Glu Ala
                85                  90                  95 act ggt ttc ttt gca tca aaa gaa aaa gct gga caa cac atc cat gaa     336
Thr Gly Phe Phe Ala Ser Lys Glu Lys Ala Gly Gln His Ile His Glu
                100                 105                 110 aat ggt gct aaa aaa gtt gtt atc aca gct cct ggt gga aac gac gtt     384
Asn Gly Ala Lys Lys Val Val Ile Thr Ala Pro Gly Gly Asn Asp Val
                115                 120                 125 aaa aca gtt gtt ttc aac act aac cac gat atc ctt gat gga act gaa     432
Lys Thr Val Val Phe Asn Thr Asn His Asp Ile Leu Asp Gly Thr Glu
        130                 135                 140 aca gtt atc tca ggt gct tca tgt act aca aac tgt ctt gct cca atg     480
Thr Val Ile Ser Gly Ala Ser Cys Thr Thr Asn Cys Leu Ala Pro Met
145                 150                 155                 160 gct aaa gct tta caa gac aac ttt ggt gtt aaa caa ggt ttg atg act     528
Ala Lys Ala Leu Gln Asp Asn Phe Gly Val Lys Gln Gly Leu Met Thr
                165                 170                 175 act atc cac gca tac act ggt gac caa atg atc ctt gac gga cca cac     576
Thr Ile His Ala Tyr Thr Gly Asp Gln Met Ile Leu Asp Gly Pro His
                180                 185                 190 cgt ggt ggt gac ctt cgt cgt gct cgt gca ggt gct gca aac atc gtt     624
Arg Gly Gly Asp Leu Arg Arg Ala Arg Ala Gly Ala Ala Asn Ile Val
                195                 200                 205
```

FIG. 2A

```
cct aac tca act ggt gct gca aaa gct atc gga ctt gtt atc cca gaa    672
Pro Asn Ser Thr Gly Ala Ala Lys Ala Ile Gly Leu Val Ile Pro Glu
    210                 215                 220 ttg aac ggt aaa ctt gat ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa ttg gtt gca act ctt gaa aaa gac gta act gtc    768
Gly Ser Val Thr Glu Leu Val Ala Thr Leu Glu Lys Asp Val Thr Val
                245                 250                 255 gaa gaa gta aat gca gct atg aaa gca gca gct aac gat tca tac ggt    816
Glu Glu Val Asn Ala Ala Met Lys Ala Ala Ala Asn Asp Ser Tyr Gly
        260                 265                 270 tat act gaa gat cca atc gta tca tct gat atc gtt ggt att tca tac    864
Tyr Thr Glu Asp Pro Ile Val Ser Ser Asp Ile Val Gly Ile Ser Tyr
    275                 280                 285 ggt tca ttg ttt gat gct act caa act aaa gtt caa act gtt gac ggt    912
Gly Ser Leu Phe Asp Ala Thr Gln Thr Lys Val Gln Thr Val Asp Gly
290                 295                 300 aac caa ttg gtt aaa gtt gtt tca tgg tac gat aac gaa atg tca tac    960
Asn Gln Leu Val Lys Val Val Ser Trp Tyr Asp Asn Glu Met Ser Tyr
305                 310                 315                 320 act tca caa ctt gtt cgt aca ctt gag tac ttt gca aaa atc gct aaa   1008
Thr Ser Gln Leu Val Arg Thr Leu Glu Tyr Phe Ala Lys Ile Ala Lys
        325                 330                 335 taa                                                                1011
```

FIG. 2B

```
atg gta gtt aaa gtt ggt att aac ggt ttc ggt cgt atc gga cgt ctt      48
Met Val Val Lys Val Gly Ile Asn Gly Phe Gly Arg Ile Gly Arg Leu
 1               5                  10                  15 gca ttc cgt cgt att caa aac gtt gaa ggt gtt gaa gta act cgt att      96
Ala Phe Arg Arg Ile Gln Asn Val Glu Gly Val Glu Val Thr Arg Ile
             20                  25                  30 aac gat ctt act gac cca aat atg ctt gca cac ttg ttg aaa tat gat     144
Asn Asp Leu Thr Asp Pro Asn Met Leu Ala His Leu Leu Lys Tyr Asp
         35                  40                  45 aca act caa ggt cgt ttc gac ggt aca gtt gaa gtt aaa gat ggt gga     192
Thr Thr Gln Gly Arg Phe Asp Gly Thr Val Glu Val Lys Asp Gly Gly
     50                  55                  60 ttc gaa gtt aac gga aac ttc atc aaa gtt tct gct gaa aaa gat cca     240
Phe Glu Val Asn Gly Asn Phe Ile Lys Val Ser Ala Glu Lys Asp Pro
 65                  70                  75                  80 gaa aac att gac tgg gca act gac ggt gta gaa atc gtt ctt gaa gca     288
Glu Asn Ile Asp Trp Ala Thr Asp Gly Val Glu Ile Val Leu Glu Ala
                 85                  90                  95 act ggt ttc ttt gct aaa aaa gca gct gct gaa aaa cat tta cat gct     336
Thr Gly Phe Phe Ala Lys Lys Ala Ala Ala Glu Lys His Leu His Ala
            100                 105                 110 aac ggt gct aaa aaa gtt gtt atc aca gct cct ggt gga gat gat gtt     384
Asn Gly Ala Lys Lys Val Val Ile Thr Ala Pro Gly Gly Asp Asp Val
        115                 120                 125 aaa act gtt gta ttt aac aca aac cat gac att ctt gac ggt aca gaa     432
Lys Thr Val Val Phe Asn Thr Asn His Asp Ile Leu Asp Gly Thr Glu
    130                 135                 140 act gta att tca ggt gct tca tgt act act aac tgt tta gct cca atg     480
Thr Val Ile Ser Gly Ala Ser Cys Thr Thr Asn Cys Leu Ala Pro Met
145                 150                 155                 160 gct aaa gct ttg caa gat aac ttt ggt gtt aaa caa ggt ttg atg aca     528
Ala Lys Ala Leu Gln Asp Asn Phe Gly Val Lys Gln Gly Leu Met Thr
                165                 170                 175 act atc cac gct tac act ggt gac caa atg atc ctt gac gga cca cac     576
Thr Ile His Ala Tyr Thr Gly Asp Gln Met Ile Leu Asp Gly Pro His
            180                 185                 190 cgt ggt ggt gac ctt cgt cgt gct cgt gct ggt gca agc aac att gtt     624
Arg Gly Gly Asp Leu Arg Arg Ala Arg Ala Gly Ala Ser Asn Ile Val
        195                 200                 205
```

FIG. 3A

```
cct aac tca act ggt gct gct aaa gca atc ggt ctt gta atc cca gaa    672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gaa act tca gtt    768
Gly Ser Val Thr Glu Leu Val Ala Val Leu Glu Lys Glu Thr Ser Val
                245                 250                 255 gaa gaa atc aac gca gca atg aaa gca gct gca aac gat tca tac gga    816
Glu Glu Ile Asn Ala Ala Met Lys Ala Ala Ala Asn Asp Ser Tyr Gly
                260                 265                 270 tac act gaa gac cca atc gta tct tct gat atc atc ggt atg gct tac    864
Tyr Thr Glu Asp Pro Ile Val Ser Ser Asp Ile Ile Gly Met Ala Tyr
            275                 280                 285 ggt tca ttg ttt gat gct act caa act aaa gta caa act gtt gat gga    912
Gly Ser Leu Phe Asp Ala Thr Gln Thr Lys Val Gln Thr Val Asp Gly
        290                 295                 300 aat caa tta gtt aaa gtt gtt tca tgg tat gac aac gaa atg tct tac    960
Asn Gln Leu Val Lys Val Val Ser Trp Tyr Asp Asn Glu Met Ser Tyr
305                 310                 315                 320 act gca caa ctt gtt cgt act ctt gag tac ttt gca aaa atc gct aaa   1008
Thr Ala Gln Leu Val Arg Thr Leu Glu Tyr Phe Ala Lys Ile Ala Lys
                325                 330                 335 taa                                                               1011
```

FIG. 3B

```
atg gta gtt aaa gtt ggt att aac ggt ttt ggc cgt atc gga cgt ctt    48
Met Val Val Lys Val Gly Ile Asn Gly Phe Gly Arg Ile Gly Arg Leu
 1           5                  10                  15 gct ttc cgt cgt att caa aat gta gaa ggt gtt gaa gtt act cgc atc    96
Ala Phe Arg Arg Ile Gln Asn Val Glu Gly Val Glu Val Thr Arg Ile
             20                  25                  30 aac gac ctt aca gat cca aat atg ctt gca cac ttg tta aaa tac gat   144
Asn Asp Leu Thr Asp Pro Asn Met Leu Ala His Leu Leu Lys Tyr Asp
         35                  40                  45 aca act caa ggt cgt ttt gac ggt act gta gaa gtt aaa gat ggt gga   192
Thr Thr Gln Gly Arg Phe Asp Gly Thr Val Glu Val Lys Asp Gly Gly
     50                  55                  60 ttt gac gtt aac gga aaa ttc att aaa gtt tct gct gaa aaa gat cca   240
Phe Asp Val Asn Gly Lys Phe Ile Lys Val Ser Ala Glu Lys Asp Pro
 65                  70                  75                  80 gaa caa att gac tgg gca act gac ggt gtt gaa atc gtt ctt gaa gca   288
Glu Gln Ile Asp Trp Ala Thr Asp Gly Val Glu Ile Val Leu Glu Ala
                 85                  90                  95 act ggt ttc ttt gct aaa aaa gca gct gct gaa aaa cat tta cat gaa   336
Thr Gly Phe Phe Ala Lys Lys Ala Ala Ala Glu Lys His Leu His Glu
            100                 105                 110 aat ggt gct aaa aaa gtt gtt atc act gct cct ggt gga gat gac gtg   384
Asn Gly Ala Lys Lys Val Val Ile Thr Ala Pro Gly Gly Asp Asp Val
        115                 120                 125 aaa aca gtt gta ttt aac act aac cat gat atc ctt gat gga act gaa   432
Lys Thr Val Val Phe Asn Thr Asn His Asp Ile Leu Asp Gly Thr Glu
    130                 135                 140 aca gtt att tca ggt gct tca tgt act aca aac tgt tta gct cca atg   480
Thr Val Ile Ser Gly Ala Ser Cys Thr Thr Asn Cys Leu Ala Pro Met
145                 150                 155                 160 gct aaa gct tta caa gat aac ttt ggc gta aaa caa ggt tta atg act   528
Ala Lys Ala Leu Gln Asp Asn Phe Gly Val Lys Gln Gly Leu Met Thr
                165                 170                 175 aca atc cac gct tac act ggt gat caa atg ctt ctt gat gga cct cac   576
Thr Ile His Ala Tyr Thr Gly Asp Gln Met Leu Leu Asp Gly Pro His
            180                 185                 190 cgt ggt ggt gac tta cgt cgt gcc cgt gct ggt gct aac aat att gtt   624
Arg Gly Gly Asp Leu Arg Arg Ala Arg Ala Gly Ala Asn Asn Ile Val
        195                 200                 205
```

FIG. 4A

```
cct aac tca act ggt gct gct aaa gca atc ggt ctt gtt atc cct gaa      672
Pro Asn Ser Thr Gly Ala Ala Lys Ala Ile Gly Leu Val Ile Pro Glu
    210                 215                 220 tta aat ggt aaa ctt gac ggt gct gca caa cgt gta cca gtt cca aca      720
Leu Asn Gly Lys Leu Asp Gly Ala Ala Gln Arg Val Pro Val Pro Thr
225                 230                 235                 240 ggt tca gta aca gaa tta gta gca gtt ctt aat aaa gaa act tca gta      768
Gly Ser Val Thr Glu Leu Val Ala Val Leu Asn Lys Glu Thr Ser Val
                245                 250                 255 gaa gaa att aac tca gta atg aaa gct gca gct aat gat tca tat ggt      816
Glu Glu Ile Asn Ser Val Met Lys Ala Ala Ala Asn Asp Ser Tyr Gly
                    260                 265                 270 tac act gaa gat cca atc gta tca tct gat atc gtt ggt atg tct ttc      864
Tyr Thr Glu Asp Pro Ile Val Ser Ser Asp Ile Val Gly Met Ser Phe
            275                 280                 285 ggt tca tta ttc gat gct act caa act aaa gta caa act gtt gat gga      912
Gly Ser Leu Phe Asp Ala Thr Gln Thr Lys Val Gln Thr Val Asp Gly
        290                 295                 300 aat caa tta gtt aaa gtt gtt tca tgg tat gac aat gaa atg tct tac      960
Asn Gln Leu Val Lys Val Val Ser Trp Tyr Asp Asn Glu Met Ser Tyr
305                 310                 315                 320 act gct caa ctt gat cgt aca ctt gag tac ttt gca aaa atc gct aaa     1008
Thr Ala Gln Leu Asp Arg Thr Leu Glu Tyr Phe Ala Lys Ile Ala Lys
                325                 330                 335 taa                                                                 1011
```

FIG. 4B

| | | | | | | | | | | | | | | | |
|---|---|---|---|---|---|---|---|---|---|---|---|---|---|---|---|
| atg | gta | gtt | aaa | gtt | ggt | att | aac | ggt | ttc | gga | cgt | atc | ggt | cgt | ctt | 48 |
| Met | Val | Val | Lys | Val | Gly | Ile | Asn | Gly | Phe | Gly | Arg | Ile | Gly | Arg | Leu |
| 1 | | | | 5 | | | | | 10 | | | | | 15 | |

| | | | | | | | | | | | | | | | |
|---|---|---|---|---|---|---|---|---|---|---|---|---|---|---|---|
| gca | ttc | cgt | cgt | att | caa | aat | gtt | gaa | ggt | gtt | gaa | gta | act | cgt | atc | 96 |
| Ala | Phe | Arg | Arg | Ile | Gln | Asn | Val | Glu | Gly | Val | Glu | Val | Thr | Arg | Ile |
| | | | 20 | | | | | 25 | | | | | 30 | | |

| | | | | | | | | | | | | | | | |
|---|---|---|---|---|---|---|---|---|---|---|---|---|---|---|---|
| aat | gac | ctt | aca | gat | cct | aac | atg | ctt | gca | cac | ttg | ttg | aaa | tat | gat | 144 |
| Asn | Asp | Leu | Thr | Asp | Pro | Asn | Met | Leu | Ala | His | Leu | Leu | Lys | Tyr | Asp |
| | | | 35 | | | | | 40 | | | | | 45 | | |

| | | | | | | | | | | | | | | | |
|---|---|---|---|---|---|---|---|---|---|---|---|---|---|---|---|
| aca | act | caa | ggt | cgt | ttt | gac | ggt | aca | gtt | gaa | gtt | aaa | gat | ggt | gga | 192 |
| Thr | Thr | Gln | Gly | Arg | Phe | Asp | Gly | Thr | Val | Glu | Val | Lys | Asp | Gly | Gly |
| | | 50 | | | | | 55 | | | | | 60 | | | |

| | | | | | | | | | | | | | | | |
|---|---|---|---|---|---|---|---|---|---|---|---|---|---|---|---|
| ttc | gaa | gtt | aac | gga | agc | ttt | gtt | aaa | gtt | tct | gca | gaa | cgc | gaa | cca | 240 |
| Phe | Glu | Val | Asn | Gly | Ser | Phe | Val | Lys | Val | Ser | Ala | Glu | Arg | Glu | Pro |
| 65 | | | | | 70 | | | | | 75 | | | | | 80 |

| | | | | | | | | | | | | | | | |
|---|---|---|---|---|---|---|---|---|---|---|---|---|---|---|---|
| gca | aac | att | gac | tgg | gct | act | gat | ggt | gta | gac | atc | gtt | ctt | gaa | gca | 288 |
| Ala | Asn | Ile | Asp | Trp | Ala | Thr | Asp | Gly | Val | Asp | Ile | Val | Leu | Glu | Ala |
| | | | | 85 | | | | | 90 | | | | | 95 | |

| | | | | | | | | | | | | | | | |
|---|---|---|---|---|---|---|---|---|---|---|---|---|---|---|---|
| aca | ggt | ttc | ttc | gct | tct | aaa | gca | gct | gct | gaa | caa | cac | att | cac | gct | 336 |
| Thr | Gly | Phe | Phe | Ala | Ser | Lys | Ala | Ala | Ala | Glu | Gln | His | Ile | His | Ala |
| | | | | 100 | | | | | 105 | | | | | 110 | |

| | | | | | | | | | | | | | | | |
|---|---|---|---|---|---|---|---|---|---|---|---|---|---|---|---|
| aac | ggt | gcg | aaa | aaa | gtt | gtt | atc | aca | gct | cct | ggt | gga | aat | gac | gtt | 384 |
| Asn | Gly | Ala | Lys | Lys | Val | Val | Ile | Thr | Ala | Pro | Gly | Gly | Asn | Asp | Val |
| | | | 115 | | | | | 120 | | | | | 125 | | |

| | | | | | | | | | | | | | | | |
|---|---|---|---|---|---|---|---|---|---|---|---|---|---|---|---|
| aaa | aca | gtt | gtt | tac | aac | act | aac | cat | gat | att | ctt | gat | gga | act | gaa | 432 |
| Lys | Thr | Val | Val | Tyr | Asn | Thr | Asn | His | Asp | Ile | Leu | Asp | Gly | Thr | Glu |
| | | | 130 | | | | | 135 | | | | | 140 | | |

| | | | | | | | | | | | | | | | |
|---|---|---|---|---|---|---|---|---|---|---|---|---|---|---|---|
| aca | gtt | atc | tca | ggt | gct | tca | tgt | act | aca | aac | tgt | tta | gct | cca | atg | 480 |
| Thr | Val | Ile | Ser | Gly | Ala | Ser | Cys | Thr | Thr | Asn | Cys | Leu | Ala | Pro | Met |
| 145 | | | | | 150 | | | | | 155 | | | | | 160 |

| | | | | | | | | | | | | | | | |
|---|---|---|---|---|---|---|---|---|---|---|---|---|---|---|---|
| gct | aaa | gca | tta | caa | gat | aac | ttt | ggt | gta | aaa | caa | ggt | tta | atg | act | 528 |
| Ala | Lys | Ala | Leu | Gln | Asp | Asn | Phe | Gly | Val | Lys | Gln | Gly | Leu | Met | Thr |
| | | | | 165 | | | | | 170 | | | | | 175 | |

| | | | | | | | | | | | | | | | |
|---|---|---|---|---|---|---|---|---|---|---|---|---|---|---|---|
| act | atc | cat | ggt | tac | act | ggt | gac | caa | atg | gtt | ctt | gac | gga | cca | cac | 576 |
| Thr | Ile | His | Gly | Tyr | Thr | Gly | Asp | Gln | Met | Val | Leu | Asp | Gly | Pro | His |
| | | | 180 | | | | | 185 | | | | | 190 | | |

| | | | | | | | | | | | | | | | |
|---|---|---|---|---|---|---|---|---|---|---|---|---|---|---|---|
| cgt | ggt | ggt | gat | ctt | cgt | cgt | gct | cgt | gca | gct | gca | gca | aac | atc | gtt | 624 |
| Arg | Gly | Gly | Asp | Leu | Arg | Arg | Ala | Arg | Ala | Ala | Ala | Ala | Asn | Ile | Val |
| | | | 195 | | | | | 200 | | | | | 205 | | |

FIG. 5A

```
cct aac tca act ggt gct gct aaa gca atc ggt ctt gtt atc cca gaa    672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gat act tca gta    768
Gly Ser Val Thr Glu Leu Val Ala Val Leu Glu Lys Asp Thr Ser Val
                245                 250                 255 gaa gaa atc aat gca gct atg aaa gca gca gct aac gat tca tac ggt    816
Glu Glu Ile Asn Ala Ala Met Lys Ala Ala Ala Asn Asp Ser Tyr Gly
            260                 265                 270 tac act gaa gat gct atc gta tca tca gat atc gta ggt att tct tac    864
Tyr Thr Glu Asp Ala Ile Val Ser Ser Asp Ile Val Gly Ile Ser Tyr
        275                 280                 285 ggt tca tta ttt gat gct act caa act aaa gta caa act gtt gat gga    912
Gly Ser Leu Phe Asp Ala Thr Gln Thr Lys Val Gln Thr Val Asp Gly
    290                 295                 300 aat caa ttg gtt aaa gtt gtt tca tgg tat gac aat gaa atg tct tac    960
Asn Gln Leu Val Lys Val Val Ser Trp Tyr Asp Asn Glu Met Ser Tyr
305                 310                 315                 320 act gct caa ctt gtt cgt act ctt gag tac ttt gca aaa atc gct aaa   1008
Thr Ala Gln Leu Val Arg Thr Leu Glu Tyr Phe Ala Lys Ile Ala Lys
                325                 330                 335 taa                                                               1011
```

FIG. 5B

```
                    1                                                           50
        DysGapC  ATGGTAGTTA AAGTTGGTAT TAACGGTTTC GGTCGTATCG GACGTCTTGC
        SpyGapC  ---------- ---------- ---------- ---------- ----------
        SeqGapC  ---------- ---------- ---------- ---------- ----------
      ParaUbGapC ---------- ---------- -------t-- --c------- ----------
        UberGapc ---------- ---------- ---------- ---------- ----------
      AgalGapCDNA ---------- ---------- ---------- ---------- -t--------
        SiniGapC ---------- ---------- ---------- --a------- -t--------
        BovGapC  ---------- ---------- ---------- ----c----- -g--c--g-t 51                                                         100
        DysGapC  ATTCCGTCGT ATTCAAAATG TTGAAGGTGT TGAAGTAACT CGTATCAACG
        SpyGapC  ------c--- --------ca -c-------- ---------- --------t-
        SeqGapC  ---------- ---------- ---------- ---------- ----------
      ParaUbGapC t--------- ---------- -a-------- ------t--- --c-------
        UberGapc ---------- --------c- ---------- ---------- -----t----
      AgalGapCDNA ---------c --c-----c- -a-------- ------t--- ----------
        SiniGapC ---------- ---------- ---------- ---------- --------t-
        BovGapC  cac-a-ggc- gc-ttt---t c--gcaaa-- g--ca-cgtc gcc-----t-

101                                                        150
        DysGapC  ACC...TTAC AGATCCAAAC ATGCTTGCAC ACTTGTTGAA ATACGATACA
        SpyGapC  ---...---- --------t- ---------- ---------- ---c------
        SeqGapC  ---...---- ---------- ---------- ---------- ---c------
      ParaUbGapC ---...---- --------t- ---------- -------a-- ---c------
        UberGapc -t-...---- t--c-----t ---------- ---------- ---t------
      AgalGapCDNA ---...---- ---------- ---------- ---------- ---t--c---
        SiniGapC ---...---- ------t--- ---------- ---------- ---t------
        BovGapC  ---cct-c-t t--c-ttc-- taca-g-tct --a----cc- g--t---t-c
```

FIG. 6A

```
                151                                                    200
   DysGapC ACTCAAGGAC GTTTTGACGG AACTGTTGAA GTTAAAGAAG GTGGATTTGA
   SpyGapC ---------- -------t-- a--a------ ---------- -------t--
   SeqGapC ---------a- ---------- a--t------ ---------- -------t--
 ParaUbGapC ---------- ---------- ---t--a--- --------t- -------t--
   UberGapc ---------- ----c----- ---a------ --------t- -------c--
AgalGapCDNA ---------- ----c----- ---t------ ---------- -------c--
   SiniGapC ---------- ---------- ---a------ --------t- -------c--
   BovGapC --c--c--ca ag--ca---- c--a--ca-g -cag-ga-c- -gaagc-c-t 201                                                    250
   DysGapC AGTAAACGGA AACTTCATCA AAGTTTCTGC TGAACGTGAT CCAGAAAACA
   SpyGapC ---a------ ---------- ---------- ------t--- ----------
   SeqGapC ---a------ ---------- ---------- ------t--- ----------
 ParaUbGapC c--------- --a-----t- ---------- ----aaa--- ------c-a-
   UberGapc ---------- ---------- ---------- ----aaa--- ----------
AgalGapCDNA ---------t c-a--tg-t- ---------- ------c--a ----c-----
   SiniGapC ---------- -g---tg-t- ---------- a-----c--a ----c-----
   BovGapC ca-c--t--- --ggc----- cca-c-tcca g--g--a--- --t-cc----

251                                                    300
   DysGapC TCGACTGGGC AACTGACGGT GTTGAAATCG TTCTGGAAGC AACTGGTTTC
   SpyGapC -c-------- ------t--g ---------- ---------- ----------
   SeqGapC -c-------- ------c--- ---------- ---------- ----------
 ParaUbGapC -t-------- ------c--- ---------- ---------- ----------
   UberGapc -t-------- ------c--- --a------- ---------- ----------
AgalGapCDNA -t-------- t-----t--c --a------- ---------- ----------
   SiniGapC -t-------- t-----t--- --a--c---- ---------- ---a------
   BovGapC -ca-g----g tga--ct--- -c---gtat- -ag-g--gt- c-----gg--

301                                                    350
   DysGapC TTTGCTAAAA AAGAAGCTGC TGAAAAACAC TTACATGCTA ACGGTGCTAA
   SpyGapC ---------- -------a-- ---------- ---------- ----------
   SeqGapC ---------- ---------- --------c- ---------- ----------
 ParaUbGapC ---------- ---c------ --------t- --------aa- -t--------
   UberGapc ---------- ---c------ --------t- ---------- ----------
AgalGapCDNA -----atc-- -----aaa-- --g-c----- a-c----aa- -t--------
   SiniGapC --c---tct- ---c------ ----c----- a-t--c---- ------g--
   BovGapC --ca---cc- tg--gaag-- --gggct--- --ga-g-g-. ..--c--c--

351                                                    400
   DysGapC AAAAGTTGTT ATCACAGCTC CTGGTGGAAA CGACGTTAAA ACAGTTGTTT
   SpyGapC ---------- ---------- ---------- ---t------ ----------
   SeqGapC ---------- ---------- ---------- --------.-- ----------
 ParaUbGapC ---------- -----t---- --------g- t-----g--- --------a-
   UberGapc ---------- ---------- --------g- t--t------ --t-----a-
AgalGapCDNA ---------- ---------- ---------- ---------- ----------
   SiniGapC ---------- ---------- ---------- t--------- ----------
   BovGapC g-gg--ca-c ---t-t--a- --tc--...c ---t-ccccc -tgt----ga
```

FIG. 6B

```
              401                                                      450
   DysGapC  TCAACACTAA CCACGA.CAT TCTTGACGGT ACTGAAACAG TTATCTCAGG
   SpyGapC  ---------- ------.--- ---------- ---------- ----------
   SeqGapC  ---------- ------.--- ---------- ---------- ----------
 ParaUbGapC  -t-------- ---t--.t-- c-----t--a ---------- ----t-----
   UberGapc  -t-----a-- ---t--.--- ---------- --a-----t- -a--t-----
 AgalGapCDNA  ---------- ------.t-- c-----t--a ---------- ----------
   SiniGapC  a--------- ---t--.t-- ------t--a ---------- ----------
   BovGapC  -ggg-gtg-- -------a-g -.a-a--aac --cctc-aga --g--agcaa 451                                                      500
   DysGapC  TGCTTCATGT ACTACAAACT GTTTAGCTCC TATGGCTAAA GCTCTTCACG
   SpyGapC  ---------- ---------- ---------- t--------- ---c-t--c-
   SeqGapC  ---------- ---------- ---------- t--------- ---c-t--c-
 ParaUbGapC  ---------- ---------- ---------- ---------- -----a----
   UberGapc  ---------- ----t----- ---------- ---------- -----g----
 AgalGapCDNA  ---------- ---------- --c-t----- ---------- -----a----
   SiniGapC  ---------- ---------- ---------- ---------- --a--a----
   BovGapC  ---c--c--c --c--c---- -c--g--c-- cc----c--g -tca-c--t-

501                                                      550
   DysGapC  ATGCATTTGG TATCCAAAAA GGTCTTATGA CTACAATCCA CGCTTATACT
   SpyGapC  --gca--c-- -a--c--a-- ---c------ ----a----- ----------
   SeqGapC  --gca----- -a--c--a-- ---c------ ----a----- ----------
 ParaUbGapC  ---------- cg-a------ ---t-a---- ----a----- ----------
   UberGapc  ---------- -g-------- ---t-g---- -a--t----- ----------
 AgalGapCDNA  -c-------- -g-------- ---t-g---- ----t----- ---a------
   SiniGapC  ---------- -g-a------ ---t-a---- ----t----- t-g-------
   BovGapC  -cc------- ca-cgtgg-g --ac------ -c--tg---- ---cat----

551                                                      600
   DysGapC  GGTGACCAAA TGATCCTTGA CGGACCACAC CGTGGTGGTG ACCTTCGTCG
   SpyGapC  ---------- ---------- ---------- ---------- ----------
   SeqGapC  ---------- -----g---- t----ac-gt g--------- -t--------
 ParaUbGapC  -----t---- --c-t----- t-----t--- ---------- --t-a-----
   UberGapc  ---------- ---------- ---------- ---------- ----------
 AgalGapCDNA  ---------- ---------- ---------- ---------- ----------
   SiniGapC  ---------- --g-t----- ---------- ---------- -t--------
   BovGapC  -ccac---g- a--ctg-g-- t--c--ctc- ...--gaagc tgtgg---ga 601                                                      650
   DysGapC  TGCTCGTGCT GGTGCTGCAA ACATTGTTCC TAACTCAACT GGTGCTGCTA
   SpyGapC  ---a--c--- ---------- ---------- ---------- ----------
   SeqGapC  ---------- ---------- ---------- ---------- ------cg--
 ParaUbGapC  ---c------ ------aac- -t--t----- ---------- ----------
   UberGapc  ---------- -----aagc- ----t----- ---------- ----------
 AgalGapCDNA  ----------a ---------- ---------- ---------- --------a-
   SiniGapC  ----------a -c---a---- ---------- ---------- ----------
   BovGapC  c-gc--a-gg -c---ccag- -t---a-c-- -gct--t--- --c-----c-
```

FIG. 6C

```
                 651                                                        700
    DysGapC  AAGCTATCGG TCTTGTTATC CCAGAATTGA ATGGTAAACT TGATGGTGCT
    SpyGapC  ---------- ---------- ------c-t- -c-------- ----------
    SeqGapC  ---------- ---------- -------g-- -c-------- ----------
 ParaUbGapC  ----a----- ---------- --t-----a- -t-------- ----------
    UberGapc ----a----- ------a--- --------a- -t-------- ----------
 AgalGapCDNA ---------- a--------- --------g- -c-------- ---t------
    SiniGapC ----a----- ---------- --------a- -t-------- ----------
    BovGapC  -g--cg-g-- caag--c--- --t--gc-c- -c--g--g-- cact--catg 701                                                        750
    DysGapC  GCACAACGTG TTCCTGTTCC AACTGGATCA GTAACTGAGT TGGTTGTAAC
    SpyGapC  ---------- ---------- ---------- --------g- ------t---
    SeqGapC  ---------- ---------- ---------- --------g- ------t---
 ParaUbGapC  ---------- -a--a----- ---a--t--- -----a---- -a--a---gt
    UberGapc ---------- ---------- ---------- ---------- -a--a---gt
 AgalGapCDNA ---------- ---------- ---------- ---------- ----------
    SiniGapC ---------- ---------- ---------- ---------- -a--a---gt
    BovGapC  --cttc--c- -c--cac--- c-ac-tg--t --tgtg--tc --acctgccg 751                                                        800
    DysGapC  TCTTGATAAA AACGTTTCTG TTGACGAAAT CAACGCTGCT ATGAAAGCTG
    SpyGapC  ------c--- a---t----- ----c----- ----t-t--- ----------
    SeqGapC  ------c--- a---t----- ----c----- ------t--- ----------
 ParaUbGapC  ----a-t--- --aac---a- -a-------- t---t---ta ----------
    UberGapc ---------- --aac---a- ---------- ---------a --------a-
 AgalGapCDNA ---------- ----taa--- -c------g- a--t------ --------a-
    SiniGapC ---------- --tac---a- -a-------- ---t------ --------a-
    BovGapC  c--g--g--- cct-ccaagt a---t--g-- ---gaag-tg g----gcag- 801                                                        850
    DysGapC  CTTCAAACGA CAGTTTCGGT TACACTGAAG ATCCAATTGT TTCTTCAGAT
    SpyGapC  --t------- -agc-t---- ---------- ---------- t---------
    SeqGapC  --t------- -agc-t---- ---------- ---------- t---------
 ParaUbGapC  -ag-t--t-- -----at--- ---------- ---------- ---a--t---
    UberGapc --g------- -----a---a ---------- -c-------- ------t---
 AgalGapCDNA -ag-t----- -----a---- --t------- ---------- ---a--t---
    SiniGapC -ag-t----- -----a---- ---------- --g-t----- ---a------
    BovGapC  -gt--g-g-g cc-tct-aag gg--t-ct-- gctac-ct-a ggaccag-t-

851                                                        900
    DysGapC  ATCGTAGGCG TGTCATA... CGGTTCATTG TTTGACGCAA CTCAAACTAA
    SpyGapC  --------cg -a-----... ---------- -----c--a- ----------
    SeqGapC  --------cg -a-----... ---------- -----c--a- ----------
 ParaUbGapC  -----t--ta ----t-t... ---------a --c------- ----------
    UberGapc ---a-c--ta --g-t--... ---------- ---------- ----------
 AgalGapCDNA -----t--ta -t-----... ---------- ---------- ----------
    SiniGapC --------ta -t--t--... ---------a ---------- ----------
    BovGapC  g--tcct-cg ac-tca-cag --a-a-tcac -c-tc-a-ct tcg-tg--gg
```

FIG. 6D

```
              901                                                    950
  DysGapC AGTTATGGAA GTTGACGGAT CACAATTGGT TAAAGTTGTA TCATGGTATG
  SpyGapC ---aatggaa -----c---t ca-------- ---------a ----------
  SeqGapC ---tatggaa -----t---t ca-------- ---------a ----------
ParaUbGapC ---a------ -----t---- -t-----a-- ---------- ----------
  UberGapc ---a------ -----t---- -t-----a-- ---------- ----------
AgalGapCDNA ---t------ -----c--t- -c-------- ---------- --------c-
  SiniGapC ---a------ -----t---- -t-------- ---------- ----------
  BovGapC g-ctggc-t- -ccctcaacg -c--c--t-- c--gc-ca-- --c-----c-

951                                                   1000
  DysGapC ACAATGAAAT GTCTTACACT GCTCAACTTG TTCGTACACT TGAGTATTTT
  SpyGapC ----c----- ---------- ---------- -a-----t-- ---------c
  SeqGapC ----c----- ---------- ---------- ---------- ----------
ParaUbGapC ----t----- ---------- ---------- a--------- ----------
  UberGapc ----c----- ---------- --a------- -------t-- ----------
AgalGapCDNA -t--c----- ---a------ t-a------- ---------- ----------
  SiniGapC ----t----- ---------- ---------- -------t-- ----------
  BovGapC ----t---t- tggc----gc aaa--gg--- ---------- ----------

1001       1018
  DysGapC GCAAAAATCG CTAAATAA
  SpyGapC --------t- --------
  SeqGapC ---------- --------
ParaUbGapC ---------- --------
  UberGapc ---------- --------
AgalGapCDNA ---------- --------
  SiniGapC ---------- --------
  BovGapC ---------- --------
```

FIG. 6E

```
              1                                                         50
    DysGapC   MVVKVGINGF GRIGRLAFRR IQNVEGVEVT RIND.LTDPN MLAHLLKYDT
    SpyGapC   ---------- ---------- ---I------ ----.----- ----------
    SeqGapC   ---------- ---------- ---------- ----.----- ----------
   PUberGapC  ---------- ---------- ---------- ----.----- ----------
    UberGapC  ---------- ---------- ---------- ----.----- ----------
    AgalGapC  ---------- ---------- ---------- ----.----- ----------
   IniaeGapC  ---------- ---------- ---------- ----.----- ----------
     BovGapC  ---------- ------vt-a af-sgk-div a---pfi-lh ymvymfq--s 51                                                       100
    DysGapC   TQGRFDGTVE VKEGGFEVNG NFIKVSAERD PENIDWATDG VEIVLEATGF
    SpyGapC   ---------- ---------- ---------- ---------- ----------
    SeqGapC   ---------- ---------- ---------- ---------- ----------
   PUberGapC  ---------- --d---d--- k-------k- --q------- ----------
    UberGapC  ---------- --d------- --------k- ---------- ----------
    AgalGapC  ---------- ---------- q-v------e -a-------- ----------
   IniaeGapC  ---------- --d------- s-v------e -a-------- -d--------
     BovGapC  -h-k-n---k aen-klvi-- ka-tifq--- -a--k-gda- a-y-v-s--v 101                                                      150
    DysGapC   FAKKEAAEKH LHANGAKKVV ITAPGGNDVK TVVFNTNHDI LDGTETVISG
    SpyGapC   ---------- ---------- ---------- ---------- ----------
    SeqGapC   ---------p ---------- ---------- qlfstltts- ----------
   PUberGapC  ----a----- --e------- ------d--- ---------- ----------
    UberGapC  ----a----- ---------- ------d--- ---------- ----------
    AgalGapC  --s--k-gq- i-e------- ---------- ---------- ----------
   IniaeGapC  --s-a---q- i--------- ---------- ---y------ ----------
     BovGapC  -ttm-k-ga- -.kg---r-i -s--sa.-ap mf-mgv--ek ynn-lkiv-n
```

FIG. 7A

```
              151                                                        200
   DysGapC  ASCTTNCLAP MAKALHDAFG IQKGLMTTIH AYTGDQMILD GPHRGGDLRR
   SpyGapC  ---------- ---------- ---------- ---------- ----------
   SeqGapC  ---------- ---------- ---------- --------v- -hrg------
 PUberGapC  ---------- ----q-n--- v--------- ---------- ----------
  UberGapC  ---------- ----q-n--- v--------- ---------- ----------
  AgalGapC  ---------- ----q-n--- v--------- ---------- ----------
 IniaeGapC  ---------- ----q-n--- v--------- g------v-- ----------
   BovGapC  ---------- l--vih-h-- ive-----v- -i-at-ktv- --.s-klw-d 201                                                        250
   DysGapC  ARAGAANIVP NSTGAAKAIG LVIPELNGKL DGAAQRVPVP TGSVTELVVT
   SpyGapC  ---------- ---------- ---------- ---------- ----------
   SeqGapC  ---------- -----r---- ---------- ---------- ----------
 PUberGapC  -----n---- ---------- ---------- ---------- --------av
  UberGapC  -----s---- ---------- ---------- ---------- --------av
  AgalGapC  ---------- ---------- ---------- ---------- --------a-
 IniaeGapC  ---a------ ---------- ---------- ---------- --------av
   BovGapC  g-ga-q--i- a-------v- k--------- t-m-f---t- nv--vd-tcr 251                                                        300
   DysGapC  LDKNVSVDEI NAAMKAASND S....PGYTE DPIVSSDIVG VSYGSLFDAT
   SpyGapC  ---------- -s-------- -....----- ---------- ----------
   SeqGapC  ---------- ---------- -....----- ---------- ----------
 PUberGapC  -n-et--e-- -sv----a-- -....y---- ---------- m-f-------
  UberGapC  -e-et--e-- -------a-- -....y---- -------i-- ma--------
  AgalGapC  -e-d-t-e-v -------a-- -....y---- ---------- i---------
 IniaeGapC  -e-dt--e-- -------a-- -....y---- -a-------- i---------
   BovGapC  -e-paky--- kkvv-q--eg plkgilg--- -qv--c-fns dths-t---g 301                                          341
   DysGapC  QTKVMEVDGS QLVKVVSWYD NEMSYTAQLV RTLEYFAKIA K
   SpyGapC  ---------- ---------- ---------- ---------- -
   SeqGapC  ---------- ---------- ---------- ---------- -
 PUberGapC  ----qt---n ---------- ---------d ---------- -
  UberGapC  ----qt---n ---------- ---------- ---------- -
  AgalGapC  ----qt---n ---------- ------s--- ---------- -
 IniaeGapC  ----qt---n ---------- ---------- ---------- -
   BovGapC  agial...nd hf--li---- --fg-sk--- ---------- -
```

FIG. 7B

IMMUNIZATION OF DAIRY CATTLE WITH GAPC PROTEIN AGAINST *STREPTOCOCCUS* INFECTION

CROSS-REFERENCE TO RELATED APPLICATION

This application is a continuation-in-part of U.S. patent application Ser. No. 09/878,781, filed Jun. 11, 2001 now allowed, from which application priority is claimed under 35 USC §120, which is related to provisional patent application Ser. No. 60/211,022, filed Jun. 12, 2000, from which application priority is claimed under 35 USC §119(e)(1), and which applications are incorporated herein by reference in their entireties.

TECHNICAL FIELD

The present invention relates generally to bacterial antigens and genes encoding the same. More particularly, the present invention pertains to the cloning, expression and characterization of the GapC plasmin-binding proteins from *Streptococcus dysgalactiae, Streptococcus agalactiae, Streptococcus uberis, Streptococcus parauberis*, and *Streptococcus iniae*, and the use of the same in vaccine compositions.

BACKGROUND

Mastitis is an infection of the mammary gland usually caused by bacteria or fungus. The inflammatory response following infection results in decreased milk yield as well as quality, and causes major annual economic losses to the dairy industry.

Among the bacterial species most commonly associated with mastitis are various species of the genus *Streptococcus*, including *Streptococcus aureus, Streptococcus uberis* (untypeable), *Streptococcus agalactiae* (Lancefield group B), *Streptococcus dysgalactiae* (Lancefield group C), *Streptococcus zooepidemicus*, and the Lancefield groups D, G, L and N streptococci. Some of those species are contagions (e.g. *S. agalactiae*), while others are considered environmental pathogens (e.g. *S. dysgalactiae* and *S. uberis*).

The environmental pathogen *S. uberis* is responsible for about 20% of all clinical cases of mastitis (Bramley, A. J. and Dodd, F. H. (1984) *J. Dairy Res.* 51:481–512; Bramley, A. J. (1987) *Animal Health Nutrition* 42:12–16; Watts, J. L. (1988) *J. Dairy Sci.* 71:1616–1624); it is the predominant organism isolated from mammary glands during the non-lactating period (Bramley, A. J. (1984) *Br. Vet. J.* 140:328–335; Bramley and Dodd (1984) *J. Dairy Res.* 51:481–512; Oliver, S. P. (1988) *Am. J. Vet. Res.* 49:1789–1793).

Mastitis resulting from infection with *S. uberis* is commonly subclinical, characterized by apparently normal milk with an increase in somatic cell counts due to the influx of leukocytes. The chemical composition of milk is changed due to suppression of secretion with the transfer of sodium chloride and bicarbonate from blood to milk, causing a shift of pH to a more alkaline level. *S. uberis* mastitis may also take the form of an acute clinical condition, with obvious signs of disease such as clots or discoloration of the milk and swelling or hardness of the mammary gland. Some cases of the clinical disease can be severe and pyrexia may be present. For a review of the clinical manifestations of *S. uberis* mastitis, see, Bramley (1991) Mastitis: physiology or pathology. p. 3–9. In C. Burvenich, G. Vandeputte-van Messom, and A. W. Hill (ed.), *New insights into the pathogenesis of mastitis*. Rijksuniversiteit Gent, Belgium; and Schalm et al. (1971) The mastitis complex-A brief summary. p. 1–3. In *Bovine Mastitis*. Lea & Febiger, Philadelphia Conventional antibacterial control methods such as teat dipping and antibiotic therapy are effective in the control of many types of contagious mastitis, but the environmental organisms typically found in all dairy barns are often resistant to such measures. Vaccination is therefore an attractive strategy to prevent infections of the mammary glands, and has been shown to be beneficial in the case of some contagious mastitis pathogens.

The literature is limited regarding vaccination studies with *S. dysgalactiae* and *S. uberis*, and variable results have been observed. In some cases, immunization has resulted in increased sensitivity to the specific organism and in other cases strain-specific protection has been obtained.

For example, previous studies have shown that primary infection with *S. uberis* can considerably reduce the rate of infection following a second challenge with the same strain (Hill, A. W. (1988) *Res. Vet. Sci.* 44:386–387). Local vaccination with killed *S. uberis* protects the bovine mammary gland against intramammary challenge with the homologous strain (Finch et al. (1994) *Infect. Immun.* 62:3599–3603). Similarly, subcutaneous vaccination with live *S. uberis* has been shown to cause a dramatic modification of the pathogenesis of mastitis with the same strain (Hill et al. (1994) FEMS *Immunol. Med. Microbiol.* 8:109–118). Animals vaccinated in this way shed fewer bacteria in their milk and many quarters remain free of infection.

Nonetheless, vaccination with live or attenuated bacteria can pose risks to the recipient. Further, it is clear that conventional killed vaccines are in general largely ineffective against *S. uberis* and *S. agalactiae*, either due to lack of protective antigens on in vitro-grown cells or masking of these antigens by molecular mimicry.

The current lack of existing mastitis vaccines against *S. agalactiae* or the contagious streptococcus strains is due at least in part to a lack of knowledge regarding the virulence determinants and protective antigens produced by those organisms which are involved in invasion and protection of the mammary gland (Collins et al. (1988) *J. Dairy Res.* 55:25–32; Leigh et al. (1990) *Res. Vet. Sci.* 49: 85–87; Marshall et al. (1986) *J. Dairy Res.* 53: 507–514).

*S. dysgalactiae* is known to bind several extracellular and plasma-derived proteins such as fibronectin, fibrinogen, collagen, alpha-II-macroglobulin, IgG, albumin and other compounds. The organism also produces hyaluronidase and fibrinolysin and is capable of adhering to and invading bovine mammary epithelial cells. However, the exact roles of the bacterial components responsible for these phenotypes in pathogenesis is not known.

Similarly, the pathogenesis of *S. uberis* infection is poorly understood. Furthermore, the influence of *S. uberis* virulence factors on host defense mechanisms and mammary gland physiology is not well defined. Known virulence factors associated with *S. uberis* include a hyaluronic acid capsule (Hill, A. W. (1988) *Res. Vet. Sci.* 45:400–404), hyaluronidase (Schaufuss et al. (1989) *Zentralbl. Bakteriol. Ser. A* 271:46–53), R-like protein (Groschup, M. H. and Timoney, J. F. (1993) *Res. Vet. Sci.* 54:124–126), and a cohemolysin, the CAMP factor, also known as UBERIS factor (Skalka, B. and Smola, J. (1981) *Zentralbl. Bakteriol. Ser. A* 249:190–194), R-like protein, plasminogen activator and CAMP factor. However, very little is known of their roles in pathogenicity.

The use of virulence determinants from Streptococcus as immunogenic agents has been proposed. For example, the CAMP factor of *S. uberis* has been shown to protect vertebrate subjects from infection by that organism (Jiang, U.S. Pat. No. 5,863,543).

The γ antigen of the group B *Streptococci* strain A909 (ATCC No. 27591) is a component of the c protein marker complex, which additionally comprises an α and β subunit (Boyle, U.S. Pat. No. 5,721,339). Subsets of serotype Ia, II, and virtually all serotype Ib cells of group B streptococci, have been reported to express components of the c protein. Use of the γ subunit as an immunogenic agent against infections by Lancefield Group B *Streptococcus* infection has been proposed. However, its use to prevent or treat bacterial infections in animals, including mastitis in cattle, has not been studied.

The group A streptococcal M protein is considered to be one of the major virulence factors of this organism by virtue of its ability to impede attack by human phagocytes (Lancefield, R. C. (1962) *J. Immunol.* 89:307–313). The bacteria persist in the infected tissue until antibodies are produced against the M molecule. Type-specific antibodies to the M protein are able to reverse the antiphagocytic effect of the molecule and allow efficient clearance of the invading organism.

M proteins are one of the key virulence factors of *Streptococcus pyogenes*, due to their involvement in mediating resistance to phagocytosis (Kehoe, M. A. (1991) *Vaccine* 9:797–806) and their ability to induce potentially harmful host immune responses via their superantigenicity and their capacity to induce host-cross-reactive antibody responses (Bisno, A. L. (1991) *New Engl. J Med.* 325:783–793; Froude et al. (1989) *Curr. Top. Microbiol. Immunol.* 145:5–26; Stollerman, G. H. (1991) *Clin. Immunol. Immunopathol.* 61:131–142).

However, obstacles exist to using intact M proteins as vaccines. The protein's opsonic epitopes are extremely type-specific, resulting in narrow, type-specific protection. Further, some M proteins appear to contain epitopes that cross react with tissues of the immunized subject, causing a harmful autoimmune response (See e.g., Dale, J. L. and Beached, G. H. (1982) *J. Exp. Med* 156:1165–1176; Dale, J. L. and Beached, G. H. (1985) *J. Exp. Med.* 161:113–122; Baird, R. W., Bronze, M. S., Drabs, W., Hill, H. R., Veasey, L. G. and Dale, J. L. (1991) *J. Immun.* 146:3132–3137; Bronze, M. S. and Dale, J. L. (1993) *J. Immun* 151:2820–2828; Cunningham, M. W. and Russell, S. M. (1983) *Infect. Immun.* 42:531–538).

Chimeric proteins containing three different fibronectin binding domains (FNBDS) derived from fibronectin binding proteins of *S. dysgalactiae* and *Staphylococcus aureus* have been expressed on the surface of *Staph. carnosus* cells. In the case of one of these proteins, intranasal immunizations with live recombinant *Staph. carnosus* cells expressing the chimeric protein on their surface resulted in an improved antibody response to a model immunogen present within the chimeric surface protein.

A GapC plasmin binding protein from a strain of Group A *Streptococcus* has previously been identified and characterized, and its use in thrombolytic therapies has been described (Boyle, et al., U.S. Pat. No. 5,237,050; Boyle, et al., U.S. Pat. No. 5,328,996).

However, until now, the protective capability of GapC has not been studied, nor have the GapC proteins of *Streptococcus dysgalactiae, Streptococcus agalactiae, Streptococcus uberis, Streptococcus parauberis* or *Streptococcus iniae* been isolated or characterized.

SUMMARY OF THE INVENTION

Accordingly, the present invention provides novel *Streptococcus* GapC proteins and vaccine compositions comprising the same. In one embodiment, the invention is directed to an isolated GapC protein selected from the group consisting of:

(a) an isolated GapC protein comprising the amino acid sequence shown at amino acid positions 1 to 336, inclusive, of FIGS. 1A–1B (SEQ ID NO:4);

(b) an isolated GapC protein comprising an amino acid sequence with at least 98% sequence identity to the amino acid sequence shown at amino acid positions 1 to 336, inclusive, of FIGS. 2A–2B (SEQ ID NO:6);

(c) an isolated GapC protein comprising an amino acid sequence with at least 98% sequence identity to the amino acid sequence shown at amino acid positions 1 to 336, inclusive, of FIGS. 3A–3B (SEQ ID NO:8);

(d) an isolated GapC protein comprising an amino acid sequence with at least 98% sequence identity to the amino acid sequence shown at amino acid positions 1 to 336, inclusive, of FIGS. 4A–4B (SEQ ID NO:10);

(e) an isolated GapC protein comprising an amino acid sequence with at least 98% sequence identity to the amino acid sequence shown at amino acid positions 1 to 336, inclusive, of FIGS. 5A–5B (SEQ ID NO:12); and (f) immunogenic fragments of (a), (b), (c), (d) and (e) comprising at least about 5 amino acids.

In another embodiment, the invention is directed to isolated polynucleotides comprising coding sequences for the above-described GapC proteins, or complements thereof, recombinant vectors comprising the polynucleotides, host cells comprising the recombinant vectors, and methods of recombinantly producing the GapC proteins.

In yet other embodiments, the subject invention is directed to vaccine compositions comprising a pharmaceutically acceptable vehicle and a GapC protein as described above, methods of producing the vaccine compositions, as well as methods of treating or preventing bacterial infections in a vertebrate subject comprising administering to the subject a therapeutically effective amount of the vaccine composition. The bacterial infection is, for example, a *streptococcus* infection and may cause mastitis. The vaccine compositions may further comprise an adjuvant.

In other embodiments, the invention is directed to antibodies directed against the isolated GapC proteins. The antibodies may be polyclonal or monoclonal.

In still further embodiments, the invention is directed to methods of detecting *Streptococcus* antibodies in a biological sample, comprising:

(a) reacting the biological sample with an isolated GapC protein, or an immunogenic variant or fragment thereof, under conditions which allow said *Streptococcus* antibodies, when present in the biological sample, to bind to the GapC protein, or an immunogenic variant or fragment thereof, to form an antibody/antigen complex; and (b) detecting the presence or absence of the complex, thereby detecting the presence or absence of *Streptococcus* antibodies in said sample.

In another embodiment, the invention is directed to a method of detecting a GapC protein in a biological sample, comprising:

(a) reacting the sample with antibodies directed against the GapC protein under conditions which allow the antibodies to bind to the GapC protein, when present in the sample, to form an antibody/antigen complex; and (b) detecting the presence or absence of the complex, thereby detecting the presence or absence of a GapC protein in the sample.

In another embodiment, the invention is directed to an immunodiagnostic test kit for detecting *Streptococcus* infection, the test kit comprising a GapC protein, or an immunogenic variant or fragment thereof, or antibodies directed against a GapC protein, and instructions for conducting the immunodiagnostic test.

These and other embodiments of the subject invention will readily occur to those of skill in the art in view of the disclosure herein.

BRIEF DESCRIPTION OF THE FIGURES

FIGS. 1A–1B depict the isolated nucleotide sequences and deduced amino acid sequences of the gapC gene for *S. dysgalactiae* (SEQ ID NO:3 and SEQ ID NO:4).

FIGS. 2A–2B depict the isolated nucleotide sequences and deduced amino acid sequences of the gapC gene for *S. agalactiae* (SEQ ID NO:5 and SEQ ID NO:6).

FIGS. 3A–3B depict the isolated nucleotide sequences and deduced amino acid sequences of the gapC gene for *S. uberis* (SEQ ID NO:7 and SEQ ID NO:8).

FIGS. 4A–4B depict the isolated nucleotide sequences and deduced amino acid sequences of the gapC gene for *S. parauberis* (SEQ ID NO:9 and SEQ ID NO: 10).

FIGS. 5A–5B depict the isolated nucleotide sequences and deduced amino acid sequences of the gapC gene for *S. iniae* (SEQ ID NO:11 and SEQ ID NO: 12).

FIGS. 6A–6E (SEQ ID NOs:3, 5, 7, 9, 11, 13, 15 and 17) show a DNA alignment created by PileUp and displayed by Pretty software (a component of the GCG Wisconsin Package, version 10, provided by the SeqWeb sequence analysis package, version 1.1, of the Canadian Bioinformatics Resource). The figure depicts the isolated nucleotide sequences of the gapC genes from *S. dysgalactiae* (DysGapC, Check 9344), *S. agalactiae* (AgalGapC. Check 2895), *S. uberis* (UberGapC, Check 5966), *S. parauberis* (ParaUbGapC, Check 9672), and *S. iniae* (SiniGapC, Check 990). The previously known sequences of *S. equisimilis* (SeqGapC, Check 5841), *S. pyogenes* (SpyGapC, Check 4037), and a bovine GAPDH protein (BovGapC, check 5059) are also included. The length and weight parameters were the same for all sequences (1018 and 1.00, respectively). The parameters used in the DNA sequence comparison were as follows: Plurality—2.00; Threshold—1; AveWeight—1.00; AveMatch—1.00; AvMisMatch—0.00; Symbol comparison table—pileupdna.cmp; CompCheck—6876; GapWeight—5; GapLengthWeight—1; PileUp MSF—1018; Type—N; Check—3804. In the figure, dashes represent identical nucleotides; dots represent gaps introduced by the software used to generate the alignment chart, and tildes represent regions not included in the overall alignment due to differences in the length of the gene sequences.

FIGS. 7A–7B (SEQ ID NOs:4, 6, 8, 10, 12, 14, 16 and 18) show an amino acid sequence alignment created by PileUp and displayed by Pretty (as above) that depicts the deduced amino acid sequences of the GapC proteins from *S. dysgalactiae* (DysGapC, Check 6731), *S. agalactiae* (AgalGapC, Check 1229), *S. uberis* (UberGapC, Check 8229), *S. parauberis* (PUberGapC, Check 8889) and *S. iniae* (IniaeGapC, check 8785). The previously known sequences of *S. equisimilis* (SeqGapC, Check 8252), *S. pyogenes* (SpyGapC, Check 6626) and a bovine GAPDH protein (BovGapC, Check 8479) are also included. In the figure, dashes represent identical amino acid residues; dots represent gaps introduced by the PileUp software, and tildes represent regions not included in the overall alignment due to differences in the length of the gene sequences.

DETAILED DESCRIPTION OF THE INVENTION

Figure 8:
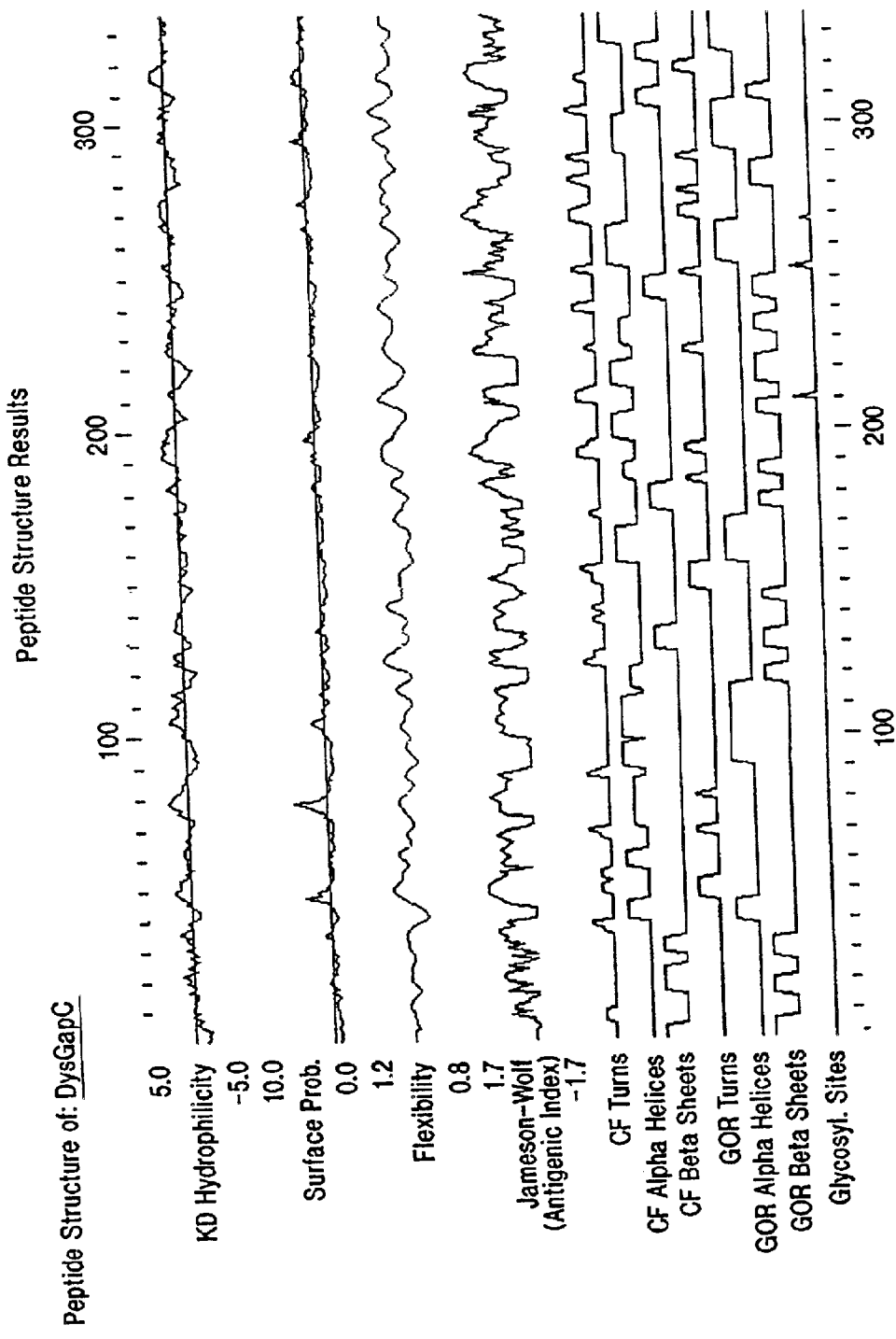
FIG. 8 shows Kyte-Doolittle hydropathy plots (averaged over a window of 7), Emini surface probability plots, Karplus-Schulz chain flexibility plots, Jameson-Wolf antigenic index plots, and both Chou-Fasman and Garnier-Osguthorpe-Robson secondary structure plots for the GapC protein isolated from *S. dysgalactiae*.
Figure 9:
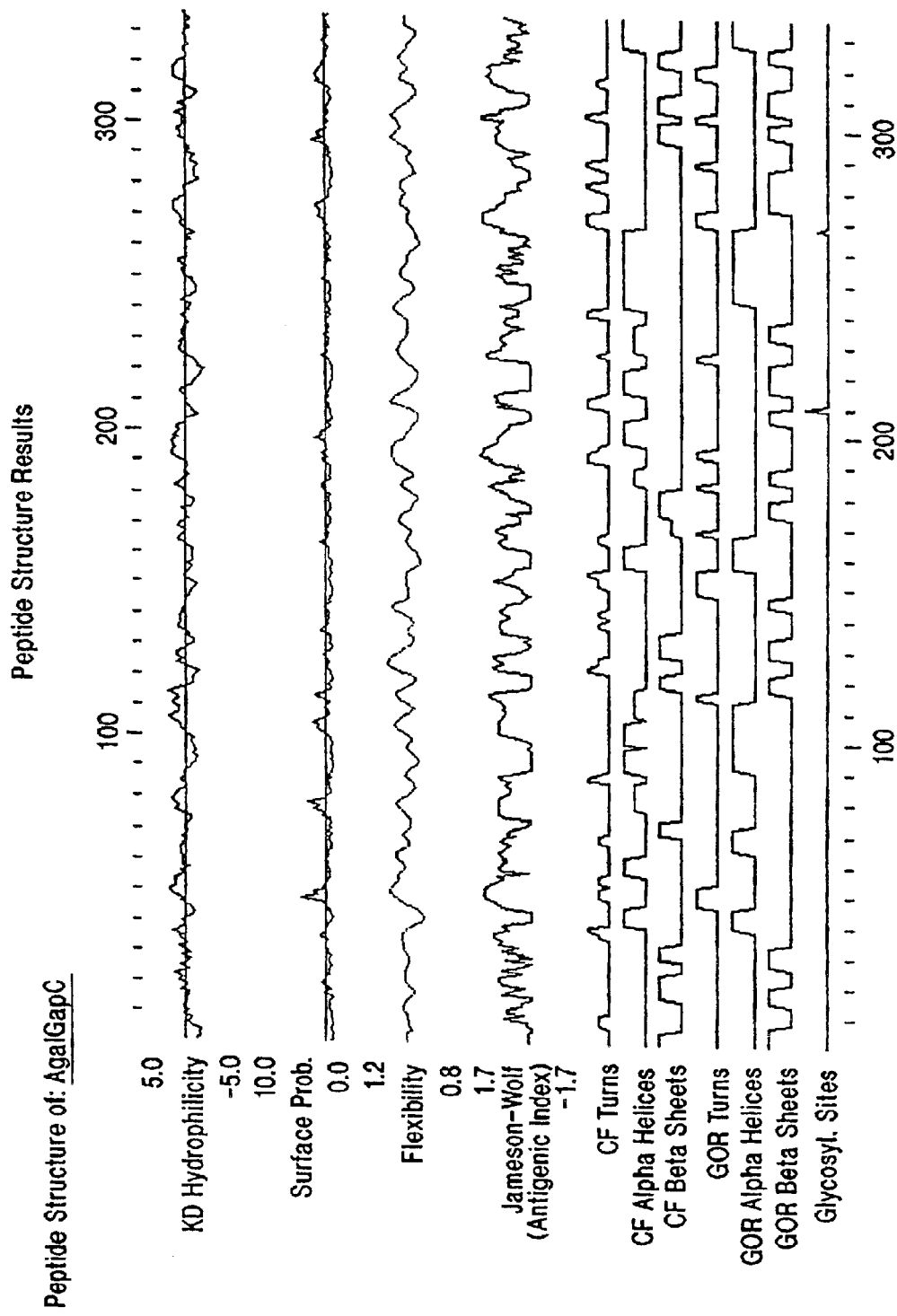
FIG. 9 shows Kyte-Doolittle hydropathy plots (averaged over a window of 7), Emini surface probability plots, Karplus-Schulz chain flexibility plots, Jameson-Wolf antigenic index plots, and both Chou-Fasman and Garnier-Osguthorpe-Robson secondary structure plots for the GapC protein isolated from *S. agalactiae*.
Figure 10:
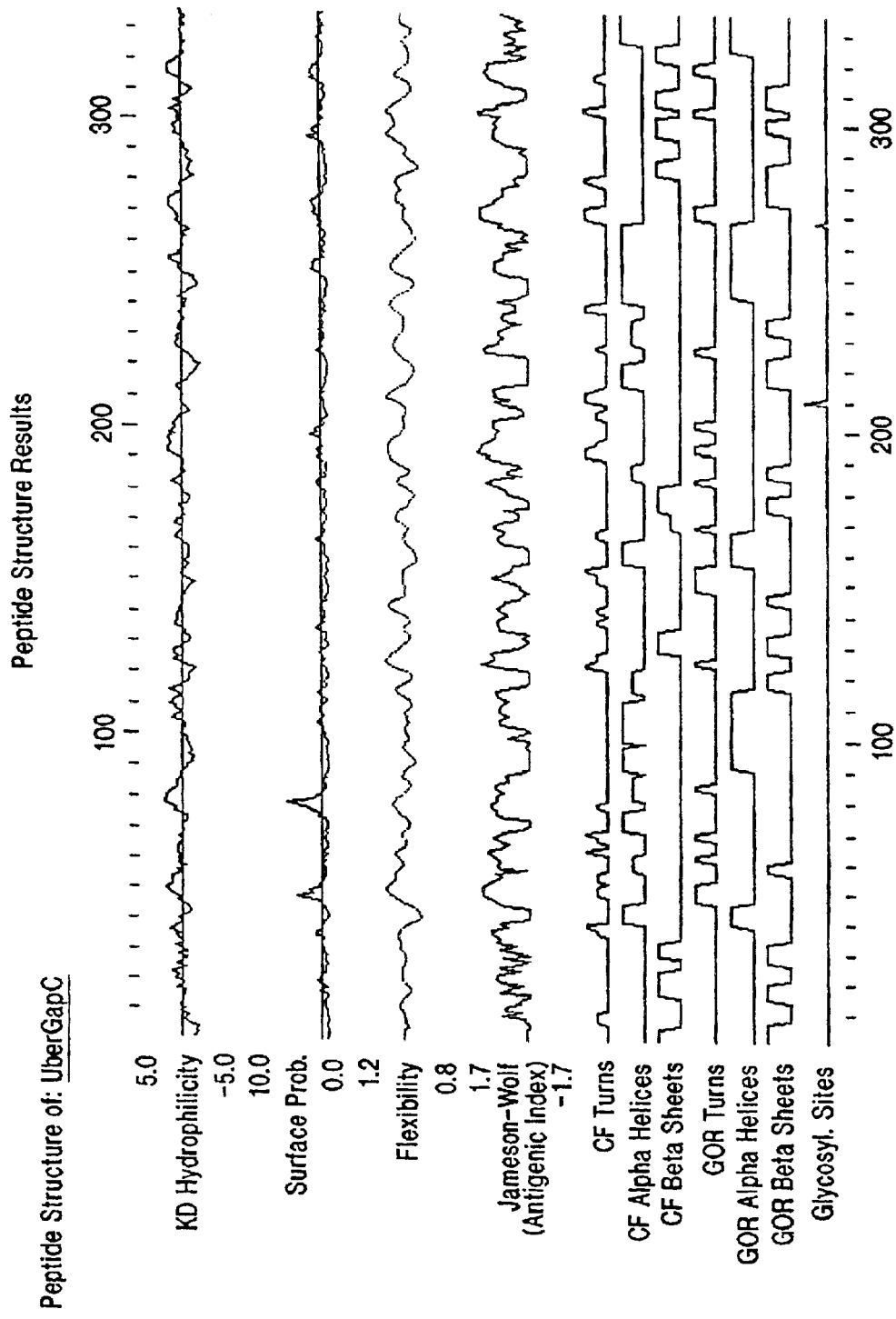
FIG. 10 shows Kyte-Doolittle hydropathy plots (averaged over a window of 7), Emini surface probability plots, Karplus-Schulz chain flexibility plots, Jameson-Wolf antigenic index plots, and both Chou-Fasman and Garnier-Osguthorpe-Robson secondary structure plots for the GapC protein isolated from *S. uberis*.
Figure 11:
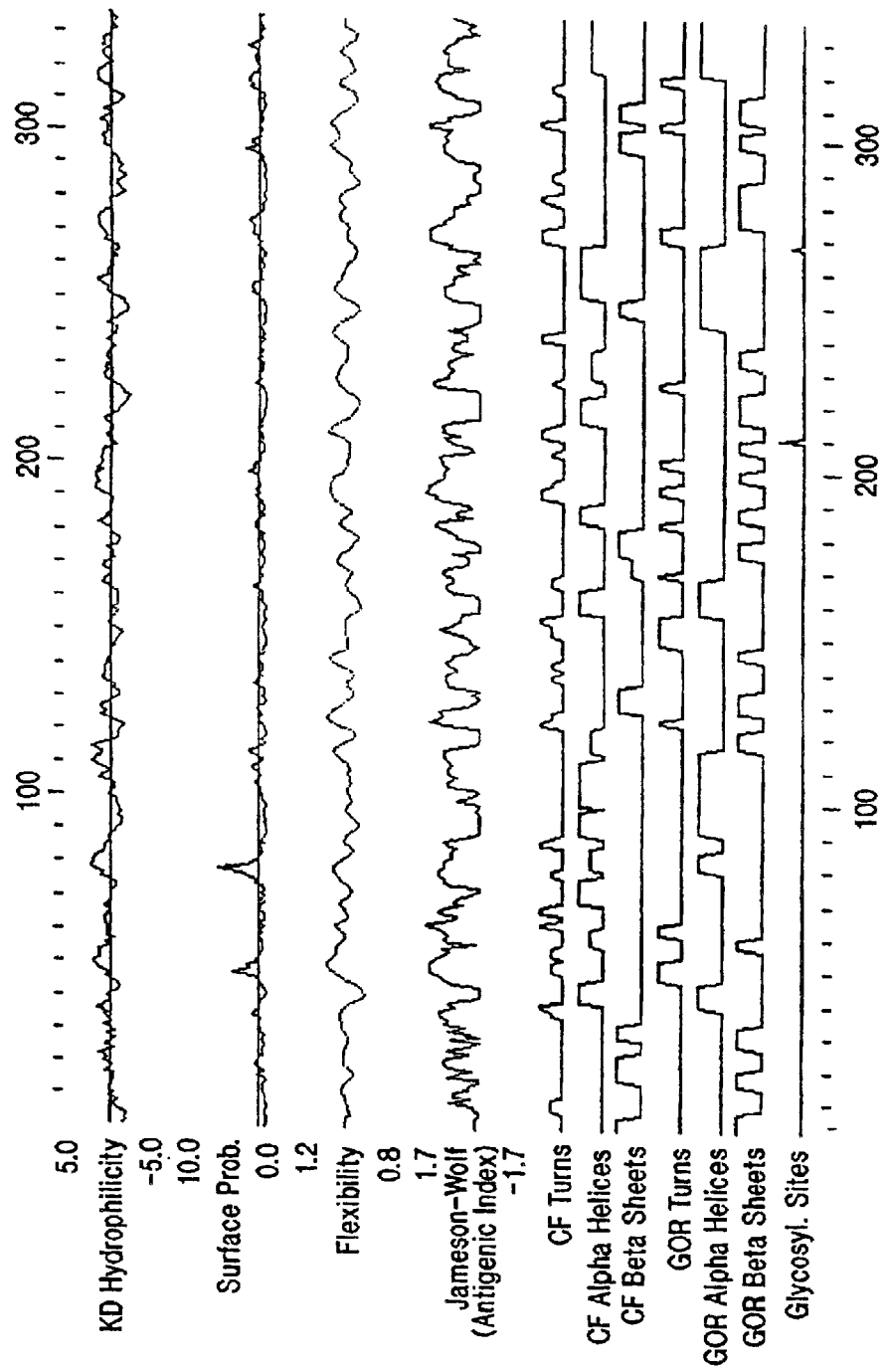
FIG. 11 shows Kyte-Doolittle hydropathy plots (averaged over a window of 7), Emini surface probability plots, Karplus-Schulz chain flexibility plots, Jameson-Wolf antigenic index plots, and both Chou-Fasman and Garnier-Osguthorpe-Robson secondary structure plots for the GapC protein isolated from *S. parauberis*.
Figure 12:
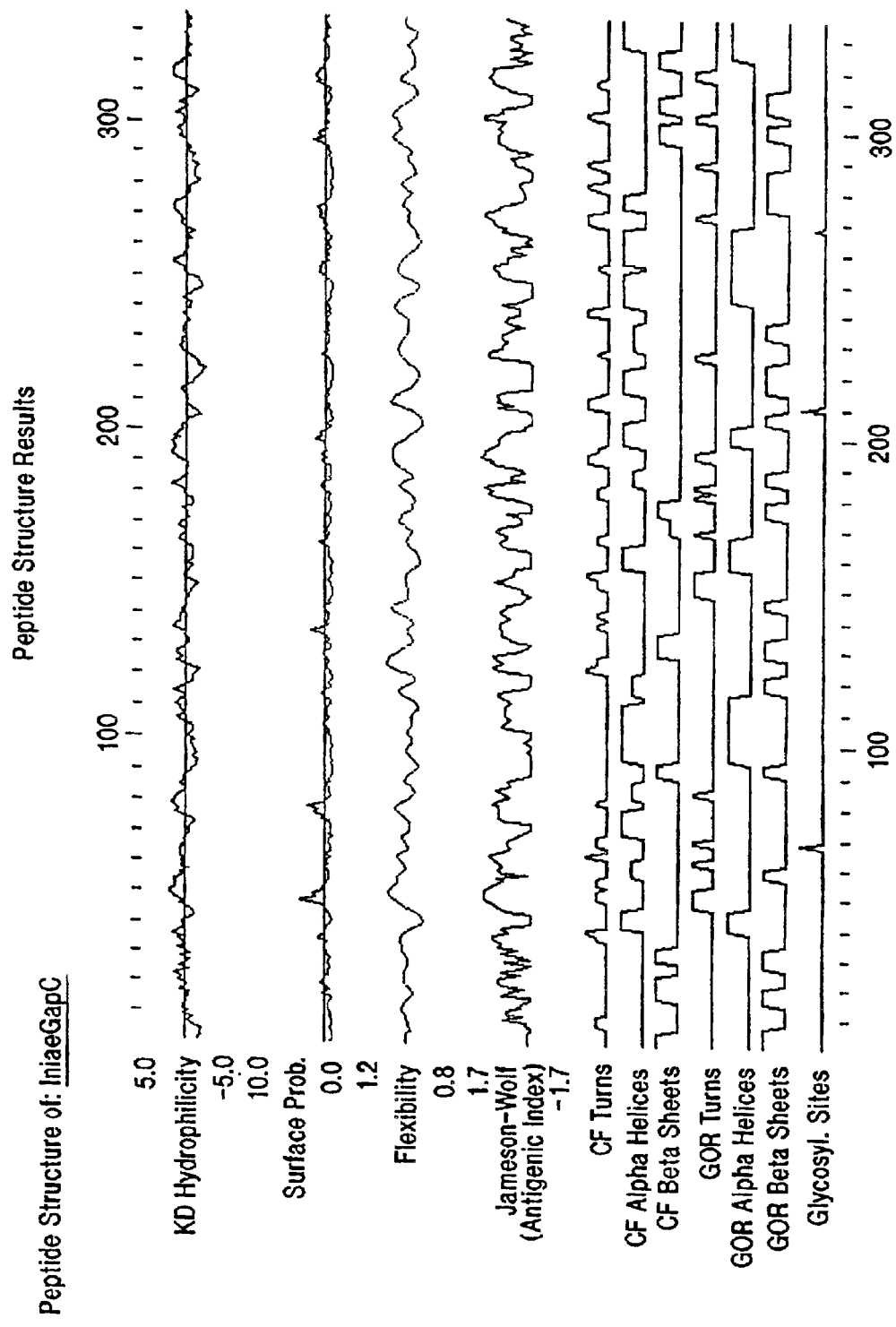
FIG. 12 shows Kyte-Doolittle hydropathy plots (averaged over a window of 7), Emini surface probability plots, Karplus-Schulz chain flexibility plots, Jameson-Wolf antigenic index plots, and both Chou-Fasman and Garnier-Osguthorpe-Robson secondary structure plots for the GapC protein isolated from *S. iniae*.
Figure 13:
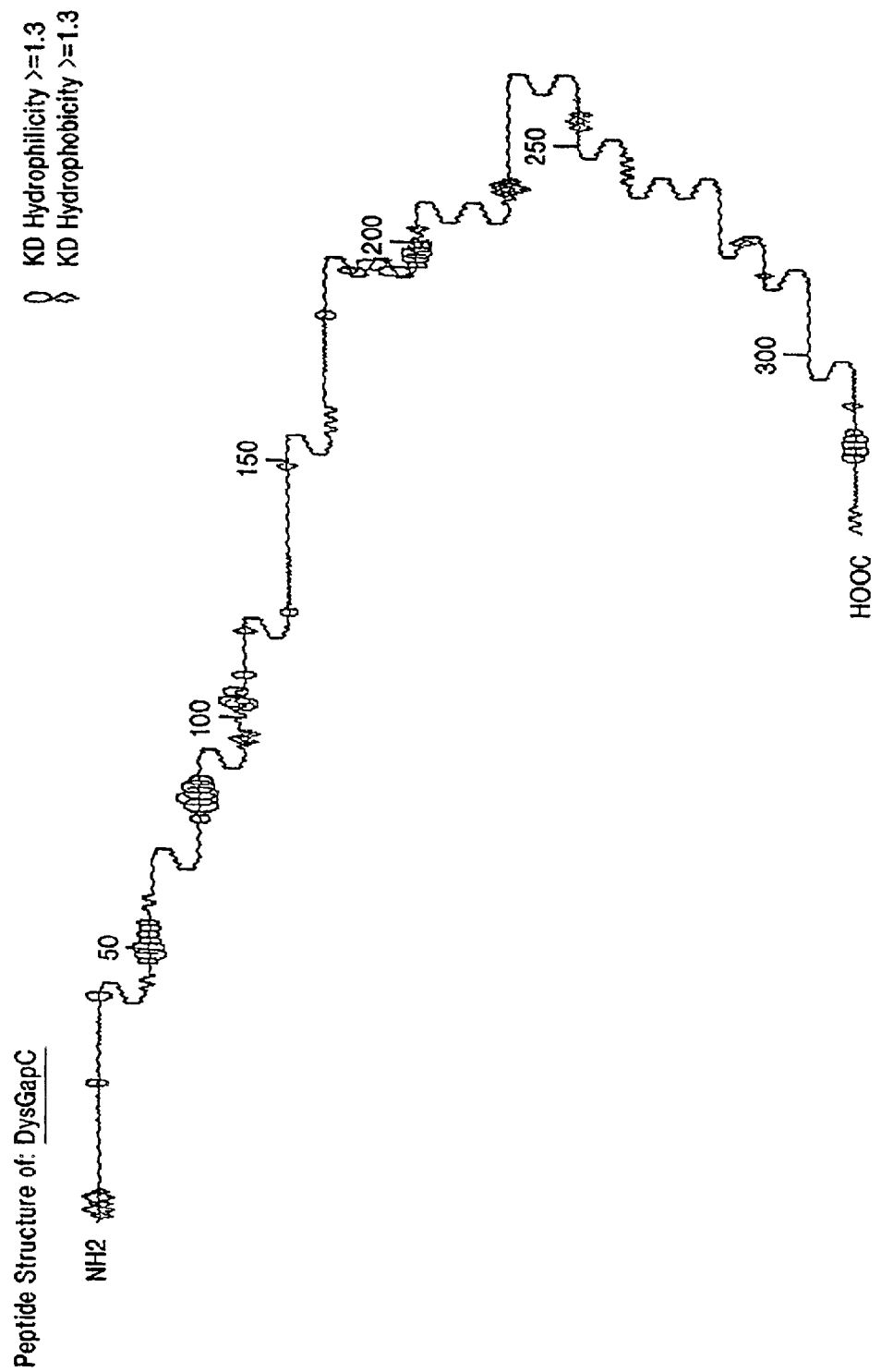
FIG. 13 is a diagrammatic representation of the Chou-Fasman secondary structure plots for the GapC protein isolated from *S. dysgal*.
Figure 14:
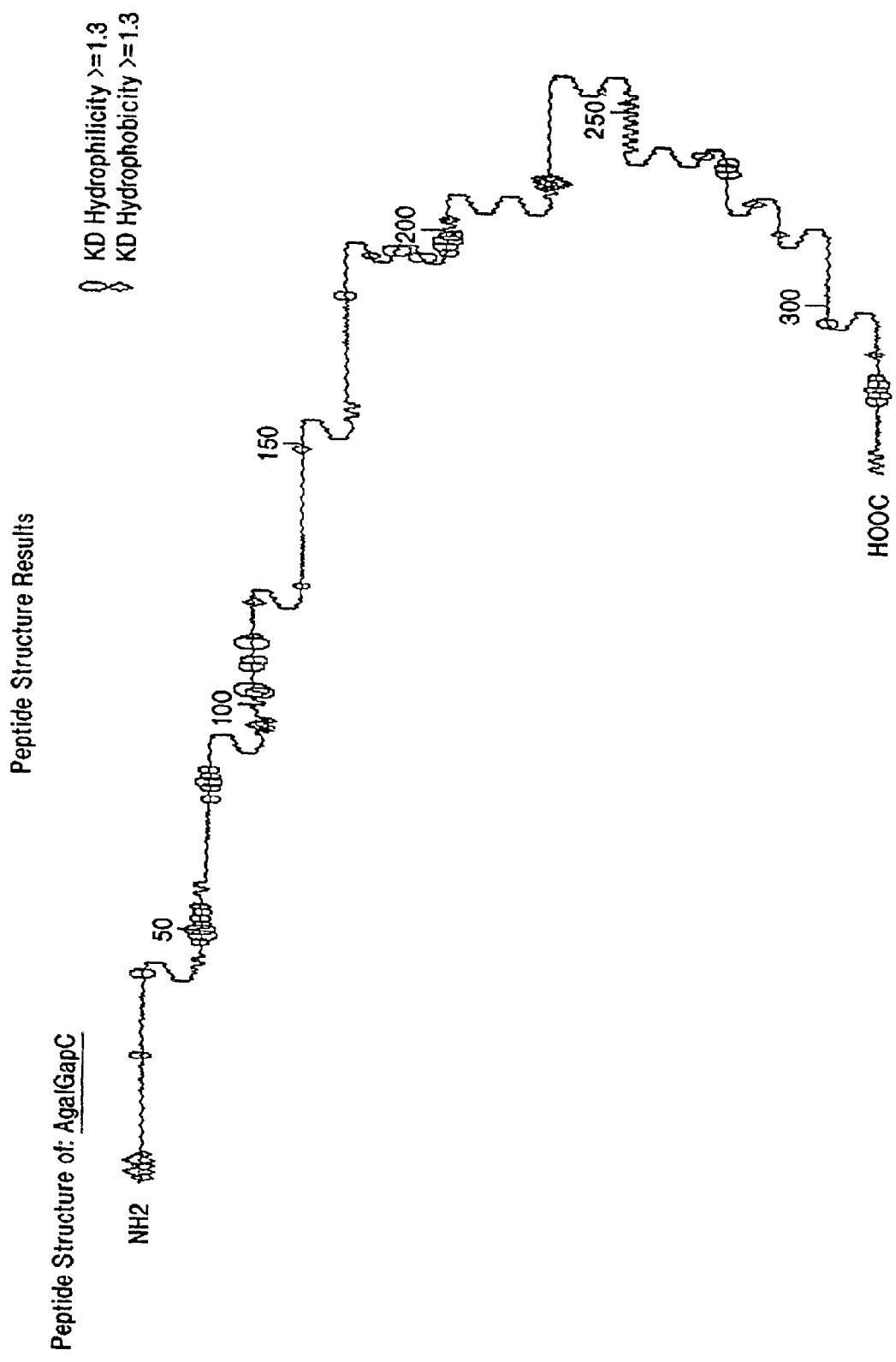
FIG. 14 is a diagrammatic representation of the Chou-Fasman secondary structure plots for the GapC protein isolated from *S. agalactiae*.
Figure 15:
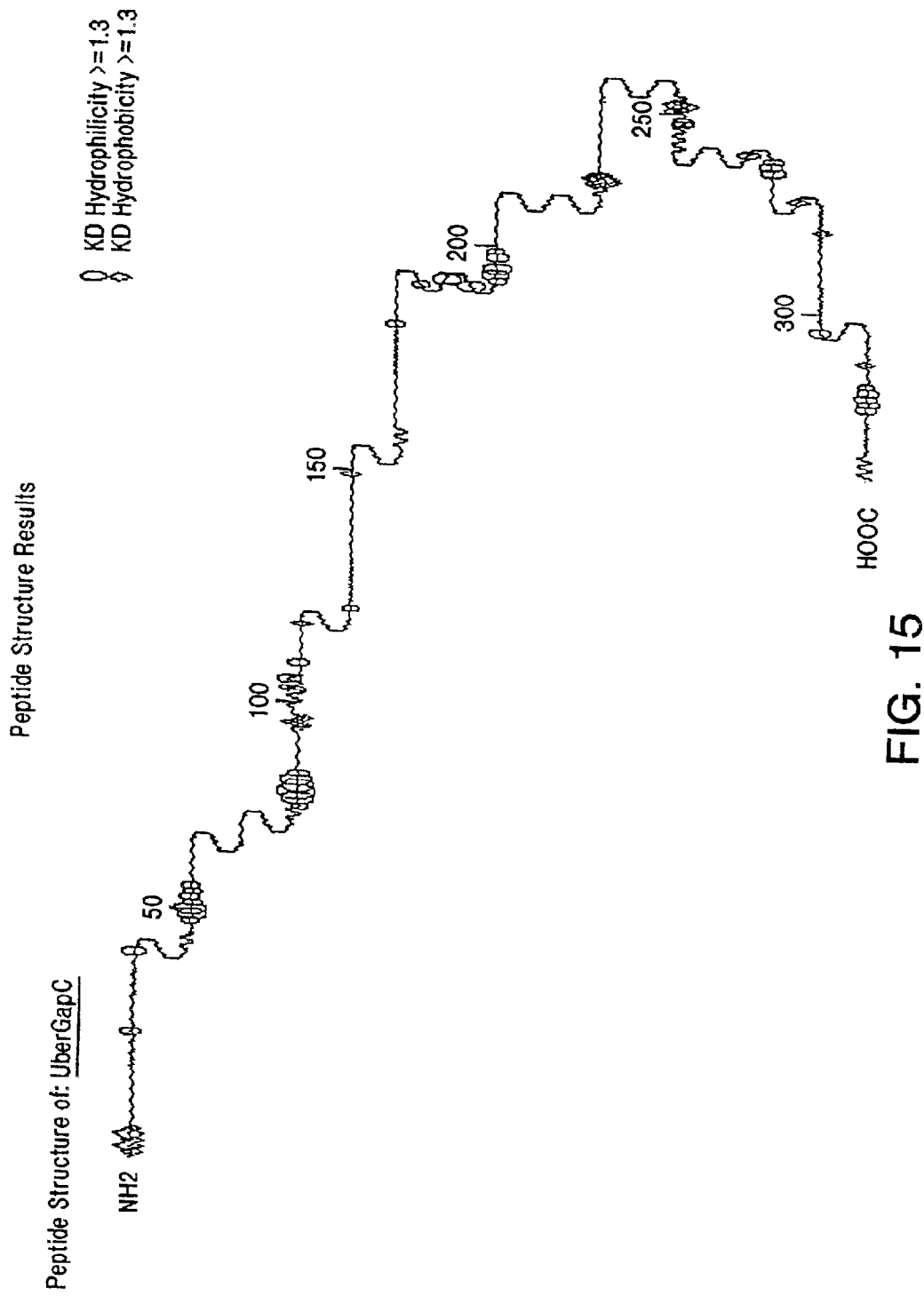
FIG. 15 is a diagrammatic representation of the Chou-Fasman secondary structure plots for the GapC protein isolated from *S. uberis*.
Figure 16:
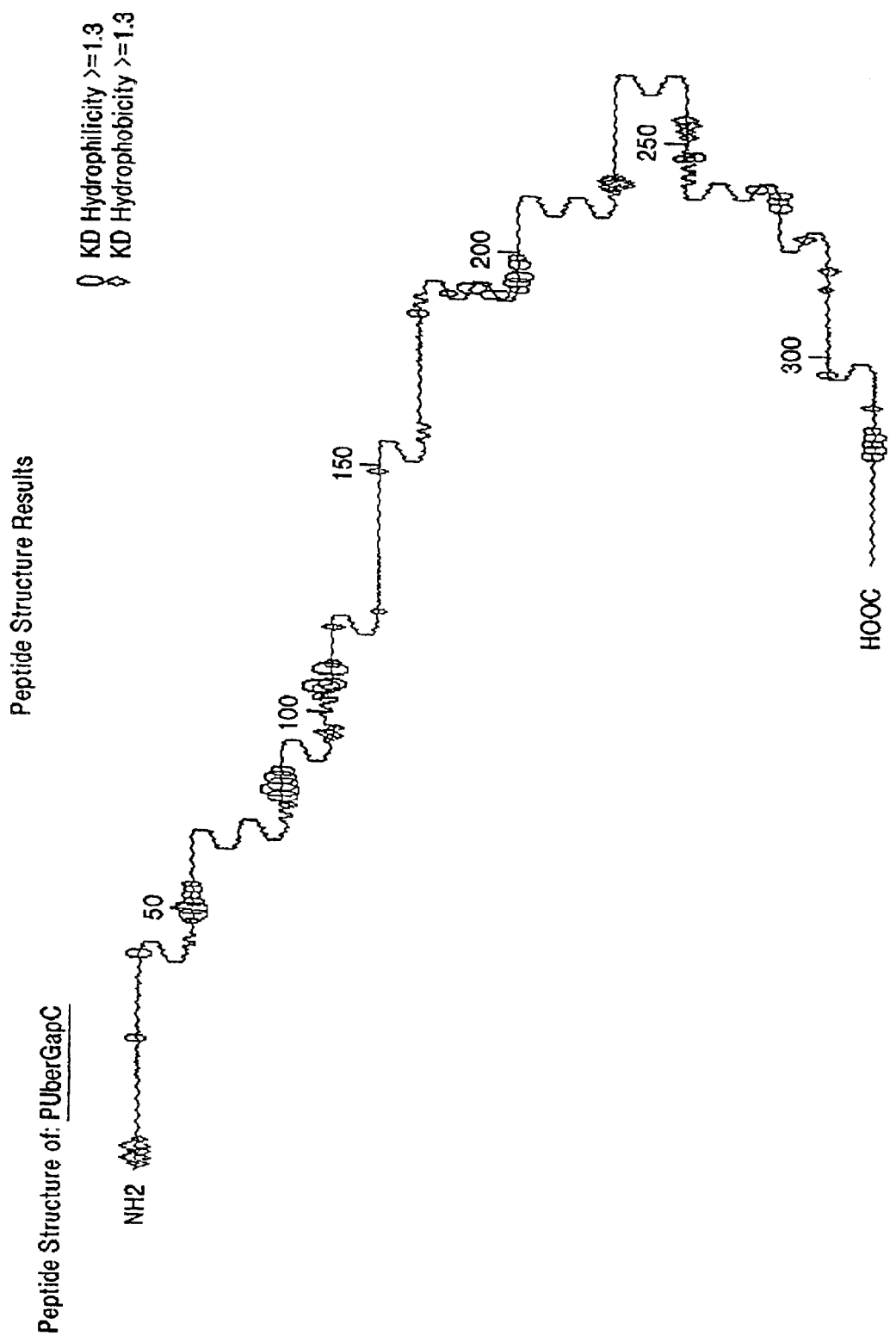
FIG. 16 is a diagrammatic representation of the Chou-Fasman secondary structure plots for the GapC protein isolated from *S. parauberis*.
Figure 17:
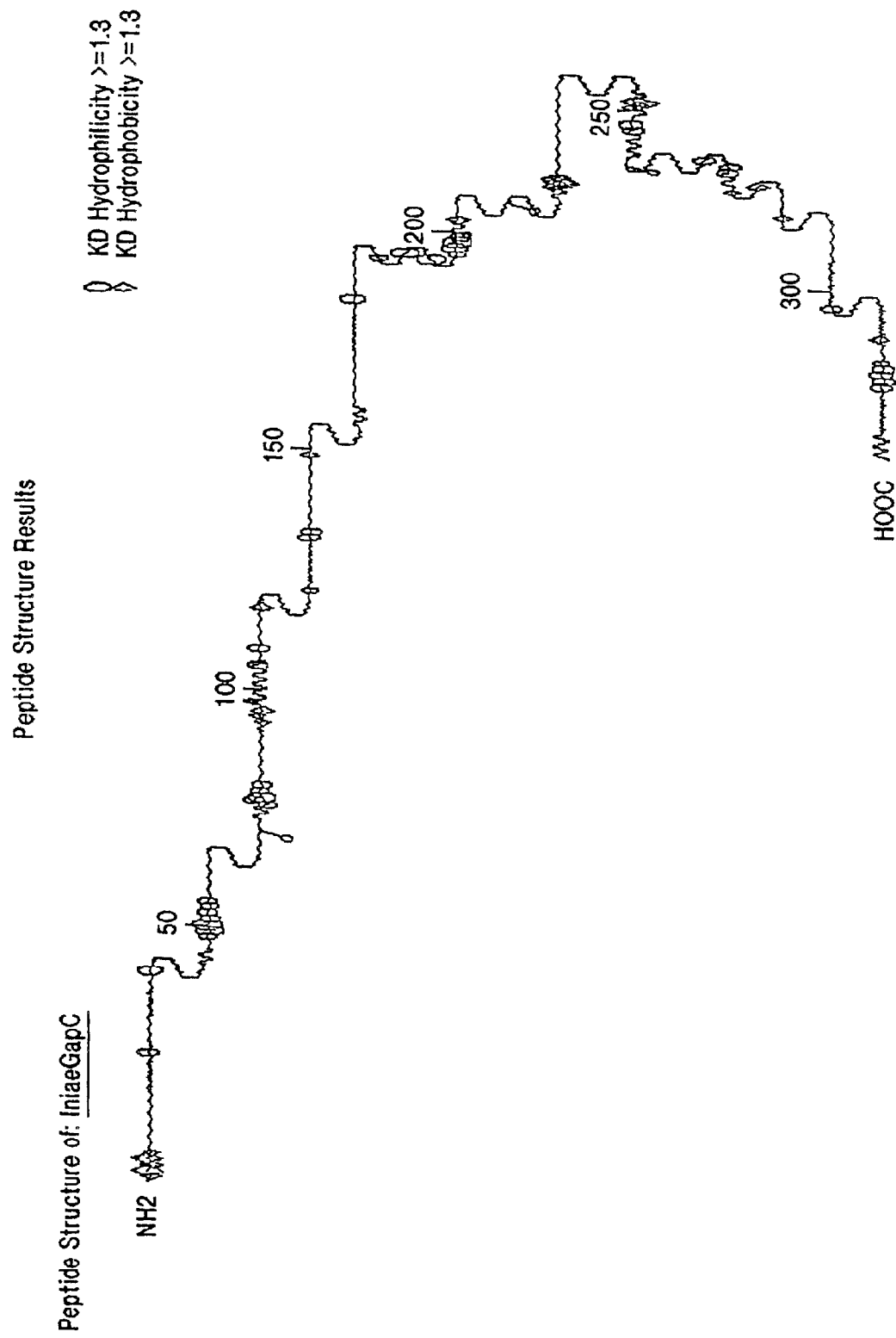
FIG. 17 is a diagrammatic representation of the Chou-Fasman secondary structure plots for the GapC protein isolated from *S. iniae*.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook, Fritsch & Maniatis, *Molecular Cloning: A Laboratory Manual*, Vols. I, II and III, Second Edition (1989); Perbal, B., *A Practical Guide to Molecular Cloning* (1984); the series, *Methods In Enzymology* (S. Colowick and N. Kaplan eds., Academic Press, Inc.); and *Handbook of Experimental Immunology*, Vols. I–IV (D. M. Weir and C. C. Blackwell eds., 1986, Blackwell Scientific Publications).

All publications, patents and patent applications cited herein, whether supra or infra, are hereby incorporated by reference in their entirety.

The following amino acid abbreviations are used throughout the text:

| | |
|---|---|
| Alanine: Ala (A) | Arginine: Arg (R) |
| Asparagine: Asn (N) | Aspartic acid: Asp (D) |
| Cysteine: Cys (C) | Glutamine: Gin (Q) |
| Glutamic acid: Glu (E) | Glycine: Gly (G) |
| Histidine: His (H) | Isoleucine: Ile (I) |
| Leucine: Leu (L) | Lysine: Lys (K) |
| Methionine: Met (M) | Phenylalanine: Phe (F) |
| Proline: Pro (P) | Serine: Ser (S) |
| Threonine: Thr (T) | Tryptophan: Trp (W) |
| Tyrosine: Tyr (Y) | Valine: Val (V) |

1. Definitions

In describing the present invention, the following terms will be employed, and are intended to be defined as indicated below.

It must be noted that, as used in this specification and the appended claims, the singular forms "a", "an" and "the" include plural referents unless the content clearly dictates otherwise. Thus, for example, reference to "a *Streptococcus* GapC protein" includes a mixture of two or more such proteins, and the like.

The terms "GapC protein" and "GapC plasmin binding protein" (used interchangeably herein) or a nucleotide sequence encoding the same, intends a protein or a nucleotide sequence, respectively, which is derived from a GapC gene found in a variety of *Streptococcus* species, including, without limitation certain strains of group A streptococci (Lottenbery, R., et al., (1987) *Infect. Immun*.55:1914–1918). The nucleotide sequence of representative *Streptococcus* gapC genes, and the corresponding amino acid sequence of the GapC proteins encoded by these genes, are depicted in the Figures. In particular, FIGS. 1 through 5 depict the isolated nucleotide sequences and isolated amino acid sequences of *S. dysgalactiae* (SEQ ID NO:3 and SEQ ID NO:4, respectively), *S. agalactiae* (SEQ ID NO:5 and SEQ ID NO:6, respectively), *S. uberis* (SEQ ID NO:7 and SEQ ID NO:8, respectively), *S. parauberis* (SEQ ID NO:9 and SEQ ID NO:10, respectively), and *S. iniae* (SEQ ID NO:11 and SEQ ID NO:12, respectively). The nucleotide sequences of the S. uberis and S. agalactiae gapC genes have been submitted to GenBank under the accession numbers AF421899 and AF421900, respectively.

However, a GapC protein as defined herein is not limited to the depicted sequences as subtypes of each of these Streptococcus species are known and variations in GapC proteins will occur between them.

Representative gapC genes, derived from S. dysgalactiae, S. agalactiae, S. uberis, and S. parauberis, are found in the plasmids pET15bgapC (ATCC No. PTA-1976), pMF521c (ATCC No. PTA-1975), pMF521a (ATCC No. PTA-1973), pMF521d, and pMF521e (ATCC No. PTA-1972), respectively.

Furthermore, the derived protein or nucleotide sequences need not be physically derived from the gene described above, but may be generated in any manner, including for example, chemical synthesis, isolation (e.g., from S. dysgalactiae) or by recombinant production, based on the information provided herein.

The terms also include proteins possessing, as well as lacking, a signal sequence, if such is present, as well as proteins in neutral form or in the form of basic or acid addition salts depending on the mode of preparation. Such acid addition salts may involve free amino groups and basic salts may be formed with free carboxyls. Pharmaceutically acceptable basic and acid addition salts are discussed further below. In addition, the proteins may be modified by combination with other biological materials such as lipids (both those occurring naturally with the molecule or other lipids that do not destroy immunological activity) and saccharides, or by side chain modification, such as acetylation of amino groups, phosphorylation of hydroxyl side chains, oxidation of sulfhydryl groups, glycosylation of amino acid residues, as well as other modifications of the encoded primary sequence.

The term "streptococcal GapC protein" intends a GapC plasmin-binding protein, as defined above, derived from a streptococcal species that produces the same, including, but not limited to S. dysgalactiae, S. agalactiae, S. uberis, S. parauberis, and S. iniae. For example, a "S. dysgalactiae GapC protein" is a GapC plasmin-binding protein as defined above, derived from S. dysgalactiae. Similarly, an "S. agalactiae GapC protein" intends a gapC binding protein derived from S. agalactiae.

The terms "variant" and "mutein" of a GapC protein refer to biologically active derivatives of a GapC protein, as defined above, or fragments of such derivatives, that retain immunological and/or plasmin-binding activity. The term "mutein" refers to peptides having one or more peptide mimics ("peptoids"), such as those described in International Publication No. WO 91/04282. Preferably, the variant or mutein has at least the same activity as the native molecule. Methods for making polypeptide variants and muteins are known in the art and are described further below.

In general, the term "variant" refers to compounds having a native polypeptide sequence and structure with one or more amino acid additions, substitutions (generally conservative in nature) and/or deletions, relative to the native molecule, so long as the modifications do not destroy activity. Thus, a "variant" of a GapC protein includes a protein with amino acid sequences substantially homologous (as defined below) to contiguous amino acid sequences encoded by the above GapC genes, which display immunological and/or plasmin-binding activity. Particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. For example, it is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule, but possessing minor amino acid substitutions that do not substantially affect the immunogenicity and/or plasmin-binding affinity of the protein, are therefore within the definition of the reference polypeptide.

Other substitutions include substitutions of naturally occurring amino acids with amino acid analogs. Such amino acid analogs are well known and include, but are not limited to, 2-aminoadipic acid, 3-aminoadipic acid, beta-alanine, beta-aminopropionic acid, 2-aminobutyric acid, 4-aminobutyric acid, piperidinic acid, 6-aminocaproic acid, 2-aminoheptanoic acid, 2-aminoisobutyric acid, 3-aminoisobutyric acid, 2-aminopimelic acid, 2,4-diaminobutyric acid, desmosine, 2,2'-diaminopimelic acid, 2,3-diaminopropionic acid, N-ethylglycine, N-ethylasparagine, hydroxylysine, allo-hydroxylysine, 3-hydroxyproline, 4-hydroxyproline, isodesmosine, allo-isoleucine, N-methylglycine, sarcosine, N-methylisoleucine, 6-N-methyllysine, N-methylvaline, norvaline, norleucine and ornithine.

For example, the polypeptide of interest may include up to about 5–10 conservative or non-conservative amino acid substitutions, or even up to about 15–25 or 20–50 conservative or non-conservative amino acid substitutions, or any integer between these values, so long as the desired function of the molecule remains intact.

In this regard, GapC proteins isolated from streptococci exhibit several variable regions in their amino acid sequences, located at amino acid positions 62 to 81; 102 to 112; 165 to 172; 248 to 271; and 286 to 305, numbered relative to the amino acid sequences depicted in FIGS. 1–5. These regions, which in S. dysgalactiae, S. agalactiae, S. uberis, S. parauberis and S. iniae exhibit from 1 to 9 amino acid substitutions, are expected to be amenable to variation without substantially affecting immunogenic or enzymatic function.

Similarly, substitutions occurring in the transmembrane binding domain, if present, and the signal sequence, if present, normally will not affect immunogenicity. One of skill in the art may readily determine other regions of the molecule of interest that can tolerate change by reference to the protein structure data shown in FIGS. 8–17 herein.

By "fragment" is intended a polypeptide or polynucleotide consisting of only a part of the intact polypeptide sequence and structure, or the nucleotide sequence and structure, of the reference gene. The polypeptide fragment can include a C-terminal deletion and/or N-terminal deletion of the native polypeptide, or can be derived from an internal portion of the molecule. Similarly, a polynucleotide fragment can include a 3' and/or a 5' deletion of the native polynucleotide, or can be derived from an internal portion of the molecule. A polypeptide "fragment" of a GapC protein will generally include at least about 5 contiguous amino acid residues, preferably at least about 10 contiguous amino acid residues of the full-length molecule, preferably at least about 15–25 contiguous amino acid residues of the full-length molecule, and most preferably at least about 20–50 or more contiguous amino acid residues of full-length molecule, or any integer between 5 amino acids and the full-length sequence, provided that the fragment in question retains GapC activity as described above.

A nucleotide fragment of the gene of interest generally includes at least about 8 contiguous base pairs, more preferably at least about 10–20 contiguous base pairs, and most preferably at least about 25–50, or more, contiguous base pairs of the gene, or any integers between these values. Such fragments are useful as probes and in diagnostic methods, discussed more filly below.

Additionally, polypeptide fragments include forms of the GapC proteins which lack a membrane anchor region, if present in the reference protein, and nucleic acid sequences encoding proteins with such deletions. Such deletions may be desirable in systems that do not provide for secretion of the protein.

Furthermore, the plasmin-binding domains of the proteins, may or may not be present. Thus, for example, if the GapC plasmin-binding protein will be used to purify plasmin, the plasmin-binding domain will generally be retained. If the protein is to be used in vaccine compositions, immunogenic epitopes which may or may not include the plasmin-binding domain, will be present.

An "isolated" protein or polypeptide is a protein or polypeptide molecule separate and discrete from the whole organism with which the molecule is found in nature; or a protein or polypeptide devoid, in whole or part, of sequences normally associated with it in nature; or a sequence, as it exists in nature, but having heterologous sequences (as defined below) in association therewith.

The term "functionally equivalent" intends that the amino acid sequence of a GapC plasmin-binding protein is one that will elicit a substantially equivalent or enhanced immunological response, as defined herein, if the protein is to be used in a vaccine, or that will function in an equivalent or enhanced manner in an immunoassay, as compared to the activity of a GapC plasmin-binding protein having identity with the reference GapC plasmin-binding protein, or an immunogenic portion thereof.

The term "epitope" refers to the site on an antigen or hapten to which specific B cells and/or T cells respond. The term is also used interchangeably with "antigenic determinant" or "antigenic determinant site." Antibodies that recognize the same epitope can be identified in a simple immunoassay showing the ability of one antibody to block the binding of another antibody to a target antigen.

The terms "immunogenic" protein or polypeptide refer to an amino acid sequence which elicits an immunological response as described herein. An "immunogenic" protein or polypeptide, as used herein, includes the full-length sequence of the GapC plasmin-binding protein in question, with or without the signal sequence, membrane anchor domain and/or plasmin-binding domain, analogs thereof, or immunogenic fragments thereof By "immunogenic fragment" is meant a fragment of a GapC plasmin-binding protein which includes one or more epitopes and thus elicits the immunological response described herein. Such fragments can be identified using any number of epitope mapping techniques, well known in the art. See, e.g., *Epitope Mapping Protocols* in *Methods in Molecular Biology*, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) *Proc. Natl. Acad. Sci. USA* 81:3998–4002; Geysen et al. (1986) *Molec. Immunol.* 23:709–715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., *Epitope Mapping Protocols*, supra. Antigenic regions of proteins can also be identified using standard antigenicity and hydropathy plots, such as those calculated using, e.g., the Omiga version 1.0 software program available from the Oxford Molecular Group. This computer program employs the Hopp/Woods method, Hopp et al., *Proc. Natl. Acad. Sci USA* (1981) 78:3824–3828 for determining antigenicity profiles, and the Kyte-Doolittle technique, Kyte et al., *J. Mol. Biol.* (1982) 157:105–132 for hydropathy plots. FIGS. 8 to 12 herein depict Kyte-Doolittle profiles for representative proteins encompassed by the invention.

Immunogenic fragments, for purposes of the present invention, will usually include at least about 3 amino acids, preferably at least about 5 amino acids, more preferably at least about 10–15 amino acids, and most preferably 25 or more amino acids, of the parent GapC plasmin-binding-binding protein molecule. There is no critical upper limit to the length of the fragment, which may comprise nearly the full-length of the protein sequence, or even a fusion protein comprising two or more epitopes of GapC.

An "immunogenic composition" is a composition that comprises an antigenic molecule where administration of the composition to a subject results in the development in the subject of a humoral and/or a cellular immune response to the antigenic molecule of interest.

By "subunit vaccine composition" is meant a composition containing at least one immunogenic polypeptide, but not all antigens, derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

By "pharmaceutically acceptable" or "pharmacologically acceptable" is meant a material which is not biologically or otherwise undesirable, i.e., the material may be administered to an individual in a formulation or composition without causing any undesirable biological effects or interacting in a deleterious manner with any of the components of the composition in which it is contained.

An "immunological response" to a composition or vaccine is the development in the host of a cellular and/ or antibody-mediated immune response to the composition or vaccine of interest. Usually, an "immunological response" includes but is not limited to one or more of the following effects: the production of antibodies, B cells, helper T cells, suppressor T cells, and/or cytotoxic T cells and/or γδ T cells, directed specifically to an antigen or antigens included in the composition or vaccine of interest. Preferably, the host will display either a therapeutic or protective immunological response such that resistance of the mammary gland to new infection will be enhanced and/or the clinical severity of the disease reduced. Such protection will be demonstrated by either a reduction or lack of symptoms normally displayed by an infected host and/or a quicker recovery time.

By "nucleic acid immunization" is meant the introduction of a nucleic acid molecule encoding one or more selected antigens into a host cell, for the in vivo expression of an antigen, antigens, an epitope, or epitopes. The nucleic acid molecule can be introduced directly into a recipient subject, such as by injection, inhalation, oral, intranasal and mucosal administration, or the like, or can be introduced ex vivo, into cells which have been removed from the host. In the latter case, the transformed cells are reintroduced into the subject where an immune response can be mounted against the antigen encoded by the nucleic acid molecule.

The term "treatment" as used herein refers to either (1) the prevention of infection or reinfection (prophylaxis), or (2) the reduction or elimination of symptoms of the disease of interest (therapy).

By "mastitis" is meant an inflammation of the mammary gland in mammals, including in cows, ewes, goats, sows, mares, and the like, caused by the presence of S. uberis. The infection manifests itself by the infiltration of phagocytic cells in the gland. Generally, 4 clinical types of mastitis are recognized: (1) peracute, associated with swelling, heat, pain, and abnormal secretion in the gland and accompanied by fever and other signs of systemic disturbance, such as marked depression, rapid weak pulse, sunken eyes, weakness and complete anorexia; (2) acute, with changes in the gland similar to those above but where fever, anorexia and depression are slight to moderate; (3) subacute, where no systemic changes are displayed and the changes in the gland and its secretion are less marked: and (4) subclinical, where the inflammatory reaction is detectable only by standard tests for mastitis.

Standard tests for the detection of mastitis include but are not limited to, the California Mastitis Test, the Wisconsin Mastitis Test, the Nagase test, the electronic cell count and somatic cell counts used to detect a persistently high white blood cell content in milk. In general, a somatic cell count of about 300,000 to about 500,000 cells per ml or higher, in milk will indicate the presence of infection. Thus, a vaccine is considered effective in the treatment and/or prevention of mastitis when, for example, the somatic cell count in milk is retained below about 500,000 cells per ml. For a discussion of mastitis and the diagnosis thereof, see, e.g., *The Merck Veterinary Manual: A Handbook of Diagnosis, Therapy, and Disease Prevention and Control for the Veterinarian*, Merck and Co., Rahway, N.J., 1991.

By the terms "vertebrate," "subject," and "vertebrate subject" are meant any member of the subphylum Chordata, including, without limitation, mammals such as cattle, sheep, pigs, goats, horses, and humans; domestic animals such as dogs and cats; and birds, including domestic, wild and game birds such as cocks and hens including chickens, turkeys and other gallinaceous birds; and fish. The term does not denote a particular age. Thus, both adult and newborn animals, as well as fetuses, are intended to be covered.

A "nucleic acid" molecule can include, but is not limited to, procaryotic sequences, eucaryotic mRNA, cDNA from eucaryotic mRNA, genomic DNA sequences from eucaryotic (e.g., mammalian) DNA, and even synthetic DNA sequences. The term also captures sequences that include any of the known base analogs of DNA and RNA.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith. The term "isolated" in the context of a polynucleotide intends that the polynucleotide is isolated from the chromosome with which it is normally associated, and is isolated from the complete genomic sequence in which it normally occurs.

"Purified polynucleotide" refers to a polynucleotide of interest or fragment thereof which is essentially free, e.g., contains less than about 50%, preferably less than about 70%, and more preferably less than about 90%, of the protein with which the polynucleotide is naturally associated. Techniques for purifying polynucleotides of interest are well-known in the art and include, for example, disruption of the cell containing the polynucleotide with a chaotropic agent and separation of the polynucleotide(s) and proteins by ion-exchange chromatography, affinity chromatography and sedimentation according to density.

A "coding sequence" or a "nucleotide sequence encoding" a particular protein, is a nucleotide sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, procaryotic sequences, cDNA from eucaryotic mRNA, genomic DNA sequences from eucaryotic (e.g., mammalian) DNA, and even synthetic DNA sequences. A transcription termination sequence will usually be located 3' to the coding sequence. A "complementary" sequence is one in which the nitrogenous base at a given nucleotide position is the complement of the nitrogenous base appearing at the same position in the reference sequence. To illustrate, the complement of adenosine is tyrosine, and vice versa; similarly, cytosine is complementary to guanine, and vice versa; hence, the complement of the reference sequence 5'-ATGCTGA-3' would be 5'-TACGACT-3'.

A "wild-type" or "native" sequence, as used herein, refers to polypeptide encoding sequences that are essentially as they are found in nature, e.g., the *S. dysgalactiae* GapC protein encoding sequences depicted in FIGS. 1A–1B (SEQ ID NO:4).

"Recombinant" as used herein to describe a nucleic acid molecule means a polynucleotide of genomic, cDNA, semisynthetic, or synthetic origin which, by virtue of its origin or manipulation: (1) is not associated with all or a portion of the polynucleotide with which it is associated in nature; and/or (2) is linked to a polynucleotide other than that to which it is linked in nature. The term "recombinant" as used with respect to a protein or polypeptide means a polypeptide produced by expression of a recombinant polynucleotide. "Recombinant host cells," "host cells," "cells," "cell lines," "cell cultures," and other such terms denoting procaryotic microorganisms or eucaryotic cell lines cultured as unicellular entities, are used interchangeably, and refer to cells which can be, or have been, used as recipients for recombinant vectors or other transfer DNA, and include the progeny of the original cell which has been transfected. It is understood that the progeny of a single parental cell may not necessarily be completely identical in morphology or in genomic or total DNA complement to the original parent, due to accidental or deliberate mutation. Progeny of the parental cell which are sufficiently similar to the parent to be characterized by the relevant property, such as the presence of a nucleotide sequence encoding a desired peptide, are included in the progeny intended by this definition, and are covered by the above terms.

"Homology" refers to the percent similarity between two polynucleotide or two polypeptide moieties. Two DNA, or two polypeptide sequences are "substantially homologous" to each other when the sequences exhibit at least about 80%–85%, preferably at least about 90%, and most preferably at least about 95%–98% sequence similarity or identity over a defined length of the molecules. As used herein, substantially homologous also refers to sequences showing complete identity to the specified DNA or polypeptide sequence.

In general, "identity" refers to an exact nucleotide-to-nucleotide or amino acid-to-amino acid correspondence of two polynucleotides or polypeptide sequences, respectively. Percent identity can be determined by a direct comparison of the sequence information between two molecules by aligning the sequences, counting the exact number of matches between the two aligned sequences, dividing by the length of the shorter sequence, and multiplying the result by 100. Readily available computer programs can be used to aid in the analysis, such as ALIGN, Dayhoff, M. O. in *Atlas of Protein Sequence and Structure* M. O. Dayhoff ed., 5 Suppl. 3:353–358, National biomedical Research Foundation, Washington, D.C., which adapts the local homology algorithm of Smith and Waterman (1981) *Advances in Appl. Math.* 2:482–489 for peptide analysis. Programs for determining nucleotide sequence identity are available in the Wisconsin Sequence Analysis Package, Version 8 (available from Genetics Computer Group, Madison, Wis.) for example, the BESTFIT, FASTA and GAP programs, which also rely on the Smith and Waterman algorithm. These programs are readily utilized with the default parameters recommended by the manufacturer and described in the Wisconsin Sequence Analysis Package referred to above. For example, percent identity of a particular nucleotide sequence to a reference sequence can be determined using the homology algorithm of Smith and Waterman with a default scoring table and a gap penalty of six nucleotide positions.

Another method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects "sequence identity." Other suitable programs for calculating the percent identity or similarity between sequences are generally known in the art, for example, another alignment program is BLAST, used with default parameters. For example, BLASTN and BLASTP can be used using the following default parameters: genetic code=standard; filter= none; strand=both; cutoff=60; expect=10; Matrix= BLOSUM62; Descriptions=50 sequences; sort by=HIGH SCORE; Databases=non-redundant, GenBank+EMBL+ DDBJ+PDB+GenBank CDS translations+Swiss protein+ Spupdate+PIR. Details of these programs can be found at the following internet address: www.ncbi.nlm.gov/cgi-bin/ BLAST.

Alternatively, homology can be determined by hybridization of polynucleotides under conditions which form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *DNA Cloning*, supra; *Nucleic Acid Hybridization*, supra.

By the term "degenerate variant" is intended a polynucleotide containing changes in the nucleic acid sequence thereof, that encodes a polypeptide having the same amino acid sequence as the polypeptide encoded by the polynucleotide from which the degenerate variant is derived.

Techniques for determining amino acid sequence "similarity" are well known in the art. In general, "similarity" means the exact amino acid to amino acid comparison of two or more polypeptides at the appropriate place, where amino acids are identical or possess similar chemical and/or physical properties such as charge or hydrophobicity. A so-termed "percent similarity" then can be determined between the compared polypeptide sequences. Techniques for determining nucleic acid and amino acid sequence identity also are well known in the art and include determining the nucleotide sequence of the mRNA for that gene (usually via a cDNA intermediate) and determining the amino acid sequence encoded thereby, and comparing this to a second amino acid sequence. In general, "identity" refers to an exact nucleotide to nucleotide or amino acid to amino acid correspondence of two polynucleotides or polypeptide sequences, respectively.

A "heterologous" region of a DNA construct is an identifiable segment of DNA within or attached to another DNA molecule that is not found in association with the other molecule in nature. Thus, when the heterologous region encodes a bacterial gene, the gene will usually be flanked by DNA that does not flank the bacterial gene in the genome of the source bacteria. Another example of the heterologous coding sequence is a construct where the coding sequence itself is not found in nature (e.g., synthetic sequences having codons different from the native gene). Allelic variation or naturally occurring mutational events do not give rise to a heterologous region of DNA, as used herein.

A "vector" is a replicon, such as a plasmid, phage, or cosmid, to which another DNA segment may be attached so as to bring about the replication of the attached segment. A vector is capable of transferring gene sequences to target cells (e.g., bacterial plasmid vectors, viral vectors, non-viral vectors, particulate carriers, and liposomes).

Typically, the terms "vector construct," "expression vector," "gene expression vector," "gene delivery vector," "gene transfer vector," and "expression cassette" all refer to an assembly which is capable of directing the expression of a sequence or gene of interest. Thus, the terms include cloning and expression vehicles, as well as viral vectors.

These assemblies include a promoter which is operably linked to the sequences or gene(s) of interest. Other control elements may be present as well. The expression cassettes described herein may be contained within a plasmid construct. In addition to the components of the expression cassette, the plasmid construct may also include a bacterial origin of replication, one or more selectable markers, a signal which allows the plasmid construct to exist as single-stranded DNA (e.g., a M13 origin of replication), a multiple cloning site, and a "mammalian" origin of replication (e.g., a SV40 or adenovirus origin of replication).

DNA "control elements" refers collectively to transcription promoters, transcription enhancer elements, transcription termination sequences, polyadenylation sequences (located 3' to the translation stop codon), sequences for optimization of initiation of translation (located 5' to the coding sequence), translation termination sequences, upstream regulatory domains, ribosome binding sites and the like, which collectively provide for the transcription and translation of a coding sequence in a host cell. See e.g., McCaughan et al. (1995) *PNAS USA* 92:5431–5435; Kochetov et al (1998) *FEBS Letts.* 440:351–355. Not all of these control sequences need always be present in a recombinant vector so long as the desired gene is capable of being transcribed and translated.

"Operably linked" refers to an arrangement of elements wherein the components so described are configured so as to perform their usual function. Thus, control elements operably linked to a coding sequence are capable of effecting the expression of the coding sequence. The control elements need not be contiguous with the coding sequence, so long as they function to direct the expression thereof. Thus, for example, intervening untranslated yet transcribed sequences can be present between a promoter and the coding sequence and the promoter can still be considered "operably linked" to the coding sequence. Similarly, "control elements compatible with expression in a subject" are those which are capable of effecting the expression of the coding sequence in that subject.

A control element, such as a promoter, "directs the transcription" of a coding sequence in a cell when RNA polymerase will bind the promoter and transcribe the coding sequence into mRNA, which is then translated into the polypeptide encoded by the coding sequence.

A "host cell" is a cell which has been transformed, or is capable of transformation, by an exogenous nucleic acid molecule.

A cell has been "transformed" by exogenous DNA when such exogenous DNA has been introduced inside the cell membrane. Exogenous DNA may or may not be integrated (covalently linked) into chromosomal DNA making up the genome of the cell. In procaryotes and yeasts, for example, the exogenous DNA may be maintained on an episomal element, such as a plasmid. With respect to eucaryotic cells, a stably transformed cell is one in which the exogenous DNA has become integrated into the chromosome so that it is inherited by daughter cells through chromosome replication. This stability is demonstrated by the ability of the eucaryotic cell to establish cell lines or clones comprised of a population of daughter cells containing the exogenous DNA.

As used herein, a "biological sample" refers to a sample of tissue or fluid isolated from a subject, including but not limited to, for example, blood, plasma, serum, fecal matter, urine, bone marrow, bile, spinal fluid, lymph fluid, samples of the skin, external secretions of the skin, respiratory, intestinal, and genitourinary tracts, tears, saliva, milk, blood cells, organs, biopsies and also samples of in vitro cell culture constituents including but not limited to conditioned media resulting from the growth of cells and tissues in culture medium, e.g., recombinant cells, and cell components.

As used herein, the terms "label" and "detectable label" refer to a molecule capable of detection, including, but not limited to, radioactive isotopes, fluorescers, chemiluminescers, enzymes, enzyme substrates, enzyme cofactors, enzyme inhibitors, chromophores, dyes, metal ions, metal sols, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH and α-β-galactosidase.

2. Modes of Carrying out the Invention

Before describing the present invention in detail, it is to be understood that this invention is not limited to particular formulations or process parameters as such may, of course, vary. It is also to be understood that the terminology used herein is for the purpose of describing particular embodiments of the invention only, and is not intended to be limiting.

Although a number of methods and materials similar or equivalent to those described herein can be used in the practice of the present invention, the preferred materials and methods are described herein.

Central to the present invention is the discovery that the GapC protein is capable of eliciting an immune response in a vertebrate subject. In particular, the genes for the GapC proteins in *S. dysgalactiae, S. agalactiae, S. uberis, S. parauberis,* and *S. iniae* have been isolated, sequenced and characterized, and the protein sequences for those genes have been deduced therefrom. The complete DNA sequences for those genes and the corresponding amino acid sequences are shown in FIGS. 1 through 5.

As described in the examples, the full-length *S. dysgalactiae* gapC gene, depicted at nucleotide positions 1–1011, inclusive, of FIGS. 1A–1B, encodes the full-length *S. dysgalactiae* GapC protein of 336 amino acids, shown as amino acids 1–336, inclusive, of the same figure. *S. dysgalactiae* GapC has a predicted molecular weight of about 36 kDa. (calculated using the Peptide Sort program of the GCG Wisconsin Package, version 10, provided by the SeqWeb sequence analysis package, version 1.1 of the Canadian Bioinformatics Resource). Similarly, the gapC genes isolated from *S. agalactiae, S. uberis, S. parauberis* and *S. iniae* are depicted in FIGS. 2 through 5; each encodes a full-length GapC protein also of 336 amino acids, each also having a predicted molecular weight of about 36 kDa. None of the full-length sequences appear to include a signal peptide or a membrane anchor region.

FIGS. 6 and 7 show an alignment of DNA and amino acid sequences, respectively, showing regions of homology and variability that exist among GapC proteins from various streptococci strains. In particular, several variable regions are located at amino acid positions 62 to 81; 102 to 112; 165 to 172; 248 to 271; and 286 to 305. Such variable regions are typically more amenable to change. Hence, amino acid changes in these regions, such as substitutions, additions and deletions, are likely tolerated.

FIGS. 8 through 12 show plots of the following for each of the GapC proteins of the present invention: Kyte-Doolittle hydrophathy, averaged over a window of 7; surface probability according to Emini; chain flexibility according to Karplus-Schulz; antigenicity index according to Jameson-Wolf; secondary structure according to Garnier-Osguthorpe-Robson; secondary structure according to Chou-Fasman; and predicted glycosylation sites. FIGS. 13 through 17 show plots of secondary structure according to Chou-Fasman for each of the GapC proteins of the present invention. One of skill in the art can readily use the information presented in FIGS. 8 to 17 to determine immunogenic regions in the protein for use in vaccine compositions.

S. *dysgalactiae* GapC plasmin-binding protein, variants or muteins thereof, immunogenic fragments thereof, or chimeric proteins including the same, can be provided in subunit vaccine compositions. In addition, the proteins or antibodies thereto can be used as diagnostic reagents to detect the presence of infection in a vertebrate subject. Similarly, the genes encoding the proteins can be cloned and used to design probes to detect and isolate homologous genes in other bacterial strains. For example, fragments comprising at least about 8 nucleotides, preferably 15–20 nucleotides, more preferably at least about 20–50 nucleotides, and most preferably about 60–100 nucleotides, or any integer between these values, will find use in these embodiments.

The vaccine compositions of the present invention can be used to treat or prevent a wide variety of bacterial infections in vertebrate subjects. For example, vaccine compositions including GapC plasmin-binding proteins from *S. dysgalactiae, S. uberis, S. parauberis, S. iniae*, and/or group B *streptococci* (GBS) such as *S. agalactiae*, can be used to treat streptococcal infections in vertebrate subjects that are caused by these or other species. In particular, *S. uberis* and *S. agalactiae* are common bacterial pathogens associated with mastitis in bovine, equine, ovine and goat species. Additionally, group B streptococci, such as *S. agalactiae*, are known to cause numerous other infections in vertebrates, including septicemia, meningitis, bacteremia, impetigo, arthritis, urinary tract infections, abscesses, spontaneous abortion etc. Hence, vaccine compositions containing streptococcal GapC plasmin-binding proteins will find use in treating and/or preventing a wide variety of streptococcal infections.

Similarly, GapC plasmin-binding proteins derived from other bacterial genera such as *Staphylococcus, Mycobacterium, Escherichia, Pseudomonas, Nocardia, Pasteurella, Clostridium* and *Mycoplasma* will find use for treating bacterial infections caused by species belonging to those genera. Thus, it is readily apparent that GapC plasmin-binding proteins can be used to treat and/or prevent a wide variety of bacterial infections in numerous species.

The streptococcal GapC plasmin-binding proteins of the present invention can be used in vaccine compositions either alone or in combination with other bacterial, fungal, viral or protozoal antigens. These antigens can be provided separately or even as fusion proteins comprising one or more epitopes of a GapC plasmin-binding protein fused to one or more of these antigens. For example, other immunogenic proteins from *S. uberis*, such as the CAMP factor, hyaluronic acid capsule, hyaluronidase, R-like protein and plasminogen activator, can be administered with the GapC protein. Additionally, immunogenic proteins from other organisms involved in mastitis, such as from the genera *Staphylococcus, Corynebacterium, Pseudomonas, Nocardia, Clostridium, Mycobacterium, Mycoplasma, Pasteurella, Prototheca*, other streptococci, coliform bacteria, as well as yeast, can be administered along with the GapC plasmin-binding proteins described herein to provide a broad spectrum of protection. Thus, for example, immunogenic proteins from *Staphylococcus aureus, Str. agalactiae, Str. dysgalactiae, Str. zooepidemicus, Corynebacterium pyogenes, Pseudomonas aeruginosa, Nocardia asteroides, Clostridium perfringens, Escherichia coli, Enterobacter aerogenes* and *Klebsiella spp.* can be provided along with the GapC plasmin-binding proteins of the present invention.

Additionally, GapC proteins from different streptococcal species may be used together in the vaccine compositions of the present invention. In this embodiment, the multiple GapC proteins may be provided as fusion proteins or as discrete antigens in the same or different vaccine compositions.

Production of GapC Plasmin-Binding Proteins

The above-described plasmin-binding proteins and active fragments, analogs and chimeric proteins derived from the same, can be produced by variety of methods. Specifically, GapC plasmin-binding proteins can be isolated directly from bacteria which express the same. This is generally accomplished by first preparing a crude extract which lacks cellular components and several extraneous proteins. The desired proteins can then be further purified from the cell lysate fraction by, e.g., column chromatography, HPLC, immunoadsorbent techniques or other conventional methods well known in the art.

More particularly, techniques for isolating GapC plasmin-binding proteins have been described. For example, the GapC protein of *S. pyogenes* was purified from a crude cell extract by precipitation with ammonium sulfate, followed by two cycles of chromatography through a Mono FPLC column, and single cycles through superose 12 FPLC, and TSK-phenol HPLC columns (Pancholi, V. and Fischetti, V A (1992) *J. Exptl. Med* 76:415–426). Another technique involves the use of a $NAD^+$-agarose affinity column to purify GapC from lysed protoplasts of *S. pyogenes* strain 64/14 (Winram, S B and Lottenberg, R (1996) *Microbiol.* 142:2311–2320).

Alternatively, the proteins can be recombinantly produced as described herein. As explained above, these recombinant products can take the form of partial protein sequences, full-length sequences, precursor forms that include signal sequences, mature forms without signals, or even fusion proteins (e.g., with an appropriate leader for the recombinant host, or with another subunit antigen sequence for *Streptococcus* or another pathogen).

In one embodiment of the present invention, the GapC proteins are fused to a histidine tag, produced by recombinant means, and are then purified from a cell lysate fraction using affinity chromatography. See the examples.

The GapC plasmin-binding proteins of the present invention can be isolated based on the ability of the protein products to bind plasmin, using plasmin-binding assays as described below. See, e.g., the method described in the examples. Thus, gene libraries can be constructed and the resulting clones used to transform an appropriate host cell. Colonies can be pooled and screened for clones having plasmin-binding activity. Colonies can also be screened using polyclonal serum or monoclonal antibodies to the plasmin-binding protein.

Alternatively, once the amino acid sequences are determined, oligonucleotide probes which contain the codons for a portion of the determined amino acid sequences can be prepared and used to screen genomic or cDNA libraries for genes encoding the subject proteins. The basic strategies for preparing oligonucleotide probes and DNA libraries, as well as their screening by nucleic acid hybridization, are well known to those of ordinary skill in the art. See, e.g., *DNA Cloning*: Vol. 1I, supra; *Nucleic Acid Hybridization*, supra; *Oligonucleotide Synthesis*, supra; Sambrook et al., supra. Once a clone from the screened library has been identified by positive hybridization, it can be confirmed by restriction enzyme analysis and DNA sequencing that the particular library insert contains GapC plasmin-binding protein gene or a homolog thereof The genes can then be further isolated using standard techniques and, if desired, PCR approaches or restriction enzymes employed to delete portions of the full-length sequence.

Similarly, genes can be isolated directly from bacteria using known techniques, such as phenol extraction and the sequence further manipulated to produce any desired alterations. See, e.g., Sambrook et al., supra, for a description of techniques used to obtain and isolate DNA.

Alternatively, DNA sequences encoding the proteins of interest can be prepared synthetically rather than cloned. The DNA sequences can be designed with the appropriate codons for the particular amino acid sequence. In general, one will select preferred codons for the intended host if the sequence will be used for expression. The complete sequence is assembled from overlapping oligonucleotides prepared by standard methods and assembled into a complete coding sequence. See, e.g., Edge (1981) *Nature* 292:756; Nambair et al. (1984) *Science* 223:1299; Jay et al. (1984) *J. Biol. Chem.* 259:6311.

Once coding sequences for the desired proteins have been prepared or isolated, they can be cloned into any suitable vector or replicon. Numerous cloning vectors are known to those of skill in the art, and the selection of an appropriate cloning vector is a matter of choice. Examples of recombinant DNA vectors for cloning and host cells which they can transform include the bacteriophage λ (*E. coli*), pBR322 (*E. coli*), pACYC177 (*E. coli*), pKT230 (gram-negative bacteria), pGV1106 (gram-negative bacteria), pLAFR1 (gram-negative bacteria), pME290 (non-*E. coli* gram-negative bacteria), pHV14 (*E. coli* and *Bacillus subtilis*), pBD9 (*Bacillus*), pIJ61 (*Streptomyces*), pUC6 (*Streptomyces*), YIp5 (*Saccharomyces*), YCp19 (*Saccharomyces*) and bovine papilloma virus (mammalian cells). See, Sambrook et al., supra; *DNA Cloning*, supra; *B. Perbal*, supra.

The gene can be placed under the control of a promoter, ribosome binding site (for bacterial expression) and, optionally, an operator (collectively referred to herein as "control" elements), so that the DNA sequence encoding the desired protein is transcribed into RNA in the host cell transformed by a vector containing this expression construction. The coding sequence may or may not contain a signal peptide or leader sequence. If a signal sequence is included, it can either be the native, homologous sequence, or a heterologous sequence. Leader sequences can be removed by the host in post-translational processing. See, e.g., U.S. Pat. Nos. 4,431,739; 4,425,437; 4,338,397.

Other regulatory sequences may also be desirable which allow for regulation of expression of the protein sequences relative to the growth of the host cell. Regulatory sequences are known to those of skill in the art, and examples include those which cause the expression of a gene to be turned on or off in response to a chemical or physical stimulus, including the presence of a regulatory compound. Other types of regulatory elements may also be present in the vector, for example, enhancer sequences.

The control sequences and other regulatory sequences may be ligated to the coding sequence prior to insertion into a vector, such as the cloning vectors described above. Alternatively, the coding sequence can be cloned directly into an expression vector which already contains the control sequences and an appropriate restriction site.

In some cases it may be necessary to modify the coding sequence so that it may be attached to the control sequences with the appropriate orientation; i.e., to maintain the proper reading frame. It may also be desirable to produce mutants or analogs of the GapC plasmin-binding protein. Mutants or analogs may be prepared by the deletion of a portion of the sequence encoding the protein, by insertion of a sequence, and/or by substitution of one or more nucleotides within the sequence. Techniques for modifying nucleotide sequences, such as site-directed mutagenesis, are described in, e.g., Sambrook et al., supra; *DNA Cloning*, supra; *Nucleic Acid Hybridization*, supra.

The expression vector is then used to transform an appropriate host cell. A number of mammalian cell lines are known in the art and include immortalized cell lines available from the American Type Culture Collection (ATCC), such as, but not limited to, Chinese hamster ovary (CHO) cells, HeLa cells, baby hamster kidney (BHK) cells, monkey kidney cells (COS), human hepatocellular carcinoma cells (e.g., Hep G2), Madin-Darby bovine kidney ("MDBK") cells, as well as others. Similarly, bacterial hosts such as *E. coli, Bacillus subtilis,* and *Streptococcus* spp., will find use with the present expression constructs. Yeast hosts useful in the present invention include inter alia, *Saccharomyces cerevisiae, Candida albicans, Candida maltosa, Hansenula polymorpha, Kluyveromyces fragilis, Kluyveromyces lactis, Pichia guillerimondii, Pichia pastoris, Schizosaccharomyces pombe* and *Yarrowia lipolytica*. Insect cells for use with baculovirus expression vectors include, inter alia, *Aedes aegypti, Autographa californica, Bombyx mori, Drosophila melanogaster, Spodoptera frugiperda,* and *Trichoplusia ni.*

Depending on the expression system and host selected, the proteins of the present invention are produced by culturing host cells transformed by an expression vector described above under conditions whereby the protein of interest is expressed. The protein is then isolated from the host cells and purified. If the expression system secretes the protein into the growth media, the protein can be purified directly from the media. If the protein is not secreted, it is isolated from cell lysates. The selection of the appropriate growth conditions and recovery methods are within the skill of the art.

The proteins of the present invention may also be produced by chemical synthesis such as solid phase peptide synthesis, using known amino acid sequences or amino acid sequences derived from the DNA sequence of the genes of interest. Such methods are known to those skilled in the art. See, e.g., J. M. Stewart and J. D. Young, *Solid Phase Peptide Synthesis*, 2nd Ed., Pierce Chemical Co., Rockford, Ill. (1984) and G. Barany and R. B. Merrifield, *The Peptides: Analysis, Synthesis, Biology*, editors E. Gross and J. Meienhofer, Vol. 2, Academic Press, New York, (1980), pp. 3–254, for solid phase peptide synthesis techniques; and M. Bodansky, *Principles of Peptide Synthesis*, Springer-Verlag, Berlin (1984) and E. Gross and J. Meienhofer, Eds., *The Peptides: Analysis, Synthesis, Biology*, supra, Vol. 1, for classical solution synthesis. Chemical synthesis of peptides may be preferable if a small fragment of the antigen in question is capable of raising an immunological response in the subject of interest.

The GapC plasmin-binding proteins of the present invention, or their variants or fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) *J, Chrom.* 348:363–370. If serum containing polyclonal antibodies is used, the polyclonal antibodies can be purified by immunoaffinity chromatography, using known procedures.

Monoclonal antibodies to the GapC plasmin-binding proteins and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500; 4,491,632; and 4,493,890. Panels of monoclonal antibodies produced against the GapC plasmin-binding proteins, or fragments thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

Vaccine Formulations and Administration

The GapC plasmin-binding proteins, variants and fragments of the present invention can be formulated into vaccine compositions, either alone or in combination with other antigens, for use in immunizing subjects as described below. Methods of preparing such formulations are described in, e.g., *Remington's Pharmaceutical Sciences*, Mack Publishing Company, Easton, Pa., 18 Edition, 1990. Typically, the vaccines of the present invention are prepared as injectables, either as liquid solutions or suspensions. Solid forms suitable for solution in or suspension in liquid vehicles prior to injection may also be prepared. The preparation may also be emulsified or the active ingredient encapsulated in liposome vehicles. The active immunogenic ingredient is generally mixed with a compatible pharmaceutical vehicle, such as, for example, water, saline, dextrose, glycerol, ethanol, or the like, and combinations thereof. In addition, if desired, the vehicle may contain minor amounts of auxiliary substances such as wetting or emulsifying agents and pH buffering agents.

Adjuvants which enhance the effectiveness of the vaccine may also be added to the formulation. Adjuvants may include for example, muramyl dipeptides, avridine, aluminum hydroxide, dimethyldioctadecyl ammonium bromide (DDA), oils, oil-in-water emulsions, saponins, cytokines, and other substances known in the art.

The GapC plasmin-binding protein may be linked to a carrier in order to increase the immunogenicity thereof. Suitable carriers include large, slowly metabolized macromolecules such as proteins, including serum albumins, keyhole limpet hemocyanin, immunoglobulin molecules, thyroglobulin, ovalbumin, and other proteins well known to those skilled in the art; polysaccharides, such as sepharose, agarose, cellulose, cellulose beads and the like; polymeric amino acids such as polyglutamic acid, polylysine, and the like; amino acid copolymers; and inactive virus particles.

The GapC plasmin-binding proteins may be used in their native form or their functional group content may be modified by, for example, succinylation of lysine residues or reaction with Cys-thiolactone. A sulfhydryl group may also be incorporated into the carrier (or antigen) by, for example, reaction of amino functions with 2-iminothiolane or the N-hydroxysuccinimide ester of 3-(4-dithiopyridyl propionate. Suitable carriers may also be modified to incorporate spacer arms (such as hexamethylene diamine or other bifunctional molecules of similar size) for attachment of peptides.

Other suitable carriers for the GapC plasmin-binding proteins of the present invention include VP6 polypeptides of rotaviruses, or functional fragments thereof, as disclosed in U.S. Pat. No. 5,071,651, incorporated herein by reference. Also useful is a fusion product of a viral protein and the subject immunogens made by methods disclosed in U.S. Pat. No. 4,722,840. Still other suitable carriers include cells, such as lymphocytes, since presentation in this form mimics the natural mode of presentation in the subject, which gives rise to the immunized state. Alternatively, the proteins of the present invention may be coupled to erythrocytes, preferably the subject's own erythrocytes. Methods of coupling peptides to proteins or cells are known to those of skill in the art.

Furthermore, the GapC plasmin-binding proteins (or complexes thereof) may be formulated into immunogenic compositions, such as vaccine compositions or diagnostics, in either neutral or salt forms. Pharmaceutically acceptable salts include the acid addition salts (formed with the free amino groups of the active polypeptides) and which are formed with inorganic acids such as, for example, hydrochloric or phosphoric acids, or such organic acids as acetic, oxalic, tartaric, mandelic, and the like. Salts formed from free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Vaccine formulations will contain a "therapeutically effective amount" of the active ingredient, that is, an amount capable of eliciting an immune response in a subject to which the composition is administered. In the treatment and prevention of mastitis, for example, a "therapeutically effective amount" is preferably an amount that enhances resistance of the mammary gland to new infection and/or reduces the clinical severity of the disease. Such protection is demonstrated by either a reduction or lack of symptoms normally displayed by an infected host, a quicker recovery time and/or a lowered somatic cell count in milk from the infected quarter. For example, the ability of the composition to retain or bring the somatic cell count (SCC) in milk below about 500,000 cells per ml, the threshold value set by the International Dairy Federation, above which, animals are considered to have clinical mastitis, will be indicative of a therapeutic effect.

The exact amount is readily determined by one skilled in the art using standard tests. The GapC plasmin-binding protein concentration will typically range from about 1% to about 95% (w/w) of the composition, or even higher or lower if appropriate. With the present vaccine formulations, 5 to 500 µg of active ingredient per ml of injected solution should be adequate to raise an immunological response when a dose of 1 to 3 ml per animal is administered.

To immunize a subject, the vaccine is generally administered parenterally, usually by intramuscular injection. Other modes of administration, however, such as subcutaneous, intraperitoneal and intravenous injection, are also acceptable. The quantity to be administered depends on the animal to be treated, the capacity of the animal's immune system to synthesize antibodies, and the degree of protection desired. Effective dosages can be readily established by one of ordinary skill in the art through routine trials establishing dose response curves. The subject is immunized by administration of the vaccine in at least one dose, and preferably two doses. Moreover, the animal may be administered as many doses as is required to maintain a state of immunity to infection.

Additional vaccine formulations which are suitable for other modes of administration include suppositories and, in some cases, aerosol, intranasal, oral formulations, and sustained release formulations. For suppositories, the vehicle composition will include traditional binders and carriers, such as, polyalkaline glycols, or triglycerides. Such suppositories may be formed from mixtures containing the active ingredient in the range of about 0.5% to about 10% (w/w), preferably about 1% to about 2%. Oral vehicles include such normally employed excipients as, for example, pharmaceutical grades of mannitol, lactose, starch, magnesium, stearate, sodium saccharin cellulose, magnesium carbonate, and the like. These oral vaccine compositions may be taken in the form of solutions, suspensions, tablets, pills, capsules, sustained release formulations, or powders, and contain from about 10% to about 95% of the active ingredient, preferably about 25% to about 70%.

Intranasal formulations will usually include vehicles that neither cause irritation to the nasal mucosa nor significantly disturb ciliary function. Diluents such as water, aqueous saline or other known substances can be employed with the subject invention. The nasal formulations may also contain preservatives such as, but not limited to, chlorobutanol and benzalkonium chloride. A surfactant may be present to enhance absorption of the subject proteins by the nasal mucosa.

Controlled or sustained release formulations are made by incorporating the protein into carriers or vehicles such as liposomes, nonresorbable impermeable polymers such as ethylenevinyl acetate copolymers and Hytrel® copolymers, swellable polymers such as hydrogels, or resorbable polymers such as collagen and certain polyacids or polyesters such as those used to make resorbable sutures. The GapC plasmin-binding proteins can also be delivered using implanted mini-pumps, well known in the art.

The GapC plasmin-binding proteins of the instant invention can also be administered via a carrier virus which expresses the same. Carrier viruses which will find use with the instant invention include but are not limited to the vaccinia and other pox viruses, adenovirus, and herpes virus. By way of example, vaccinia virus recombinants expressing the novel proteins can be constructed as follows. The DNA encoding the particular protein is first inserted into an appropriate vector so that it is adjacent to a vaccinia promoter and flanking vaccinia DNA sequences, such as the sequence encoding thymidine kinase (TK). This vector is then used to transfect cells which are simultaneously infected with vaccinia. Homologous recombination serves to insert the vaccinia promoter plus the gene encoding the instant protein into the viral genome. The resulting TK⁻ recombinant can be selected by culturing the cells in the presence of 5-bromodeoxyuridine and picking viral plaques resistant thereto.

An alternative route of administration involves gene therapy or nucleic acid immunization. Thus, nucleotide sequences (and accompanying regulatory elements) encoding the subject GapC plasmin-binding proteins can be administered directly to a subject for in vivo translation thereof. Alternatively, gene transfer can be accomplished by transfecting the subject's cells or tissues ex vivo and reintroducing the transformed material into the host. DNA can be directly introduced into the host organism, i.e., by injection (see International Publication No. WO/90/11092; and Wolff et al. (1990) *Science* 247:1465–1468). Liposome-mediated gene transfer can also be accomplished using known methods. See, e.g., Hazinski et al. (1991) *Am. J Respir. Cell Mol. Biol.* 4:206–209; Brigham et al. (1989) *Am. J Med. Sci.* 298:278–281; Canonico et al. (1991) *Clin. Res.* 39:219A; and Nabel et al. (1990) *Science* 249:1285–1288. Targeting agents, such as antibodies directed against surface antigens expressed on specific cell types, can be covalently conjugated to the liposomal surface so that the nucleic acid can be delivered to specific tissues and cells susceptible to infection.

Diagnostic Assays

As explained above, the GapC plasmin-binding proteins of the present invention, variants and fragments thereof, may also be used as diagnostics to detect the presence of reactive antibodies of streptococcus, for example *S. dysgalactiae*, in a biological sample in order to determine the presence of streptococcus infection. For example, the presence of antibodies reactive with GapC plasmin-binding proteins can be detected using standard electrophoretic and immunodiagnostic techniques, including immunoassays such as competition, direct reaction, or sandwich type assays. Such assays include, but are not limited to, Western blots; agglutination tests; enzyme-labeled and mediated immunoassays, such as ELISAs; biotin/avidin type assays; radioimmunoassays; immunoelectrophoresis; immunoprecipitation, etc. The reactions generally include revealing labels such as fluorescent, chemiluminescent, radioactive, enzymatic labels or dye molecules, or other methods for detecting the formation of a complex between the antigen and the antibody or antibodies reacted therewith.

The aforementioned assays generally involve separation of unbound antibody in a liquid phase from a solid phase support to which antigen-antibody complexes are bound. Solid supports which can be used in the practice of the invention include substrates such as nitrocellulose (e.g., in membrane or microtiter well form); polyvinylchloride (e.g., sheets or microtiter wells); polystyrene latex (e.g., beads or microtiter plates); polyvinylidine fluoride; diazotized paper; nylon membranes; activated beads, magnetically responsive beads, and the like.

Typically, a solid support is first reacted with a solid phase component (e.g., one or more GapC plasmin-binding proteins) under suitable binding conditions such that the component is sufficiently immobilized to the support. Sometimes, immobilization of the antigen to the support can be enhanced by first coupling the antigen to a protein with better binding properties. Suitable coupling proteins include, but are not limited to, macromolecules such as serum albumins including bovine serum albumin (BSA), keyhole limpet hemocyanin, immunoglobulin molecules, thyroglobulin, ovalbumin, and other proteins well known to those skilled in the art. Other molecules that can be used to bind the antigens to the support include polysaccharides, polylactic acids, polyglycolic acids, polymeric amino acids, amino acid copolymers, and the like. Such molecules and methods of coupling these molecules to the antigens, are well known to those of ordinary skill in the art. See, e.g., Brinkley, M. A. *Bioconjugate Chem.* (1992) 3:2–13; Hashida et al., *J. Appl. Biochem.* (1984) 6:56–63; and Anjaneyulu and Staros, *International J. of Peptide and Protein Res.* (1987) 30:117–124.

After reacting the solid support with the solid phase component, any non-immobilized solid-phase components are removed from the support by washing, and the support-bound component is then contacted with a biological sample suspected of containing ligand moieties (e.g., antibodies toward the immobilized antigens) under suitable binding conditions. After washing to remove any non-bound ligand, a secondary binder moiety is added under suitable binding conditions, wherein the secondary binder is capable of associating selectively with the bound ligand. The presence of the secondary binder can then be detected using techniques well known in the art.

More particularly, an ELISA method can be used, wherein the wells of a microtiter plate are coated with a GapC plasmin-binding protein. A biological sample containing or suspected of containing anti-GapC plasmin-binding protein immunoglobulin molecules is then added to the coated wells. After a period of incubation sufficient to allow antibody binding to the immobilized antigen, the plate(s) can be washed to remove unbound moieties and a detectably labeled secondary binding molecule added. The secondary binding molecule is allowed to react with any captured sample antibodies, the plate washed and the presence of the secondary binding molecule detected using methods well known in the art.

Thus, in one particular embodiment, the presence of bound anti-GapC plasmin-binding antigen ligands from a biological sample can be readily detected using a secondary binder comprising an antibody directed against the antibody ligands. A number of anti-bovine immunoglobulin (Ig) molecules are known in the art which can be readily conjugated to a detectable enzyme label, such as horseradish peroxidase, alkaline phosphatase or urease, using methods known to those of skill in the art. An appropriate enzyme substrate is then used to generate a detectable signal. In other related embodiments, competitive-type ELISA techniques can be practiced using methods known to those skilled in the art.

Assays can also be conducted in solution, such that the GapC plasmin-binding proteins and antibodies specific for those proteins form complexes under precipitating conditions. In one particular embodiment, GapC plasmin-binding proteins can be attached to a solid phase particle (e.g., an agarose bead or the like) using coupling techniques known in the art, such as by direct chemical or indirect coupling. The antigen-coated particle is then contacted under suitable binding conditions with a biological sample suspected of containing antibodies for the GapC plasmin-binding proteins. Cross-linking between bound antibodies causes the formation of particle-antigen-antibody complex aggregates which can be precipitated and separated from the sample using washing and/or centrifugation. The reaction mixture can be analyzed to determine the presence or absence of antibody-antigen complexes using any of a number of standard methods, such as those immunodiagnostic methods described above.

In yet a further embodiment, an immunoaffinity matrix can be provided, wherein a polyclonal population of antibodies from a biological sample suspected of containing anti-GapC plasmin-binding molecules is immobilized to a substrate. In this regard, an initial affinity purification of the sample can be carried out using immobilized antigens. The resultant sample preparation will thus only contain anti-streptococcus moieties, avoiding potential nonspecific binding properties in the affinity support. A number of methods of immobilizing immunoglobulins (either intact or in specific fragments) at high yield and good retention of antigen binding activity are known in the art. Not being limited by any particular method, immobilized protein A or protein G can be used to immobilize immunoglobulins.

Accordingly, once the immunoglobulin molecules have been immobilized to provide an immunoaffinity matrix, labeled GapC plasmin-binding proteins are contacted with the bound antibodies under suitable binding conditions. After any non-specifically bound antigen has been washed from the immunoaffinity support, the presence of bound antigen can be determined by assaying for label using methods known in the art.

Additionally, antibodies raised to the GapC plasmin-binding proteins, rather than the GapC plasmin-binding proteins themselves, can be used in the above-described assays in order to detect the presence of antibodies to the proteins in a given sample. These assays are performed essentially as described above and are well known to those of skill in the art.

The above-described assay reagents, including the GapC plasmin-binding proteins, or antibodies thereto, can be provided in kits, with suitable instructions and other necessary reagents, in order to conduct immunoassays as described above. The kit can also contain, depending on the particular immunoassay used, suitable labels and other packaged reagents and materials (i.e. wash buffers and the like). Standard immunoassays, such as those described above, can be conducted using these kits.

Deposits of Strains Useful in Practicing the Invention

A deposit of biologically pure cultures of the following strains was made with the American Type Culture Collection, 10801 University Boulevard, Manassas, Va., under the provisions of the Budapest Treaty. The accession number indicated was assigned after successful viability testing, and the requisite fees were paid. The designated deposits will be maintained for a period of thirty (30) years from the date of deposit, or for five (5) years after the last request for the deposit, whichever is longer. Should a culture become nonviable or be inadvertently destroyed, or, in the case of plasmid-containing strains, lose its plasmid, it will be replaced with a viable culture(s) of the same taxonomic description.

Should there be a discrepancy between the sequence presented in the present application and the sequence of the gene of interest in the deposited plasmid due to routine sequencing errors, the sequence in the deposited plasmid controls.

| Bacterial Strain | Plasmid | Gene | Deposit Date | ATCC No. |
| --- | --- | --- | --- | --- |
| E. coli BL21 DE3 | pET15bgapC | gapC (S. dysgalactiae) | May 31, 2000 | PTA-1976 |
| E. coli BL21 DE3 | pMF521c | gapC (S. agalactiae) | May 31, 2000 | PTA-1975 |
| E.coli BL21 DE3 | pMF521a | gapC (S. uberis) | May 31, 2000 | PTA-1973 |
| E.coli BL21 DE3 | pMF521e | gapC (S. iniae) | May 31, 2000 | PTA-1972 |

3. Experimental

Below are examples of specific embodiments for carrying out the present invention. The examples are offered for illustrative purposes only, and are not intended to limit the scope of the present invention in any way.

Efforts have been made to ensure accuracy with respect to numbers used (e.g., amounts, temperatures, etc.), but some experimental error and deviation should, of course, be allowed for.

Materials and Methods

Enzymes were purchased from commercial sources, and used according to the manufacturers' directions.

In the isolation of DNA fragments, except where noted, all DNA manipulations were done according to standard procedures. See, Sambrook et al., supra. Restriction enzymes, $T_4$ DNA ligase, E. coli, DNA polymerase II, Klenow fragment, and other biological reagents can be purchased from commercial suppliers and used according to the manufacturers' directions. Double stranded DNA fragments were separated on agarose gels.

EXAMPLE 1

Preparation Amplification, Sequencing, Expression, Purification and Characterization of the *S. dysgalactiae* GapC Plasmin Binding Protein A. Preparation of *S. dysgalactiae* Chromosomal DNA A clinical *S. dysgalactiae* isolate from a case of bovine mastitis (ATCC Accession No. ATCC43078) was obtained from the American Type Culture Collection (10801 University Boulevard, Manassas, Va. 20110-2209), and was used as a source of DNA. The organism was routinely grown on TSA sheep blood agar plates (PML Microbiologicals, Mississauga, Ontario) at 37° C. for 18 hours, or in Todd-Hewitt broth (Oxoid Ltd., Hampshire, England) supplemented with 0.3% yeast extract (THB-YE) at 37° C., 5% $CO_2$.

Chromosomal DNA was prepared from *S. dysgalactiae* grown in 100 ml of THB-YE supplemented with 20 mM glycine for approximately 6 hours, until an $A_{600}$ of 0.8 to 1.0 was reached. Cells were harvested and re-suspended in 50 mM EDTA, 50 mM Tris-HCl, 0.5% Tween-20® (Sigma, St. Louis, Mo.) and supplemented with RNase A (200 mg/ml), proteinase K (20 mg/ml), lysozyme (100 mg/ml) and mutanolysin (100 mg/ml). (SIGMA, St. Louis, Mo.). Following bacterial lysis for 30 minutes at 37° C. with vigorous shaking, guanidine hydrochloride and Tween-2®, pH 5.5, were mixed with the lysate to give a final concentration of 0.8 M and 5%, respectively. This mixture was incubated at 50° C. for 30 minutes. The chromosomal DNA was then purified using a Qiagen genomic-tip 100 g (Qiagen, Santa Clarita, Calif.) and precipitated using 0.7 volumes of iso-propanol. The resulting pellet was washed in 70% ethanol and re-suspended in 0.5 ml 10 mM Tris-HCl, pH 8.8.

B. Amplification and Cloning of the *S. dysgalactiae* gapC Gene

The gapC gene was amplified by PCR (See Mullis et al., U.S. Pat. No. 4,683,195; Mullis, U.S. Pat. No. 4,683,202;). The forward primer, gapCl, contained an NdeI restriction (SEQ ID NO:1, shown in Table 1) and the reverse primer, gapClr, contained a BamHI site (SEQ ID NO:2, shown in Table 1). In the preceding primer sequences, depicted in Table 1, underlining denotes nucleotides added to the original sequence, and bolding indicates the location of restriction endonuclease recognition sites.

PCR was carried out using Vent DNA polymerase (New England Biolabs, Mississauga, ON, Canada). 0.7 µg of *S. dysgalactiae* chromosomal DNA was incubated in a reaction mixture containing 1 µM of each of the preceding primers, 200 µM each of dATP, dTTP, dCTP and dGTP, 3 mM $MgSO_4$, 1× concentration of Thermopol buffer (New England Biolabs, Mississauga, ON, Canada) and 2 units Vent DNA polymerase. This mixture was incubated for 3 amplification cycles of 1 minute at 94° C., 3 minutes at 50° C. and 1 minute, 10 seconds at 72° C., then for 27 amplification cycles at 15 seconds at 95° C., 30 seconds at 55° C., and 1 minute at 72° C., and finally for 1 cycle of 5 min 72° C.

TABLE 1

Sequence Identification Numbers and Corresponding Nucleotide and Amino Acid Sequences

| SEQ ID NO. | Name | Sequence |
|---|---|---|
| 1 | Primer gapC1 | 5'-<u>GG CGG CGG CAT</u> ATG GTA GTT AAA GTT GGT ATT AAC GG-3' |
| 2 | Primer gapC1r | 5'-<u>GC GGA TCC</u> TTA TTT AGC GAT TTT TGC AAA GTA CTC-3' |
| 3 | *Streptococcus dysgalactiae* gapC gene | (see FIG. 1) |
| 4 | *Streptococcus dysgalactiae* GapC protein | |
| 5 | *Streptococcus agalactiae* gapC gene | (see FIG. 2) |
| 6 | *Streptococcus agalactiae* GapC protein | |
| 7 | *Streptococcus uberis* gapC gene | (see FIG. 3) |
| 8 | *Streptococcus uberis* GapC protein | |
| 9 | *Streptococcus parauberis* gapC gene | (see FIG. 4) |
| 10 | *Streptococcus parauberis* GapC protein | |
| 11 | *Streptococcus iniae* gapC gene | (see FIG. 5) |
| 12 | *Streptococcus iniae* GapC protein | |

The gapC PCR product was cloned into the expression vector pET15B (Novagen, Madison, Wis.) which had been digested with BamHI and NdeI. Cloning of the PCR product into this site results in the addition of an in-frame coding sequence for a hexahistidyl (6×His) tag to the gapC coding sequence. Subsequent expression yields a full-length protein with an attached histidine tag, which permits purification of the protein under non-denaturing conditions using metal chelate chromatography.

This construct was used to transform E. coli BL21 DE3 (Life Technologies, Gaithersburg, Md.). This transformed strain was designated BL21 DE3 (pET15bgapC) (ATCC No. PTA-1976).

C. Isolation of Chromosomal DNA and Amplification and Cloning of the gapC Gene from S. agalactiae, S. uberis, S. parauberis and S. iniae The gapC gene were prepared from other isolates essentially as described above.

Chromosomal DNA from S. agalactiae, S. uberis, and S. parauberis was isolated from strains obtained from the American Type Culture Collection (10801 University Boulevard, Manassas, Va. 20110-2209; strains designated ATCC 27541, 9927, and 13386, respectively). Chromosomal DNA from S. iniae was isolated from a strain designated 9117 obtained from Mount Sinai Hospital, University of Toronto.

The primers used to amplify the gapC genes from the Streptococcus strains listed above were the same as those used in the case of S. dysgalactiae, i.e., primer gapCl (SEQ ID NO:1) and primer gapClr (SEQ ID NO:2).

After amplification, the PCR product in each case was cloned into pPCR-Script, using the cloning protocol described in the PCR-Script Amp cloning Kit (Stratagene, La Jolla, Calif.) and used to transform E. coli XL10-Gold (Stratagene, La Jolla, Calif.). The PCR product insert was then excised using NdeI and BamHI and re-cloned into those sites in pE15b using conventional cloning protocols (See e.g., Sambrook et al., supra.) and used to transform E. coli DH5αF'lacl$^q$. The resulting plasmids containing the S. agalactiae, S. uberis, S. parauberis and S. iniae were designated pMF521c (ATCC No. PTA-1 975), pMF521a (ATCC No. PTA-1973), pMF521d, and pMF521e (ATCC No. PTA-1972), respectively. For expression of (6×His) GapC proteins, constructs were used to transform E. coli BL21 DE3, as described above.

D. Nucleotide Sequence of the gapC Gene and Deduced Amino Acid Sequences

Sequences homologous to gapC of S. equisimilis homolog (Gase, et al. (1996) European J. of Biochem. 239:42–51) were originally identified while sequencing a linked but unrelated gene of S. dysgalactiae. To obtain the complete sequence of the S. dysgalactiae gapC gene, PCR was employed using the primers described above, i.e., primer gapCl and primer gapClr.

The sequence was determined using fluorescence tag terminators on an ABI 373 DNA automatic sequencer (Applied Biosystems, Emeryville, Calif.) at the Plant Biotechnology Institute (PBI, Saskatoon, Canada).

FIGS. 1A–1B depict the coding sequence of the gapC gene from S. dysgalactiae (DysGapC) (SEQ ID NO:3) and the deduced amino acid sequence (SEQ ID NO:4).

The sequences of the GapC proteins isolated form S. agalactiae, S. uberis, S. parauberis, and S. iniae were determined by the same method.

FIGS. 2 through 5 depict both the nucleotide sequences and the predicted amino acid sequences for the S. dysgalactiae GapC protein (DysgalGapC) (SEQ ID NO:3 and SEQ ID NO:4), as well as for the GapC proteins of S. agalactiae (AgalGapC) (SEQ ID NO:5 and SEQ ID NO:6), S. uberis (UberGapC) (SEQ ID NO:7 and SEQ ID NO:8), S. parauberis (PUberGapC) (SEQ ID NO:9 and SEQ ID NO:10), and S. iniae (IniaeGapC) (SEQ ID NO:11 and SEQ ID NO:12), respectively.

The S. dysgalactiae GapC protein gene depicted in FIGS. 1A–1B codes for a 336 amino acid protein which does not appear to contain either a signal sequence or membrane anchor domain. A search of the GenBank database using the BLASTX program revealed that the open reading frame was 95.5% homologous to GapC of S. equisimilis (GenBank Accession No. X97788) and 99.4% homologous to GapC of S. pyogenes (GenBank Accession No. M95569). The predicted amino acid sequence of the GapC protein also exhibited 43% amino acid identity to bovine glyceraldehyde-3-phosphate dehydrogenase (GenBank Accession No. U85042).

Similarly, for the S. agalactiae, S. uberis, S. parauberis and S. iniae GapC protein sequences, neither signal sequences nor membrane anchor domains appear to be present.

Sequence homologies are tabulated in Table 2.

TABLE 2

Sequence Homologies Between Various GapC Protein Sequences

| | S. equisimilis | S. pyogenes | Bovine GAPDH |
|---|---|---|---|
| S. dysgalactiae | 95.5% | 99.4% | 43% |
| S. agalactiae | 87.02% | 91.07% | (not determined) |
| S. parauberis | 86.31% | 90.77% | |
| S. uberis | 88.39% | 92.26% | |
| S. iniae | 86.31% | 89.88% | |

E. Expression and Purification of the Recombinant S. dysgalactiae GapC Plasmin Binding Protein The Hexahistidyl-tagged GapC protein was expressed and purified under non-denaturing conditions using metal chelate (Ni-NTA) agarose (Qiagen, Santa Clarita, Calif.) affinity chromatography according to the manufacturers directions.

E. coli BL21 DE3 containing the recombinant plasmid was grown in Luria Broth, containing 100 µg/ml ampicillin to an $A_{600}$ of approximately 0.5. Expression of the GapC protein was then induced by the addition of 1 mM isopropyl-β,D-thiogalactoside (IPTG) (Sigma, St. Louis, Mo.]. Following three hours incubation at 37° C., cells were harvested, washed in column buffer (50 mM sodium phosphate buffer, pH8.0, 0.3 M NaCl, 10 mM imidazole) and lysed by sonication.

Approximately 40% of the recombinant protein was in the soluble fraction of the cell sonicate with a yield of approximately 50 mg of the recombinant protein per litre of culture volume, determined with a DC Protein Assay Kit (Bio-Rad Laboratories, Mississauga, ON, Canada) using bovine serum albumin (Pierce, Rockford, Ill.) as a standard.

The lysate was cleared by centrifugation and the soluble fraction was applied to a Ni-NTA column (Qiagen), which was subsequently washed with 10 column volumes of column buffer (as above, except containing 20 mM imidazole). The Hexahistidyl-tagged GapC was eluted using column buffer (as above, except containing 250 mM imidazole), yielding a homogenous protein fraction having a GapC concentration of 10–15 mg/ml. That fraction was dialyzed against 2000 volumes of PBSA (136 mM sodium chloride, 2.6 mM potassium chloride, 8.1 mM sodium phosphate dibasic, 1.46 mM potassium phosphate monobasic).

F. Expression and Purification of Recombinant GapC Protein from S. agalactiae, S. uberis, S. parauberis, and S. iniae Expression and purification of the recombinant proteins from these streptococcus species is accomplished by the same methods described in Example 1E, above. The transformed bacterial strains used to express the S. agalactiae, S. uberis, S. parauberis and S. iniae recombinant GapC proteins were designated BL21 DE3 (pMF521c) (ATCC No. PTA-1975), BL21 DE3 (pMF521a) (ATCC No. PTA-1973), BL21 DE3 (pMF521d), and BL21 DE3 (pMF521e) (ATCC No. PTA-1972), respectively.

G. Characterization of the Recombinant *S. dysgalactiae* GapC Protein

1. SDS-Page Analysis

SDS-polyacrylamide gel electrophoresis was performed on a sample of the eluted protein using the method described by Laemli (Laemli, U. K. (1970) *Nature* 227:680–685). The results are presented in FIG. 18. In the figure: lane 1, molecular weight markers (20.5 to 103 kDa range; BioRad Laboratories, Emeryville, Calif.); lane 2, soluble recombinant *S. dysgalactiae* GapC protein purified by Ni-NTA affinity chromatography.

These results demonstrate that purification by affinity chromatography on a Ni-NTA column yielded a homogenous protein fraction.

2. Glyceraldehyde-3-phosphate Dehydrogenase (GAPDH) Activity of Recombinant GapC and *S. dysgalactiae* Whole Cells GAPDH catalyzes the oxidative phosphorylation of D-glyceraldehyde-3-phosphate to 1, 3-diphosphoglycerate in the presence of $NAD^+$ and inorganic phosphate. The high degree of homology of GapC to streptococcal glyceraldehyde-3-phosphate dehydrogenase suggested that GapC may exhibit this enzyme activity.

The GAPDH activity of *S. dysgalactiae* whole cells ($10^{10}$ CFU) and the recombinant GapC protein was determined by measuring the reduction of $NAD^+$ to NADH. The assay buffer was composed of 40 mM triethanolamine, 50 mM $Na_2 HPO_4$ and 5 mM EDTA, pH 6.8. *S. dysgalactiae* cells or 5 mg of purified recombinant protein were incubated in assay buffer containing 7 ml glyceraldehyde-3-phosphate (49 mg/ml; Sigma Chemical Company), 75 microliters $NAD^+$ (15 mM; Sigma Chemical Company) in a final volume of 1 ml. Negative controls consisted of samples which did not contain glyeraldehyde-3-phosphate or the recombinant GapC molecule/*S. dysgalactiae* cells. The reduction of $NAD^+$ to NADH was monitored spectrophotometrically at an Absorbance of 340 nanometers.

The results indicated that both the recombinant protein as well as intact wild-type *S. dysgalactiea* cells had enzymatic activity (not shown). Furthermore, when *S. dysgalactiae* cells were treated with Trypsin to digest surface proteins, GAPDH activity disappeared. Thus, the enzymatic activity observed for the intact wild type cells was not due to intracellular GAPDH.

This data suggests that the GapC protein is localized on the cell surface despite the apparent lack of either a signal sequence or a membrane anchoring region in either the nucleotide or amino acid.

3. Plasmin-Binding Activity of Recombinant *S. dysgalactiae* GapC Plasmin Binding Protein and *S. dysgalactiae* Whole Cells.

A microplate assay was used to determine if the recombinant GapC protein was capable of binding bovine plasmin, and if so whether the bound plasmin was in an enzymatically active form.

Ninety-six-well microtiter plates were coated with 5 mg of purified recombinant GapC protein, washed 3 times with 0.1% gelatin-PBSA with 0.05% TWEEN-20 (PBSGT). The wells were blocked for one hour at 37° C. in the same buffer, washed, and incubated with 200 ml of bovine plasmin (0.25 mg/ml; Boehringer Mannheim, Indianapolis, Ind.) for 1 hr at 37° C. The wells were then washed 8 times with PBSGT. 200 ml of the synthetic substrate chromazine-PL (Tos-Gly-Pro-Lys-4-NA, 0.3 mg/ml) were added to the wells and incubated at 37° C. for one hour. The presence of associated plasmin activity was determined by measuring the level of paranitroanalide (4-nitraniline) released into the supernatant and detected based on an Absorbance of 405 nanometers. A similar procedure was used to measure plasmin-binding activity of *S. dysgalactiae* whole cells, with the exception that $10^{10}$ cells were washed with PBSGT and re-suspended in 400 µl chromazine-PL (0.3mg/ml) and incubated for 1 hour at 37° C.

Figure 19:
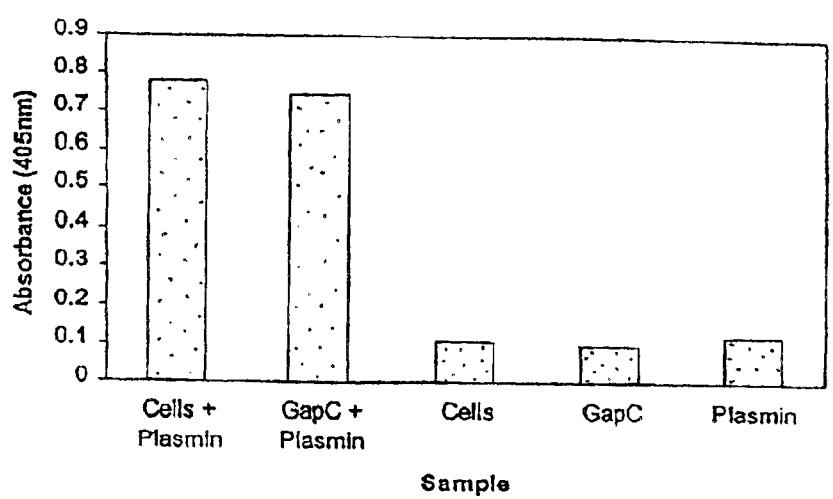
FIG. 19 is a histogram which compares the enzymatic activity of bovine plasmin bound to intact *S. dysgalactiae* cells; bovine plasmin bound to affinity-purified recombinant *S. dysgalactiae* GapC protein; intact *S. dysgalactiae* cells alone; affinity-purified recombinant *S. dysgalactiae* GapC protein alone; and bovine plasmin alone. Activity was determined by an increase in the absorbance at 405 nm following release of paranitroanalide from the synthetic substrate chromozine-PL (Roche Diagnostics, Laval, Quebec, Canada). The data represents the mean of three individual assays.

The results, shown in FIG. 19, demonstrate that the purified recombinant protein was capable of binding enymatically active bovine plasmin. Likewise, when *S. dysgalactiae* whole cells were utilized, similar results were obtained. In the figure, the data represents the mean of three individual assays.

Thus, the plasmin-receptor is located on the surface of *S. dysgalactiae* and the purified protein retains biological activity.

EXAMPLE 2

Immunization with *S. dysgalactiae* GapC and Experimental Infection of Cattle

Figure 18:
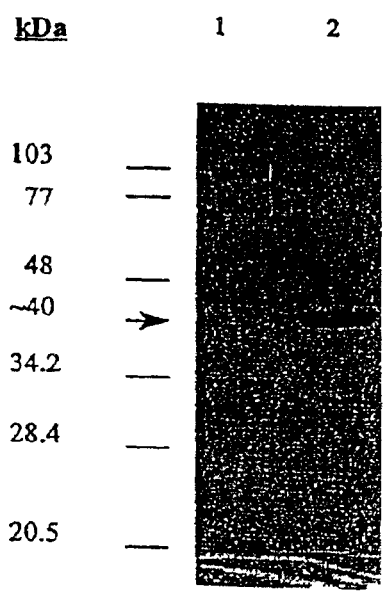
FIG. 18 shows the results of SDS-polyacrylamide gel electrophoresis of recombinant *S. dysgalactiae* GapC produced in *E. coli* DE3. Lane 1, molecular weight markers (20.5–103 kDa; BioRad, Emeryville, Calif.); lane 2, soluble recombinant *S. dysgalactiae* GapC purified by Ni-NTA affinity chromatography. Numbers on the left of the figure indicate the positions of the molecular weight markers (in kDa).

Vaccines were formulated in such a fashion that they contained 50 mg/ml of affinity purified recombinant GapC in the oil-based adjuvant VSA3 (VIDO, Saskatoon, Saskatchewan, Canada; van Drunen Littel-van den Hurk et al. (1993) *Vaccine* 11:25–35). VSA3 is a combination of Emulsigen Plus™ (MVP Laboratories, Ralston, Nebr.) and Dimethyldioctadecyl ammonium bromide (Kodak, Rochester, N.Y.). The affinity-purified recombinant GapC protein used for the vaccine preparation is shown in FIG. 18.

Twenty-four non-lactating Holsteins with no history of *S. dysgalactiae* infection were obtained from various farms in Saskatchewan, Canada. One week prior to vaccination, all animals were treated with Cepha-dry™ (Ayerst Laboratories, Montreal, Canada) (300 mg per quarter), in order to clear any infection of the udders prior to the vaccination step.

Groups of 8 animals were immunized subcutaneously with two doses of vaccines containing *S. dysgalactiae* GapC, Mig (an Fc receptor protein isolated from *S. dysgalactiae* which was evaluated simultaneously), or a placebo with a three-week interval between immunizations. Two weeks following the second immunization, animals were exposed to 650 colony forming units of *S. dysgalactiae* delivered into three quarters with an udder infusion cannula. The fourth quarter on each animal served as an un-infective control.

All animals were examined daily for clinical signs of disease and samples from all udder quarters were collected on each day. Samples were observed for consistency and somatic cell counts as well as bacterial numbers were determined.

EXAMPLE 3

Determination of GapC-specific Antibodies

GapC-specific antibodies in bovine serum were measured using an enzyme-linked immunosorbent assay (ELISA). Briefly, microtiter plates (NUNC, Naperville, Ill.) were coated by adding 1 microgram per well purified recombinant antigen in 50 mM sodium carbonate buffer, pH 9.6, and incubated overnight at 4° C. The liquid was removed and the wells were blocked with 3% bovine serum albumin for 1 hr at 37° C. Serial dilutions of bovine serum (from 1 in 4 to 1 in 6,400) were then added to the wells and incubated for 2 hours at room temperature. The wells were aspirated, washed and incubated with 100 ml of alkaline phosphatase-conjugated goat anti-bovine IgG (Kirkgaard & Perry Laboratories Inc., Gaithersburg, Md.) for 1 hr at room temperature. The wells were washed again, and 100 µl of p-nitrophenol phosphate (SIGMA, St. Louis, Mo.) was added as a substrate to detect alkaline phosphatase activity. The absorbance at 405 nanometers was recorded following 1 hr incubation with the substrate at room temperature.

Where referred to in the figures, the specific antibody titer is expressed as the reciprocal of the dilution showing activity above background levels.

EXAMPLE 4

Bacterial Colonization

Bacteria were enumerated by spreading serial dilutions ($10^0$ to $10^{-3}$) directly onto TSA sheep blood agar plates followed by overnight incubation at 37° C., 5% $CO_2$. Colonization is defined as >500 cfu/ml of the challenge organism recovered.

To confirm that the bacteria recovered from milk secretions were *S. dysgalactiae*, selected colonies recovered from each animal were tested using an API strep-20 test (bioMerieux SA, Hazelwood, Mo.) according to the manufacturer's instructions. This test is a standardized method combining 20 biochemical tests for the determination of enzymatic activity and fermentation of sugars. The reactions are read according to a reading table and the identification is obtained by either referring to the analytical profile index or using identification software.

Figure 20:
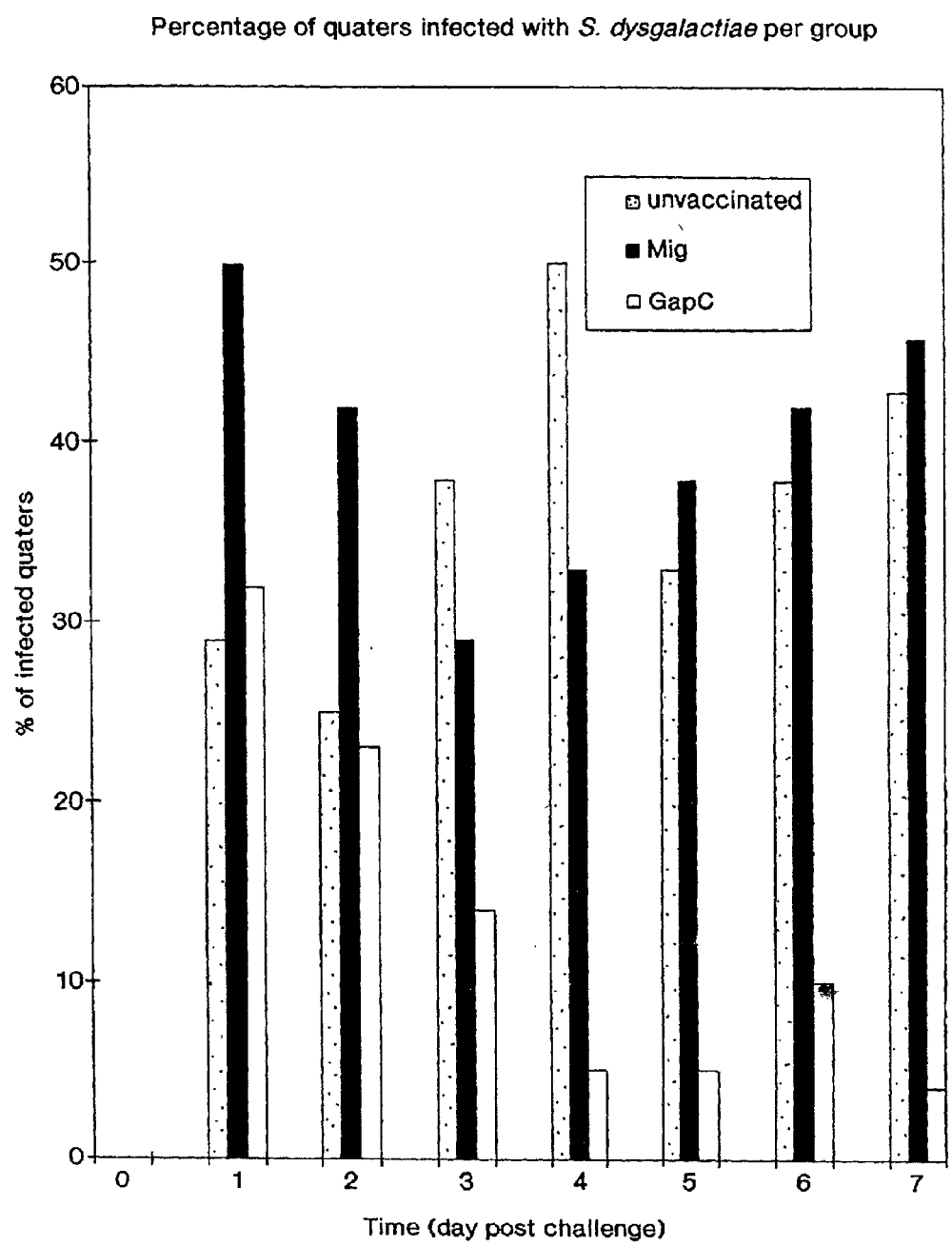
FIG. 20 compares the change in the percentage of udder quarters infected with *S. dysgalactiae* over a 7 day period among three experimental groups: (1) unvaccinated control animals; (2) animals vaccinated with the Mig Fc binding protein; and (3) animals vaccinated with GapC. Infection was defined as recovery of >500 cfu of the *S. dysgalactiae* per ml of milk secretions.

Following challenge, animals from all groups were shown to be colonized by *S. dysgalactiae* (FIG. 20). Only the GapC-immunized cows had a statistically significant reduction in the number of infected quarters and total numbers of bacteria isolated per quarter. Therefore, immunization with GapC reduced bacterial colonization following challenge with *S. dysgalactiae*.

Figure 21:
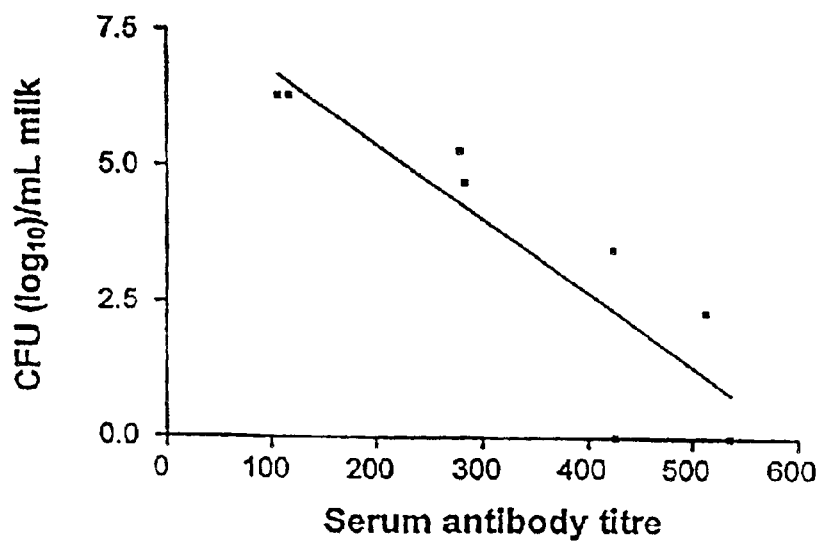
FIG. 21 plots the maximum number of *S. dysgalactiae* in any udder quarter against serum anti-GapC antibody titer (expressed as the reciprocal of the dilution showing activity above background levels). Serum anti-GapC titers were shown to correlate with the maximum number of cfu/ml recovered from the mammary glands ®=0.74, as determined using GraphPad Prism software, v. 2.01, from GraphPad Software, Inc., San Diego, Calif.).
Figure 22:
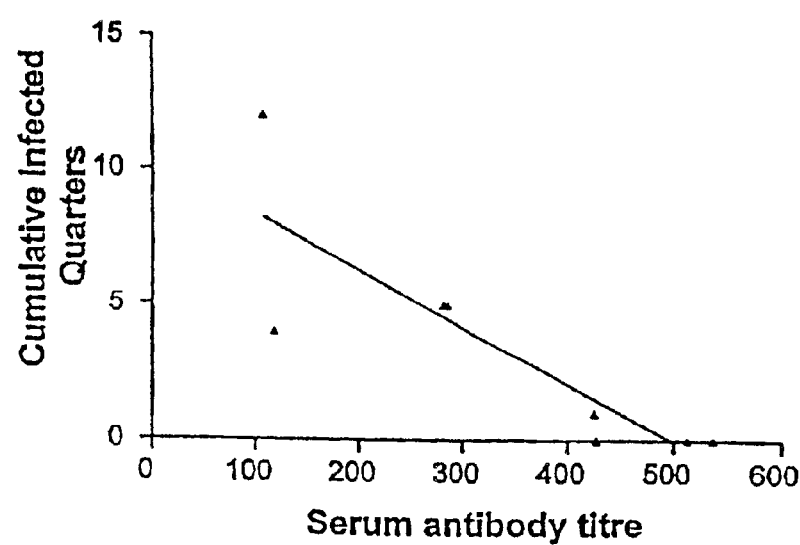
FIG. 22 plots cumulative number of infected mammary quarters against serum antibody titer (again expressed as the reciprocal of the dilution showing activity above background levels). A strong correlation between the anti-GapC antibody serum antibody level and the total number of infected quarters was observed.

The relationship between anti-GapC titer and bacterial colonization is shown in FIGS. 21 and 22. There was a strong correlation between anti-GapC serum antibody level and the maximum number of bacteria (expressed in CFU ($log_{10}$)/ml milk) found in any quarter r=0.74) (FIG. 21) as well as the total number of infected quarters ($r^2$=0.74) (FIG. 22). Correlation was calculated using GraphPad Prism software, version 2.01 (GraphPad Software Inc., San Diego, Calif.).

Figure 23:
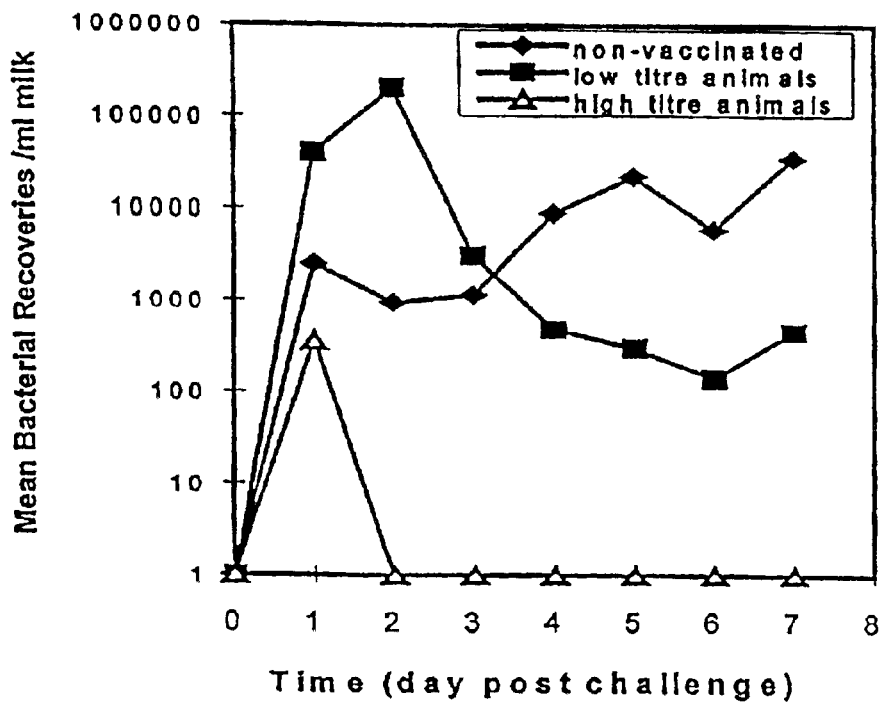
FIG. 23 illustrates the recovery of bacteria from GapC-immunized animals; data points are plotted as mean bacterial recoveries/ml milk vs. time (in days post-challenge). In the figure, diamonds (-♦-) represent non-vaccinated animals; squares (-■-) represent low titer animals (i.e., animals exhibiting the poorest response against GapC in terms of antibody titer), and triangles (-Δ-) represent high titer animals (i.e., the remaining animals).
Figure 24:
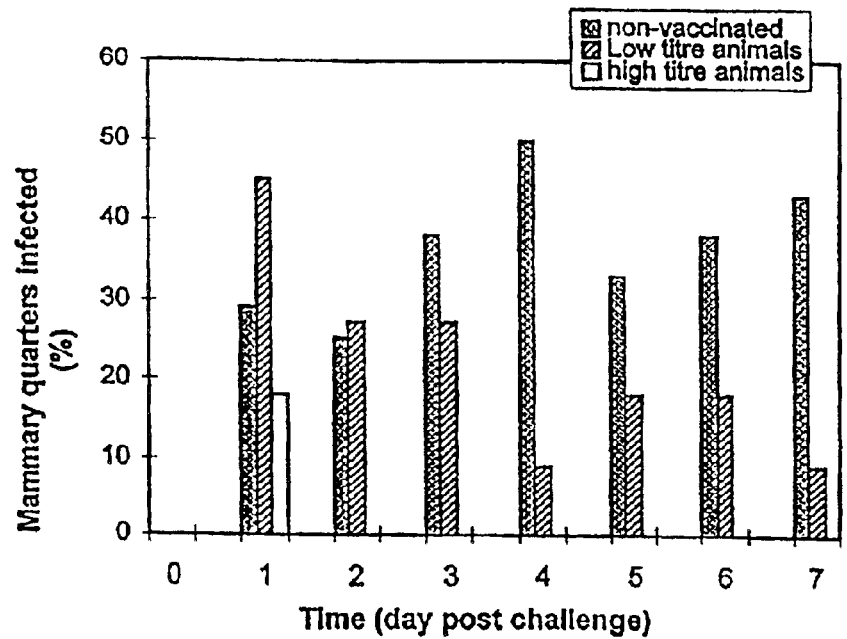
FIG. 24 shows recovery of *S. dysgalactiae* from GapC-immunized animals, plotted as the percent of mammary quarters infected vs. time in days post-challenge. In the figure, the stippled bars represent non-vaccinated animals; the cross-hatched bars represent low-titer animals (i.e., animals exhibiting the poorest response against GapC in terms of antibody titer) and the unshaded bars represent high-titer animals (i.e., the remaining animals).

This correlation is also illustrated in FIGS. 23 and 24 where the GapC-immunized group is subdivided into high titer and low titer responders. In these figures, "low titer responders" refer to the four animals with the poorest response against GapC while "high titer responders" refer to the remainder of the group. No colonization occurred in the high titer group, while even the low titer group showed reduced numbers of bacteria recovered after day 3.

EXAMPLE 5

Determination of Inflammatory Response

Inflammatory response was measured as a function of somatic cell count (i.e., lymphocytes, neutrophils, and monocytes). Somatic cell counts were measured in a Coulter counter using standard techniques, as recommended by Agriculture and Agri-Food Canada Pamphlet IDFSOB (1985) *Milk and Milk products—Methods of Sampling*. Samples were always read within 48 hours of collection and fixation, at days 1 through 7 post challenge.

Figure 25:
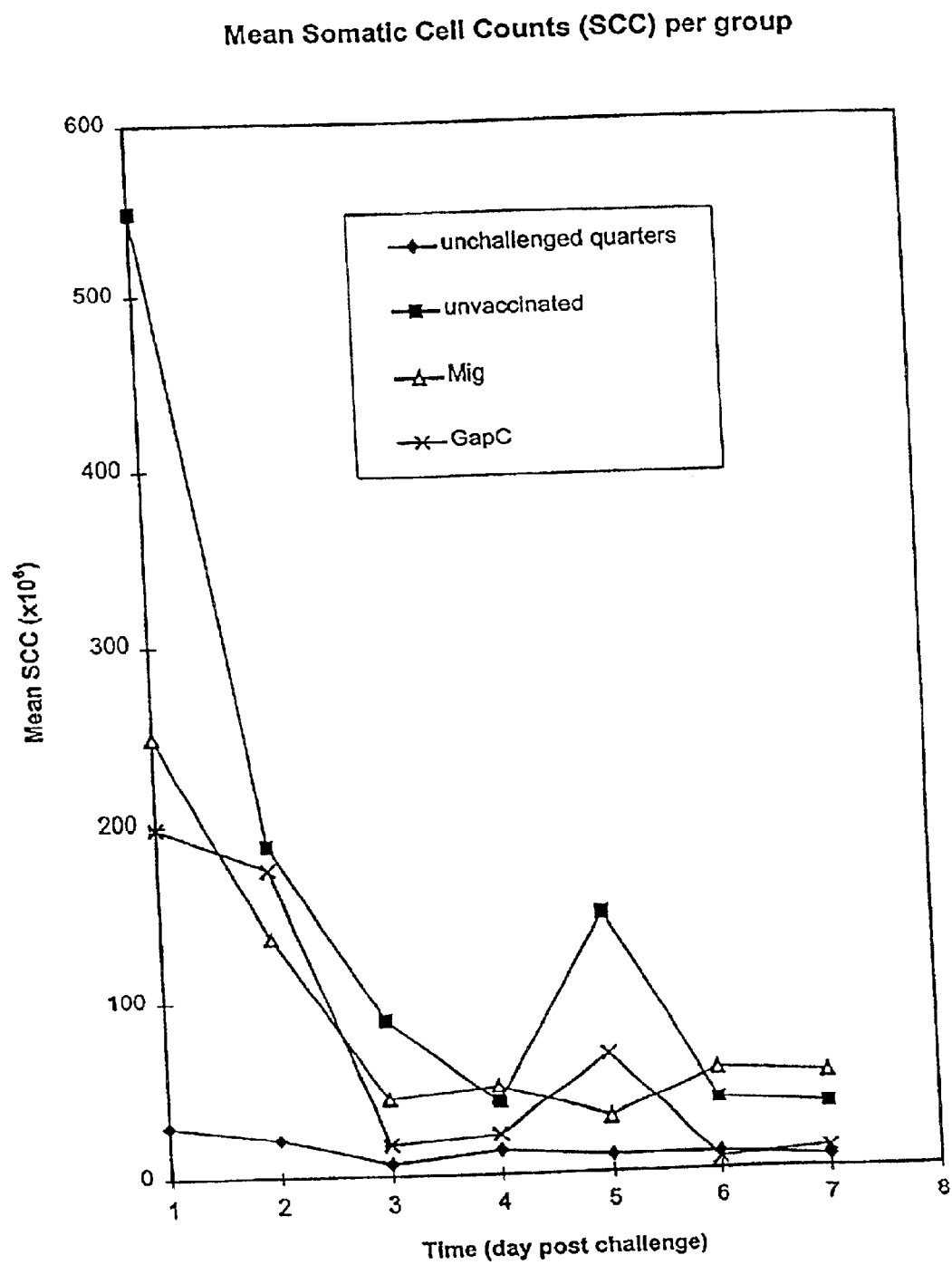
FIG. 25 depicts the observed inflammatory response to infection with *S. dysgalactiae* plotted as mean somatic cell counts (SCC) for each experimental group versus time in days post challenge. In the figure, diamonds (-♦-) represent unchallenged, unvaccinated quarters, squares (-■-) represent challenged, unvaccinated animals, triangles(-Δ-) represent challenged, Mig-vaccinated animals, and x's (-X-) represent challenged, GapC-vaccinated animals.
Figure 26:
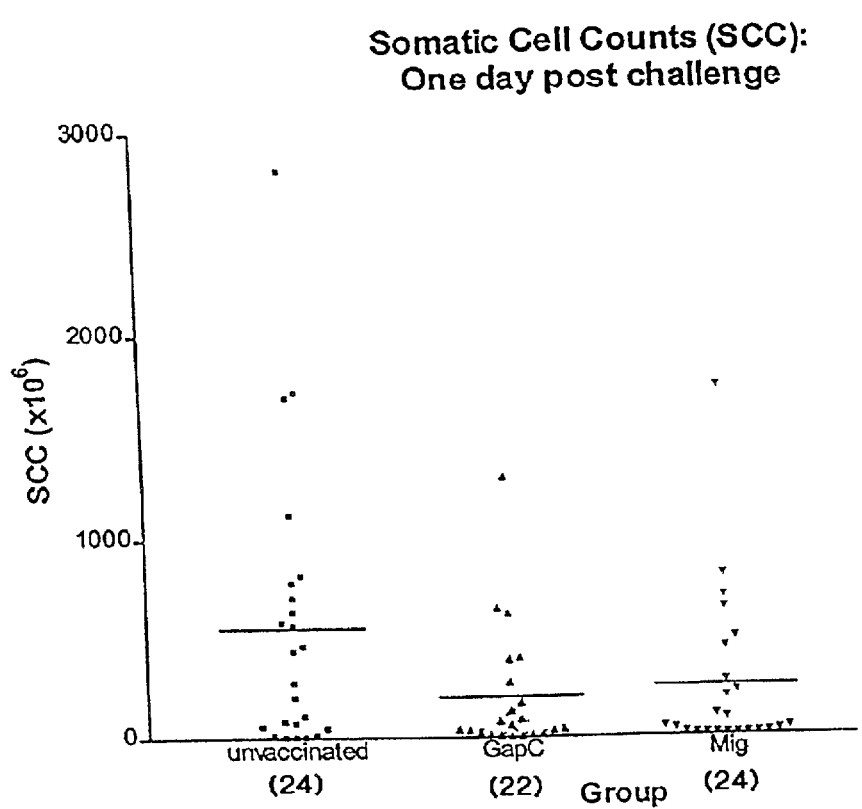
FIG. 26 illustrates somatic cell counts per mammary quarter on day 1 post-challenge. In the figure, the bar represents the mean for each group. Squares (-■-) represent unvaccinated animals; triangles (-▲-) represent GapC-vaccinated animals, and inverted triangles (-▼-) represent Mig-vaccinated animals.
Figure 27:
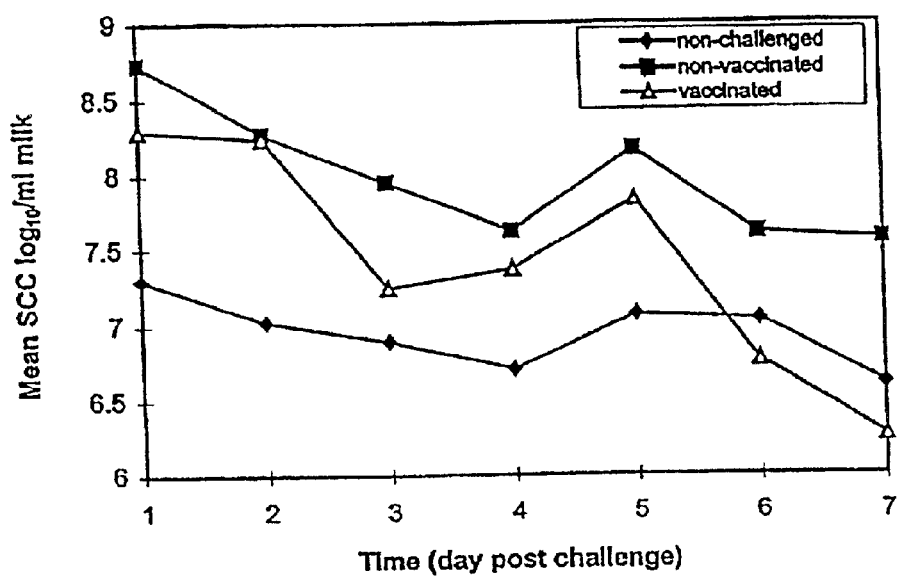
FIG. 27 depicts the somatic cell counts of non-vaccinated, non-challenged and GapC-immunized, high-titer animals (i.e., the four animals exhibiting the highest antibody titers of the eight animals in the particular group) for seven days post challenge, plotted as the $\log_{10}$ of the mean somatic cell count/ml milk against time in days post challenge. Diamonds (-♦-) represent unchallenged, unvaccinated animals, squares (-■-) represent challenged, unvaccinated animals, and triangles (-Δ-) represent challenged, GapC-vaccinated animals.

The numbers of somatic cells present in the gland was determined on each day post challenge. Numbers from the unchallenged quarter remained constant throughout the trial while on day 1, the GapC group was lower than the placebo-immunized group (FIG. 25). The difference between the GapC and the placebo groups was statistically significant. The individual data from day 1 is shown in FIG. 26; data for GapC-treated animals over a 7 day period post-challenge is shown in FIG. 27. Samples from the quarters of GapC-immunized animals were indistinguishable from unchallenged quarters.

Therefore, immunization with GapC reduced the inflammatory response following challenge with *S. dysgalactiae*.

EXAMPLE 6

Immunization and Challenge of Lactating Cows

Similar experiments to test the effectiveness of vaccines comprising *S. uberis* and *S. dysgalactiae* in lactating cows were conducted as follows. A total of 99 lactating Holstein cows were screened for the presence of serum IgG against *S. uberis* whole cells, GapC and CAMP) another streptococcal antigen. Four groups of 8 animals were selected for vaccination with a placebo, (6×His)GapC of *S. uberis*, (6×His)GapC of *S. dysgalactiae* and CAMP-3. Each vaccine dose (2 ml) included 100 µg/ml of purified (6×His)GapC, CAMP-3 or antigen-free placebo (0.85% (w/v) saline), and 30% VSA3 (VIDO, Saskatoon, Saskatchewan, Canada; van Drunen Littel-van den Hurk et al. (1993) *Vaccine* 11:25–35). Cows received 2 subcutaneous injections in the neck at 36 (day 0) and 15 days prior to challenge. Eight days before challenge, milk samples from each quarter were analyzed for the presence of bacteria, and infected animals were excluded from the trial. Subsequently, 6 cows from each group were challenged. Three hrs before challenge, teats were washed with clean, warm water, dried, and alcohol swabbed. Milk samples were collected for somatic cell counts (SCC) and bacteriology. The left udder quarters remained unchallenged as controls. Three ml of inoculum was administered by intramammary infusion to the right quarters of each animal, containing $3.0 \times 10^7$ cfu/ml of an exponential-phase culture of *S. uberis* SU21 (clinical isolate obtained from Animal Health Laboratory, Alberta, Canada) suspended in 0.85% (w/v) saline. Milk samples were collected from all quarters, daily for 7 days post-challenge, for determination of SSC and bacteriology. All samples were stored on ice, and analyzed within 48 hrs of collection. Clinical assessments of animals included measurement of rectal temperatures, and udder swelling (visual and palpated). A numerical score of 1 (normal) to 3.5 (severe mastitis) was assigned to each animal and used as a means of comparing the severity of mastitis among vaccine groups. Milk quality was assessed by the presence of clots.

Serum IgG titers were determined at the time of first and second vaccinations, at 8 days before challenge (day 28), and at 11 days post-challenge (day 47). Similarly, milk IgG titers were determined at day 21 and 43. Serum IgA titers were determined at day 21 and 47, and milk IgA titers were determined at day 21 and 43. Round-bottomed, 96-well microtiter plates (Nunc) were coated overnight at 4° C. with CAMP-3, and (6×His)GapC of *S. uberis* and *S. dysgalactiae* (100 ng/well in 100 µl of carbonate buffer, pH 9.6), and blocked for 1 hr at 37° C. with 200 µl of PBSTg. 100 µl of test sample was added/well, and plates were incubated for 2 hrs at room temperature. After washing, alkaline phosphatase-conjugated goat anti-bovine IgG (H & L; Kirkegaard and Perry Labs. Inc., Gaithersburg, Md.) was added (100 µl/well), and plates were incubated for 1 hr at room temperature. Plates were washed, and alkaline phosphatase activity was detected at 405 nm following incubation with p-nitrophenyl phosphate in 1 M diethanolamine (pH 9.8) and 0.5 MM $MgCl_2$ for 1.5 hrs at room temperature.

Determination of milk IgG and IgA was carried out after treating milk with a commercially available rennin solution, as follows: one tablet of Rennet (CHR HANSEN) was dissolved in 40 ml of $H_2O$, and 0.1 ml of this solution was added to 2 ml of milk and incubated at room temperature for 4 hrs. Coagulated casein was pelleted by centrifugation at 3,000×g for 20 min, and the middle layer was removed (the top layer comprised fat) and analyzed as for serum samples. Both serum and milk titers were determined by the intersection of the least-square regression of the $OD_{405}$ versus logarithm of dilution with the $OD_{405}$ obtained from wells containing no serum.

Determination of SCC from milk samples was carried out at the Pacific Milk Analysis Laboratory (Chilliwak, British Columbia). Samples were collected in 14 ml polystyrene, round-bottomed tubes (Falcon) containing a preservative. SCC were fixed by mixing 0.5 ml of milk samples with 10 µl of fixative liquid (0.2 mg/ml eosine, 3.3% formaldehyde solution) for 18 hrs at 30° C. Samples were diluted 1/100 in emulsifier electrolyte solution (12% ethanol, 0.02% TRITON X-100, 0.1 M NaCl), and incubated at 80° C. for 10 min. After cooling to room temperature, SCC were determined with a Coulter counter. Repeated measures analysis of variance of SCC among treatments, and over time, was performed using the SYSTAT 10 software package (SPSS Science, Chicago, USA).

Table 3 shows pre- and post-challenge titers, presented as the arithmetic means of the natural log transformed values of serum titers from all animals in each treatment group (standard deviations in parentheses). Prior to vaccination, only 4 animals showed any detectable serum IgG titer against (6×His)GapC. Following vaccination, all animals vaccinated with (6×His)GapC showed a significant increase in both serum and milk anti-(6×His)GapC IgG titers, which consistently remained at least 10-fold higher than the control animals, while anti-(6×His)GapC IgG titers in animals vaccinated with CAMP-3 were similar to those of the control group. Anti-(6×His)GapC IgG titers in milk were consistently lower than the corresponding values in serum. However, immediately prior to challenge the increased serum and milk IgG titers in (6×His)GapC vaccinated animals, compared to control and CAMP-3 vaccinated animals, was apparent. Serum anti-(6×His)GapC IgA levels were detectable in all groups prior to challenge, but rose significantly following challenge. Even the CAMP-3 vaccinated group showed an increase in serum anti-(6×His)GapC IgA titers, most likely resulting from exposure to the cell surface-associated GapC of the S. uberis challenge bacteria. In CAMP-3 vaccinated animals, a post-challenge increase in anti-(6×His)GapC milk IgG titers was also observed, although a corresponding increase was not observed in serum IgG titers. In contrast to serum, milk anti-(6×His)GapC IgA was virtually undetectable in all groups, both pre- and post-challenge.

Following vaccination of cows with CAMP-3, there was a marked increase in serum and milk anti-CAMP IgG titers, compared to those of the control and (6×His)GapC vaccinated animals. Furthermore, in contrast to anti-(6×His)GapC IgG titers, anti-CAMP-3 titers increased post-challenge, whereas those for (6×His)GapC decreased slightly. Although the cause is unknown, this observation was consistent throughout all vaccine groups; post-challenge serum anti-(6×His)GapC IgG titers were found to have decreased, whereas the corresponding titers in milk had increased (with the exception of the S. dysgalactiae (6×His)GapC vaccinated group). Pre-challenge, serum anti-CAMP-3 IgA titers were higher than the equivalent serum anti-(6×His)GapC titers determined at the same time point (day 21), and at the time the post-challenge serum samples were taken, anti-CAMP-3 IgA levels had increased in all groups, most significantly in those vaccinated with CAMP-3. In contrast, both pre- and post-challenge milk anti-CAMP-3 IgA titers were virtually undetectable.

Following challenge with S. uberis SU21, at no point were bacteria recovered from any animals, vaccinated or otherwise. This is consistent with the results of a previous study (Finch et al. (1994) Infect. Immun. 62:3599–3603), where no bacteria were isolated following challenge from dairy cows vaccinated with heat-killed S. uberis, although bacteria were isolated from the unvaccinated control animals. It is possible that in the current study the inoculum administered was low enough to induce mastitis without causing persistent infection, even in unvaccinated animals. However, despite the absence of recoverable bacteria, animals did display clinical signs of disease, and SCC indicated that inflammation had occurred. Therefore, the challenge was deemed successful. Between vaccine groups, no significant differences were observed in rectal temperatures, and clinical scores determined that there were no significant differences in the severity of infection. Although no differences in milk yield were observed in any animals, the quality of milk was slightly affected in all groups, as discussed below.

Figure 28:
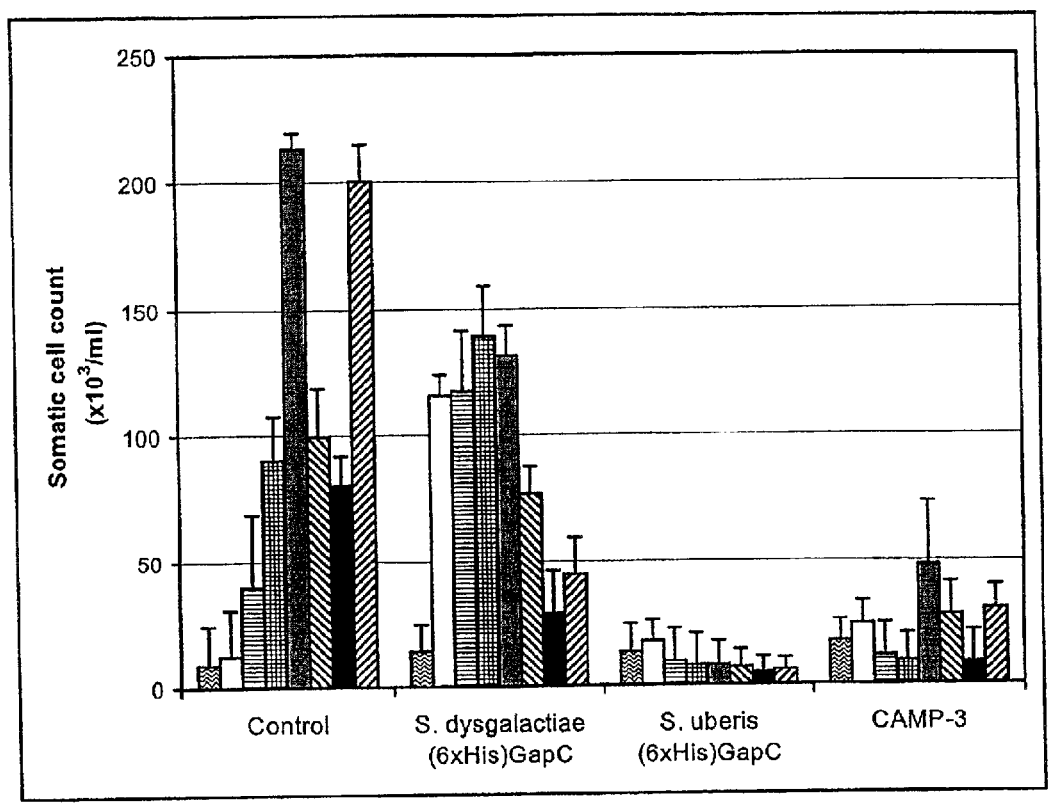
FIG. 28 shows the geometric mean SCC (plus 1 standard deviation) in quarters challenged with *S. uberis* in groups of cows as described in Example 6, for 7 days following challenge. Data sets correspond to day 0 (the far left bar), day 1 (the second bar from the left), day 2 (the third bar from the left), day 3 (the fourth bar from the left), day 4 (the fifth bar from the left), day 5 (the sixth bar from the left), day 6 (the seventh bar from the left), and day 7 (the eighth bar from the left). Despite the appearance of the figure, the SCC for *S. dysgalactiae* (6×His)GapC vaccinated animals on days 7 and 8, and CAMP-3 vaccinated animals on days 4 and 5 post-challenge were not statistically significantly different from those of the control.

The bovine udder is comprised of unconnected quarters, and by challenging only 2 quarters with S. uberis an internal control was provided for each animal. FIG. 28 shows SCC over the course of the trial, for each particular vaccine group. On initial analysis, the reported SCC of the control group appeared somewhat variable; however, the overall relationship was an increase of SCC over time, explained by a quadratic relationship (p=0.02). After day 2, SCC of the control group increased markedly, reaching their highest level at day 4 post-challenge. SCC then decreased slightly, before rising markedly again by day 7 post-challenge. This somewhat erratic trend is consistent with SCC values reported elsewhere, following challenge of lactating cows with S. uberis (Finch et al. (1997) Vaccine 15:1138–1143; Finch et al. (1994) Infect. Immun. 62:3599–3603). The SCC of S. dysgalactiae (6×His)GapC vaccinated animals increased sharply immediately post-challenge, reaching a maximum at day 3, before decreasing erratically over the remainder of the trial. Nevertheless, at no point was the decrease in SCC statistically significantly different from that of the control group, despite an apparent difference from day 4 post-challenge onward. This result may be because the S. dysgalactiae (6×His)GapC is not as protective as that of S. uberis.

Vaccination with S. uberis (6×His)GapC resulted in a significant decrease in SCC, compared to the control group. From day 3 onward, SCC in this group were statistically significantly lower than those of the control group (p values of 0.023 at day 3, 0.001 at day 4, 0.011 at day 5, 0.006 at day 6, and 0.000 at day 7 post-challenge). SCC of cows vaccinated with the CAMP-3 antigen were slightly higher than those of the *S. uberis* (6×His)GapC vaccinated animals, although they were still clearly lower than those of the control group. Comparison of SCC of the control and CAMP-3 vaccinated groups revealed statistically significant differences at days 3 (p value of 0.033), 6 and 7 post-challenge (p values of 0.032, and 0.046 respectively), but not at days 4 and 5, even though SCC were obviously lower in the CAMP-3 vaccinated group on these days. Following challenge with SU21, the time that milk quality remained affected varied between vaccine groups. Post-challenge, milk quality in the control, *S. dysgalactiae* (6×His)GapC, CAMP-3, and *S. uberis* (6×His)GapC vaccinated groups was reduced for a total of 21, 24, 11, and 9 days respectively. According to this data, mastitis in the *S. dysgalactiae* (6×His)GapC vaccinated group was no less severe, if not worse, than that of the control group. Conversely, although vaccination with *S. uberis* (6×His)GapC did not completely prevent reduced milk quality, it did significantly reduce the length of time that milk quality was affected. Vaccination with CAMP-3 also appeared to reduce the length of time that milk quality was reduced, although not as much as in the *S. uberis* (6×His)GapC group, which is in keeping with the SCC results.

Thus, vaccination with *S. uberis* (6×His)GapC resulted in significant protection against heterologous challenge and *S. uberis* GapC is therefore suitable for use as a vaccine antigen against *S. uberis* mastitis, as well as against mastitis caused by heterologous strains.

TABLE 3

Anti-GapC and anti-CAMP IgG and IgA titers[a]

| Antigen | | Group | IgG titers | | IgA titers | |
|---|---|---|---|---|---|---|
| | | | Serum | Milk | Serum | Milk |
| GapC | Pre-challenge | 1 | 8.33 (±0.87) | 4.28 (±0.55) | 2.75 (±0.85) | 0.86 (±1.10) |
| | | 2 | 12.74 (±1.64) | 7.12 (±0.34) | 3.39 (±0.31) | 2.11 (±1.22) |
| | | 3 | 13.21 (±0.84) | 7.85 (±1.09) | 2.72 (±1.50) | 1.24 (±1.33) |
| | | 4 | 9.41 (±0.69) | 4.51 ± 0.61 | 2.09 (±1.03) | 1.34 (±1.26) |
| | Post-challenge | 1 | 2.42 (±3.75) | 6.38 (±0.55) | 4.20 (±0.97) | 1.35 (±1.55) |
| | | 2 | 10.12 (±1.34) | 6.66 (±0.22) | 4.78 (±0.94) | 1.14 (±1.25) |
| | | 3 | 10.79 (±1.07) | 9.05 (±1.64) | 4.64 (±1.02) | 1.31 (±1.22) |
| | | 4 | 5.30 (±4.14) | 5.84 (±0.46) | 3.49 (±3.28) | 1.80 (±1.25) |
| CAMP | Pre-challenge | 1 | 7.35 (±1.00) | 4.06 (±0.39) | 1.63 (±1.53) | 0.60 (±0.81) |
| | | 2 | 7.98 (±0.98) | 5.33 (±0.34) | 0.90 (±1.36) | 1.77 (±0.90) |
| | | 3 | 7.21 (±0.99) | 5.06 (±0.70) | 2.56 (±1.90) | 1.67 (±1.42) |
| | | 4 | 11.82 (±0.59) | 8.37 (±1.02) | 3.69 (±2.31) | 1.46 (±1.44) |
| | Post-challenge | 1 | 6.19 (±4.82) | 4.87 (±1.37) | 0 | 0.58 (±0.94) |
| | | 2 | 6.98 (±3.52) | 5.07 (±0.78) | 1.46 (±2.42) | 0.41 (±0.99) |
| | | 3 | 6.41 (±5.24) | 5.26 (±1.00) | 2.66 (±2.24) | 1.85 (±1.42) |
| | | 4 | 13.47 (±0.55) | 8.90 (±1.13) | 5.09 (±1.42) | 1.90 (±1.30) |

[a]Groups shown are 1. Control, 2. *S. dysgalactiae* (6xHis)GapC, 3.*S. uberis* (6xHis)GapC, and 4. CAMP-3 vaccinates. Pre-challenge data correspond to serum IgG titers at day 28, and serum IgA, milk IgG and IgA titers at day 21. Post-challenge data correspond to serum IgG titers at day 47, and serum IgA, milk IgG and IgA titers at day 43.

Thus, the cloning, expression and characterization of various GapC plasmin binding proteins is disclosed, as are methods of using the same. Although preferred embodiments of the subject invention have been described in some detail, it is understood that obvious variations can be made without departing from the spirit and the scope of the invention as defined by the appended claims.

What is claimed is:

1. An isolated wherein the protein is a *Streptococcus uberis* GapC protein comprising the amino acid sequence SEQ ID NO:8.

2. A vaccine composition comprising a pharmaceutically acceptable vehicle and the isolated GapC protein of claim 1.

3. The vaccine composition of claim 2, further comprising an adjuvant.

4. A method of producing a vaccine composition comprising the steps of (1) providing the GapC protein according to claim 2; and (2) combining said GapC protein with a pharmaceutically acceptable vehicle.

5. An immunodiagnostic test kit for detecting *Streptococcus uberis* infection, said test kit comprising the GapC protein, of claim 1, and instructions for conducting the immunodiagnostic test.

* * * * *

UNITED STATES PATENT AND TRADEMARK OFFICE
CERTIFICATE OF CORRECTION

PATENT NO. : 6,833,134 B2 Page 1 of 1
APPLICATION NO. : 10/134297
DATED : December 21, 2004
INVENTOR(S) : Alexandra J. Bolton et al.

It is certified that error appears in the above-identified patent and that said Letters Patent is hereby corrected as shown below:

Claim 1 delete "wherein the protein is a"

Signed and Sealed this

Twelfth Day of December, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 37
<212> TYPE: DNA
<213> ORGANISM: Artificial Sequence
<220> FEATURE:
<223> OTHER INFORMATION: Description of Artificial Sequence: primer
      gapC1

<400> SEQUENCE: 1
ggcggcggca tatggtagtt aaagttggta ttaacgg                           37

<210> SEQ ID NO 2
<211> LENGTH: 35
<212> TYPE: DNA
<213> ORGANISM: Artificial Sequence
<220> FEATURE:

-continued

<223> OTHER INFORMATION: Description of Artificial Sequence: primer
      gapC1r

<400> SEQUENCE: 2
gcggatcctt atttagcgat ttttgcaaag tactc                            35

<210> SEQ ID NO 3
<211> LENGTH: 1011
<212> TYPE: DNA
<213> ORGANISM: Streptococcus dysgalactiae
<220> FEATURE:
<221> NAME/KEY: CDS
<222> LOCATION: (1)..(1011)

<400> SEQUENCE: 3

```
atg gta gtt aaa gtt ggt att aac ggt ttc ggt cgt atc gga cgt ctt        48
Met Val Val Lys Val Gly Ile Asn Gly Phe Gly Arg Ile Gly Arg Leu
  1               5                  10                  15 gca ttc cgt cgt att caa aat gtt gaa ggt gtt gaa gta act cgt atc        96
Ala Phe Arg Arg Ile Gln Asn Val Glu Gly Val Glu Val Thr Arg Ile
             20                  25                  30 aac gac ctt aca gat cca aac atg ctt gca cac ttg ttg aaa tac gat       144
Asn Asp Leu Thr Asp Pro Asn Met Leu Ala His Leu Leu Lys Tyr Asp
         35                  40                  45 aca act caa gga cgt ttt gac gga act gtt gaa gtt aaa gaa ggt gga       192
Thr Thr Gln Gly Arg Phe Asp Gly Thr Val Glu Val Lys Glu Gly Gly
     50                  55                  60 ttt gaa gta aac gga aac ttc atc aaa gtt tct gct gaa cgt gat cca       240
Phe Glu Val Asn Gly Asn Phe Ile Lys Val Ser Ala Glu Arg Asp Pro
 65                  70                  75                  80 gaa aac atc gac tgg gca act gac ggt gtt gaa atc gtt ctg gaa gca       288
Glu Asn Ile Asp Trp Ala Thr Asp Gly Val Glu Ile Val Leu Glu Ala
                 85                  90                  95 act ggt ttc ttt gct aaa aaa gaa gct gct gaa aaa cac tta cat gct       336
Thr Gly Phe Phe Ala Lys Lys Glu Ala Ala Glu Lys His Leu His Ala
            100                 105                 110 aac ggt gct aaa aaa gtt gtt atc aca gct cct ggt gga aac gac gtt       384
Asn Gly Ala Lys Lys Val Val Ile Thr Ala Pro Gly Gly Asn Asp Val
        115                 120                 125 aaa aca gtt gtt ttc aac act aac cac gac att ctt gac ggt act gaa       432
Lys Thr Val Val Phe Asn Thr Asn His Asp Ile Leu Asp Gly Thr Glu
    130                 135                 140 aca gtt atc tca ggt gct tca tgt act aca aac tgt tta gct cct atg       480
Thr Val Ile Ser Gly Ala Ser Cys Thr Thr Asn Cys Leu Ala Pro Met
145                 150                 155                 160 gct aaa gct ctt cac gat gca ttt ggt atc caa aaa ggt ctt atg act       528
Ala Lys Ala Leu His Asp Ala Phe Gly Ile Gln Lys Gly Leu Met Thr
                165                 170                 175 aca atc cac gct tat act ggt gac caa atg atc ctt gac gga cca cac       576
Thr Ile His Ala Tyr Thr Gly Asp Gln Met Ile Leu Asp Gly Pro His
            180                 185                 190 cgt ggt ggt gac ctt cgt cgt gct cgt gct ggt gct gca aac att gtt       624
Arg Gly Gly Asp Leu Arg Arg Ala Arg Ala Gly Ala Ala Asn Ile Val
        195                 200                 205 cct aac tca act ggt gct gct aaa gct atc ggt ctt gtt atc cca gaa       672
Pro Asn Ser Thr Gly Ala Ala Lys Ala Ile Gly Leu Val Ile Pro Glu
    210                 215                 220 ttg aat ggt aaa ctt gat ggt gct gca caa cgt gtt cct gtt cca act       720
Leu Asn Gly Lys Leu Asp Gly Ala Ala Gln Arg Val Pro Val Pro Thr
225                 230                 235                 240 gga tca gta act gag ttg gtt gta act ctt gat aaa aac gtt tct gtt       768
Gly Ser Val Thr Glu Leu Val Val Thr Leu Asp Lys Asn Val Ser Val
```

```
Gly Ser Val Thr Glu Leu Val Val Thr Leu Asp Lys Asn Val Ser Val
                245                 250                 255 gac gaa atc aac gct gct atg aaa gct gct tca aac gac agt ttc ggt    816
Asp Glu Ile Asn Ala Ala Met Lys Ala Ala Ser Asn Asp Ser Phe Gly
            260                 265                 270 tac act gaa gat cca att gtt tct tca gat atc gta ggc gtg tca tac    864
Tyr Thr Glu Asp Pro Ile Val Ser Ser Asp Ile Val Gly Val Ser Tyr
        275                 280                 285 ggt tca ttg ttt gac gca act caa act aaa gtt atg gaa gtt gac gga    912
Gly Ser Leu Phe Asp Ala Thr Gln Thr Lys Val Met Glu Val Asp Gly
    290                 295                 300 tca caa ttg gtt aaa gtt gta tca tgg tat gac aat gaa atg tct tac    960
Ser Gln Leu Val Lys Val Val Ser Trp Tyr Asp Asn Glu Met Ser Tyr
305                 310                 315                 320 act gct caa ctt gtt cgt aca ctt gag tac ttt gca aaa atc gct aaa   1008
Thr Ala Gln Leu Val Arg Thr Leu Glu Tyr Phe Ala Lys Ile Ala Lys
                325                 330                 335 taa                                                                1011

<210> SEQ ID NO 4
<211> LENGTH: 336
<212> TYPE: PRT
<213> ORGANISM: Streptococcus dysgalactiae

<400> SEQUENCE: 4

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
            20                  25                  30

Asn Asp Leu Thr Asp Pro Asn Met Leu Ala His Leu Leu Lys Tyr Asp
        35                  40                  45

Thr Thr Gln Gly Arg Phe Asp Gly Thr Val Glu Val Lys Glu Gly Gly
    50                  55                  60

Phe Glu Val Asn Gly Asn Phe Ile Lys Val Ser Ala Glu Arg Asp Pro
65                  70                  75                  80

Glu Asn Ile Asp Trp Ala Thr Asp Gly Val Glu Ile Val Leu Glu Ala
                85                  90                  95

Thr Gly Phe Phe Ala Lys Lys Glu Ala Ala Glu Lys His Leu His Ala
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu His Asp Ala Phe Gly Ile Gln Lys Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ala Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Val Thr Leu Asp Lys Asn Val Ser Val
```

```
                     245                 250                 255
    Asp Glu Ile Asn Ala Ala Met Lys Ala Ala Ser Asn Asp Ser Phe Gly
                 260                 265                 270

Tyr Thr Glu Asp Pro Ile Val Ser Ser Asp Ile Val Gly Val Ser Tyr
                 275                 280                 285

Gly Ser Leu Phe Asp Ala Thr Gln Thr Lys Val Met Glu Val Asp Gly
                 290                 295                 300

Ser Gln Leu Val Lys Val Ser Trp Tyr Asp Asn Glu Met Ser Tyr
    305                 310                 315                 320

Thr Ala Gln Leu Val Arg Thr Leu Glu Tyr Phe Ala Lys Ile Ala Lys
                 325                 330                 335

<210> SEQ ID NO 5
<211> LENGTH: 1011
<212> TYPE: DNA
<213> ORGANISM: Streptococcus agalactiae
<220> FEATURE:
<221> NAME/KEY: CDS
<222> LOCATION: (1)..(1011)

<400> SEQUENCE: 5 atg gta gtt aaa gtt ggt att aac ggt ttc ggt cgt atc ggt cgt ctt      48
Met Val Val Lys Val Gly Ile Asn Gly Phe Gly Arg Ile Gly Arg Leu
  1               5                  10                  15 gca ttc cgt cgc atc caa aac gta gaa ggt gtt gaa gtt act cgt atc      96
Ala Phe Arg Arg Ile Gln Asn Val Glu Gly Val Glu Val Thr Arg Ile
                 20                  25                  30 aac gac ctt aca gat cca aac atg ctt gca cac ttg ttg aaa tat gac     144
Asn Asp Leu Thr Asp Pro Asn Met Leu Ala His Leu Leu Lys Tyr Asp
             35                  40                  45 aca act caa ggt cgt ttc gac ggt act gtt gaa gtt aaa gaa ggt gga     192
Thr Thr Gln Gly Arg Phe Asp Gly Thr Val Glu Val Lys Glu Gly Gly
         50                  55                  60 ttc gaa gtt aac ggt caa ttt gtt aaa gtt tct gct gaa cgc gaa cca     240
Phe Glu Val Asn Gly Gln Phe Val Lys Val Ser Ala Glu Arg Glu Pro
 65                  70                  75                  80 gca aac att gac tgg gct act gat ggc gta gaa atc gtt ctt gaa gca     288
Ala Asn Ile Asp Trp Ala Thr Asp Gly Val Glu Ile Val Leu Glu Ala
                 85                  90                  95 act ggt ttc ttt gca tca aaa gaa aaa gct gga caa cac atc cat gaa     336
Thr Gly Phe Phe Ala Ser Lys Glu Lys Ala Gly Gln His Ile His Glu
            100                 105                 110 aat ggt gct aaa aaa gtt gtt atc aca gct cct ggt gga aac gac gtt     384
Asn Gly Ala Lys Lys Val Val Ile Thr Ala Pro Gly Gly Asn Asp Val
        115                 120                 125 aaa aca gtt gtt ttc aac act aac cac gat atc ctt gat gga act gaa     432
Lys Thr Val Val Phe Asn Thr Asn His Asp Ile Leu Asp Gly Thr Glu
    130                 135                 140 aca gtt atc tca ggt gct tca tgt act aca aac tgt ctt gct cca atg     480
Thr Val Ile Ser Gly Ala Ser Cys Thr Thr Asn Cys Leu Ala Pro Met
145                 150                 155                 160 gct aaa gct tta caa gac aac ttt ggt gtt aaa caa ggt ttg atg act     528
Ala Lys Ala Leu Gln Asp Asn Phe Gly Val Lys Gln Gly Leu Met Thr
                165                 170                 175 act atc cac gca tac act ggt gac caa atg atc ctt gac gga cca cac     576
Thr Ile His Ala Tyr Thr Gly Asp Gln Met Ile Leu Asp Gly Pro His
            180                 185                 190 cgt ggt ggt gac ctt cgt cgt gct cgt gca ggt gct gca aac atc gtt     624
Arg Gly Gly Asp Leu Arg Arg Ala Arg Ala Gly Ala Ala Asn Ile Val
        195                 200                 205
```

```
cct aac tca act ggt gct gca aaa gct atc gga ctt gtt atc cca gaa      672
Pro Asn Ser Thr Gly Ala Ala Lys Ala Ile Gly Leu Val Ile Pro Glu
    210                 215                 220 ttg aac ggt aaa ctt gat ggt gct gca caa cgt gtt cct gtt cca act      720
Leu Asn Gly Lys Leu Asp Gly Ala Ala Gln Arg Val Pro Val Pro Thr
225                 230                 235                 240 gga tca gta act gaa ttg gtt gca act ctt gaa aaa gac gta act gtc      768
Gly Ser Val Thr Glu Leu Val Ala Thr Leu Glu Lys Asp Val Thr Val
                245                 250                 255 gaa gaa gta aat gca gct atg aaa gca gca gct aac gat tca tac ggt      816
Glu Glu Val Asn Ala Ala Met Lys Ala Ala Ala Asn Asp Ser Tyr Gly
            260                 265                 270 tat act gaa gat cca atc gta tca tct gat atc gtt ggt att tca tac      864
Tyr Thr Glu Asp Pro Ile Val Ser Ser Asp Ile Val Gly Ile Ser Tyr
        275                 280                 285 ggt tca ttg ttt gat gct act caa act aaa gtt caa act gtt gac ggt      912
Gly Ser Leu Phe Asp Ala Thr Gln Thr Lys Val Gln Thr Val Asp Gly
    290                 295                 300 aac caa ttg gtt aaa gtt gtt tca tgg tac gat aac gaa atg tca tac      960
Asn Gln Leu Val Lys Val Val Ser Trp Tyr Asp Asn Glu Met Ser Tyr
305                 310                 315                 320 act tca caa ctt gtt cgt aca ctt gag tac ttt gca aaa atc gct aaa     1008
Thr Ser Gln Leu Val Arg Thr Leu Glu Tyr Phe Ala Lys Ile Ala Lys
                325                 330                 335 taa                                                                 1011
```

<210> SEQ ID NO 6
<211> LENGTH: 336
<212> TYPE: PRT
<213> ORGANISM: Streptococcus agalactiae

<400> SEQUENCE: 6

```
Met Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
             20                  25                  30

Asn Asp Leu Thr Asp Pro Asn Met Leu Ala His Leu Leu Lys Tyr Asp
         35                  40                  45

Thr Thr Gln Gly Arg Phe Asp Gly Thr Val Glu Val Lys Glu Gly Gly
     50                  55                  60

Phe Glu Val Asn Gly Gln Phe Val Lys Val Ser Ala Glu Arg Glu Pro
 65                  70                  75                  80

Ala Asn Ile Asp Trp Ala Thr Asp Gly Val Glu Ile Val Leu Glu Ala
                 85                  90                  95

Thr Gly Phe Phe Ala Ser Lys Glu Lys Ala Gly Gln His Ile His Glu
            100                 105                 110

Asn Gly Ala Lys Lys Val Val Ile Thr Ala Pro Gly Gly Asn Asp Val
        115                 120                 125

Lys Thr Val Val Phe Asn Thr Asn His Asp Ile Leu Asp Gly Thr Glu
    130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
            180                 185                 190
```

```
Arg Gly Gly Asp Leu Arg Arg Ala Arg Ala Gly Ala Ala Asn Ile Val
            195                 200                 205

Pro Asn Ser Thr Gly Ala Ala Lys Ala Ile Gly Leu Val Ile Pro Glu
210                 215                 220

Leu Asn Gly Lys Leu Asp Gly Ala Ala Gln Arg Val Pro Val Pro Thr
225                 230                 235                 240

Gly Ser Val Thr Glu Leu Val Ala Thr Leu Glu Lys Asp Val Thr Val
                245                 250                 255

Glu Glu Val Asn Ala Ala Met Lys Ala Ala Asn Asp Ser Tyr Gly
            260                 265                 270

Tyr Thr Glu Asp Pro Ile Val Ser Asp Ile Val Gly Ile Ser Tyr
        275                 280                 285

Gly Ser Leu Phe Asp Ala Thr Gln Thr Lys Val Gln Thr Val Asp Gly
290                 295                 300

Asn Gln Leu Val Lys Val Ser Trp Tyr Asp Asn Glu Met Ser Tyr
305                 310                 315                 320

Thr Ser Gln Leu Val Arg Thr Leu Glu Tyr Phe Ala Lys Ile Ala Lys
                325                 330                 335
```

<210> SEQ ID NO 7
<211> LENGTH: 1011
<212> TYPE: DNA
<213> ORGANISM: Streptococcus uberis
<220> FEATURE:
<221> NAME/KEY: CDS
<222> LOCATION: (1)..(1011)

<400> SEQUENCE: 7

```
atg gta gtt aaa gtt ggt att aac ggt ttc ggt cgt atc gga cgt ctt      48
Met Val Val Lys Val Gly Ile Asn Gly Phe Gly Arg Ile Gly Arg Leu
  1               5                  10                  15 gca ttc cgt cgt att caa aac gtt gaa ggt gtt gaa gta act cgt att      96
Ala Phe Arg Arg Ile Gln Asn Val Glu Gly Val Glu Val Thr Arg Ile
                 20                  25                  30 aac gat ctt act gac cca aat atg ctt gca cac ttg ttg aaa tat gat     144
Asn Asp Leu Thr Asp Pro Asn Met Leu Ala His Leu Leu Lys Tyr Asp
             35                  40                  45 aca act caa ggt cgt ttc gac ggt aca gtt gaa gtt aaa gat ggt gga     192
Thr Thr Gln Gly Arg Phe Asp Gly Thr Val Glu Val Lys Asp Gly Gly
         50                  55                  60 ttc gaa gtt aac gga aac ttc atc aaa gtt tct gct gaa aaa gat cca     240
Phe Glu Val Asn Gly Asn Phe Ile Lys Val Ser Ala Glu Lys Asp Pro
 65                  70                  75                  80 gaa aac att gac tgg gca act gac ggt gta gaa atc gtt ctt gaa gca     288
Glu Asn Ile Asp Trp Ala Thr Asp Gly Val Glu Ile Val Leu Glu Ala
                 85                  90                  95 act ggt ttc ttt gct aaa aaa gca gct gct gaa aaa cat tta cat gct     336
Thr Gly Phe Phe Ala Lys Lys Ala Ala Ala Glu Lys His Leu His Ala
            100                 105                 110 aac ggt gct aaa aaa gtt gtt atc aca gct cct ggt gga gat gat gtt     384
Asn Gly Ala Lys Lys Val Val Ile Thr Ala Pro Gly Gly Asp Asp Val
        115                 120                 125 aaa act gtt gta ttt aac aca aac cat gac att ctt gac ggt aca gaa     432
Lys Thr Val Val Phe Asn Thr Asn His Asp Ile Leu Asp Gly Thr Glu
    130                 135                 140 act gta att tca ggt gct tca tgt act act aac tgt tta gct cca atg     480
Thr Val Ile Ser Gly Ala Ser Cys Thr Thr Asn Cys Leu Ala Pro Met
145                 150                 155                 160 gct aaa gct ttg caa gat aac ttt ggt gtt aaa caa ggt ttg atg aca     528
Ala Lys Ala Leu Gln Asp Asn Phe Gly Val Lys Gln Gly Leu Met Thr
```

```
                                                                            -continued Ala Lys Ala Leu Gln Asp Asn Phe Gly Val Lys Gln Gly Leu Met Thr
                165                 170                 175 act atc cac gct tac act ggt gac caa atg atc ctt gac gga cca cac    576
Thr Ile His Ala Tyr Thr Gly Asp Gln Met Ile Leu Asp Gly Pro His
            180                 185                 190 cgt ggt ggt gac ctt cgt cgt gct cgt gct ggt gca agc aac att gtt    624
Arg Gly Gly Asp Leu Arg Arg Ala Arg Ala Gly Ala Ser Asn Ile Val
        195                 200                 205 cct aac tca act ggt gct gct aaa gca atc ggt ctt gta atc cca gaa    672
Pro Asn Ser Thr Gly Ala Ala Lys Ala Ile Gly Leu Val Ile Pro Glu
    210                 215                 220 tta aat ggt aaa ctt gac ggt gct gca caa cgt gtt cct gtt cca act    720
Leu Asn Gly Lys Leu Asp Gly Ala Ala Gln Arg Val Pro Val Pro Thr
225                 230                 235                 240 gga tca gta act gaa tta gta gca gtt ctt gaa aaa gaa act tca gtt    768
Gly Ser Val Thr Glu Leu Val Ala Val Leu Glu Lys Glu Thr Ser Val
                245                 250                 255 gaa gaa atc aac gca gca atg aaa gca gct gca aac gat tca tac gga    816
Glu Glu Ile Asn Ala Ala Met Lys Ala Ala Ala Asn Asp Ser Tyr Gly
            260                 265                 270 tac act gaa gac cca atc gta tct tct gat atc atc ggt atg gct tac    864
Tyr Thr Glu Asp Pro Ile Val Ser Ser Asp Ile Ile Gly Met Ala Tyr
        275                 280                 285 ggt tca ttg ttt gat gct act caa act aaa gta caa act gtt gat gga    912
Gly Ser Leu Phe Asp Ala Thr Gln Thr Lys Val Gln Thr Val Asp Gly
    290                 295                 300 aat caa tta gtt aaa gtt gtt tca tgg tat gac aac gaa atg tct tac    960
Asn Gln Leu Val Lys Val Val Ser Trp Tyr Asp Asn Glu Met Ser Tyr
305                 310                 315                 320 act gca caa ctt gtt cgt act ctt gag tac ttt gca aaa atc gct aaa   1008
Thr Ala Gln Leu Val Arg Thr Leu Glu Tyr Phe Ala Lys Ile Ala Lys
                325                 330                 335 taa                                                                1011

<210> SEQ ID NO 8
<211> LENGTH: 336
<212> TYPE: PRT
<213> ORGANISM: Streptococcus uberis

<400> SEQUENCE: 8

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
                20                  25                  30

Asn Asp Leu Thr Asp Pro Asn Met Leu Ala His Leu Leu Lys Tyr Asp
            35                  40                  45

Thr Thr Gln Gly Arg Phe Asp Gly Thr Val Glu Val Lys Asp Gly Gly
        50                  55                  60

Phe Glu Val Asn Gly Asn Phe Ile Lys Val Ser Ala Glu Lys Asp Pro
65                  70                  75                  80

Glu Asn Ile Asp Trp Ala Thr Asp Gly Val Glu Ile Val Leu Glu Ala
                85                  90                  95

Thr Gly Phe Phe Ala Lys Lys Ala Ala Ala Glu Lys His Leu His Ala
                100                 105                 110

Asn Gly Ala Lys Lys Val Val Ile Thr Ala Pro Gly Gly Asp Asp Val
            115                 120                 125

Lys Thr Val Val Phe Asn Thr Asn His Asp Ile Leu Asp Gly Thr Glu
        130                 135                 140
```

```
Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Ala Tyr Thr Gly Asp Gln Met Ile Leu Asp Gly Pro His
            180                 185                 190

Arg Gly Gly Asp Leu Arg Arg Ala Arg Ala Gly Ala Ser Asn Ile Val
        195                 200                 205

Pro Asn Ser Thr Gly Ala Ala Lys Ala Ile Gly Leu Val Ile Pro Glu
    210                 215                 220

Leu Asn Gly Lys Leu Asp Gly Ala Ala Gln Arg Val Pro Val Pro Thr
225                 230                 235                 240

Gly Ser Val Thr Glu Leu Val Ala Val Leu Glu Lys Glu Thr Ser Val
                245                 250                 255

Glu Glu Ile Asn Ala Ala Met Lys Ala Ala Asn Asp Ser Tyr Gly
            260                 265                 270

Tyr Thr Glu Asp Pro Ile Val Ser Ser Asp Ile Ile Gly Met Ala Tyr
        275                 280                 285

Gly Ser Leu Phe Asp Ala Thr Gln Thr Lys Val Gln Thr Val Asp Gly
    290                 295                 300

Asn Gln Leu Val Lys Val Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
                325                 330                 335

<210> SEQ ID NO 9
<211> LENGTH: 1011
<212> TYPE: DNA
<213> ORGANISM: Streptococcus parauberis
<220> FEATURE:
<221> NAME/KEY: CDS
<222> LOCATION: (1)..(1011)

<400> SEQUENCE: 9 atg gta gtt aaa gtt ggt att aac ggt ttt ggc cgt atc gga cgt ctt        48
Met Val Val Lys Val Gly Ile Asn Gly Phe Gly Arg Ile Gly Arg Leu
  1               5                  10                  15 gct ttc cgt cgt att caa aat gta gaa ggt gtt gaa gtt act cgc atc        96
Ala Phe Arg Arg Ile Gln Asn Val Glu Gly Val Glu Val Thr Arg Ile
                 20                  25                  30 aac gac ctt aca gat cca aat atg ctt gca cac ttg tta aaa tac gat       144
Asn Asp Leu Thr Asp Pro Asn Met Leu Ala His Leu Leu Lys Tyr Asp
             35                  40                  45 aca act caa ggt cgt ttt gac ggt act gta gaa gtt aaa gat ggt gga       192
Thr Thr Gln Gly Arg Phe Asp Gly Thr Val Glu Val Lys Asp Gly Gly
         50                  55                  60 ttt gac gtt aac gga aaa ttc att aaa gtt tct gct gaa aaa gat cca       240
Phe Asp Val Asn Gly Lys Phe Ile Lys Val Ser Ala Glu Lys Asp Pro
 65                  70                  75                  80 gaa caa att gac tgg gca act gac ggt gtt gaa atc gtt ctt gaa gca       288
Glu Gln Ile Asp Trp Ala Thr Asp Gly Val Glu Ile Val Leu Glu Ala
                 85                  90                  95 act ggt ttc ttt gct aaa aaa gca gct gct gaa aaa cat tta cat gaa       336
Thr Gly Phe Phe Ala Lys Lys Ala Ala Ala Glu Lys His Leu His Glu
                100                 105                 110 aat ggt gct aaa aaa gtt gtt atc act gct cct ggt gga gat gac gtg       384
Asn Gly Ala Lys Lys Val Val Ile Thr Ala Pro Gly Gly Asp Asp Val
            115                 120                 125
```

```
aaa aca gtt gta ttt aac act aac cat gat atc ctt gat gga act gaa      432
Lys Thr Val Val Phe Asn Thr Asn His Asp Ile Leu Asp Gly Thr Glu
    130                 135                 140 aca gtt att tca ggt gct tca tgt act aca aac tgt tta gct cca atg      480
Thr Val Ile Ser Gly Ala Ser Cys Thr Thr Asn Cys Leu Ala Pro Met
145                 150                 155                 160 gct aaa gct tta caa gat aac ttt ggc gta aaa caa ggt tta atg act      528
Ala Lys Ala Leu Gln Asp Asn Phe Gly Val Lys Gln Gly Leu Met Thr
                165                 170                 175 aca atc cac gct tac act ggt gat caa atg ctt ctt gat gga cct cac      576
Thr Ile His Ala Tyr Thr Gly Asp Gln Met Leu Leu Asp Gly Pro His
            180                 185                 190 cgt ggt ggt gac tta cgt cgt gcc cgt gct ggt gct aac aat att gtt      624
Arg Gly Gly Asp Leu Arg Arg Ala Arg Ala Gly Ala Asn Asn Ile Val
        195                 200                 205 cct aac tca act ggt gct gct aaa gca atc ggt ctt gtt atc cct gaa      672
Pro Asn Ser Thr Gly Ala Ala Lys Ala Ile Gly Leu Val Ile Pro Glu
    210                 215                 220 tta aat ggt aaa ctt gac ggt gct gca caa cgt gta cca gtt cca aca      720
Leu Asn Gly Lys Leu Asp Gly Ala Ala Gln Arg Val Pro Val Pro Thr
225                 230                 235                 240 ggt tca gta aca gaa tta gta gca gtt ctt aat aaa gaa act tca gta      768
Gly Ser Val Thr Glu Leu Val Ala Val Leu Asn Lys Glu Thr Ser Val
                245                 250                 255 gaa gaa att aac tca gta atg aaa gct gca gct aat gat tca tat ggt      816
Glu Glu Ile Asn Ser Val Met Lys Ala Ala Ala Asn Asp Ser Tyr Gly
            260                 265                 270 tac act gaa gat cca atc gta tca tct gat atc gtt ggt atg tct ttc      864
Tyr Thr Glu Asp Pro Ile Val Ser Ser Asp Ile Val Gly Met Ser Phe
        275                 280                 285 ggt tca tta ttc gat gct act caa act aaa gta caa act gtt gat gga      912
Gly Ser Leu Phe Asp Ala Thr Gln Thr Lys Val Gln Thr Val Asp Gly
    290                 295                 300 aat caa tta gtt aaa gtt gtt tca tgg tat gac aat gaa atg tct tac      960
Asn Gln Leu Val Lys Val Val Ser Trp Tyr Asp Asn Glu Met Ser Tyr
305                 310                 315                 320 act gct caa ctt gat cgt aca ctt gag tac ttt gca aaa atc gct aaa     1008
Thr Ala Gln Leu Asp Arg Thr Leu Glu Tyr Phe Ala Lys Ile Ala Lys
                325                 330                 335 taa                                                                 1011

<210> SEQ ID NO 10
<211> LENGTH: 336
<212> TYPE: PRT
<213> ORGANISM: Streptococcus parauberis

<400> SEQUENCE: 10

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
                20                  25                  30

Asn Asp Leu Thr Asp Pro Asn Met Leu Ala His Leu Leu Lys Tyr Asp
            35                  40                  45

Thr Thr Gln Gly Arg Phe Asp Gly Thr Val Glu Val Lys Asp Gly Gly
        50                  55                  60

Phe Asp Val Asn Gly Lys Phe Ile Lys Val Ser Ala Glu Lys Asp Pro
65                  70                  75                  80

Glu Gln Ile Asp Trp Ala Thr Asp Gly Val Glu Ile Val Leu Glu Ala
```

```
                         85                  90                  95
Thr Gly Phe Phe Ala Lys Lys Ala Ala Glu Lys His Leu His Glu
               100                 105                 110
Asn Gly Ala Lys Lys Val Val Ile Thr Ala Pro Gly Gly Asp Asp Val
               115                 120                 125
Lys Thr Val Val Phe Asn Thr Asn His Asp Ile Leu Asp Gly Thr Glu
               130                 135                 140
Thr Val Ile Ser Gly Ala Ser Cys Thr Thr Asn Cys Leu Ala Pro Met
145                 150                 155                 160
Ala Lys Ala Leu Gln Asp Asn Phe Gly Val Lys Gln Gly Leu Met Thr
                   165                 170                 175
Thr Ile His Ala Tyr Thr Gly Asp Gln Met Leu Leu Asp Gly Pro His
                   180                 185                 190
Arg Gly Gly Asp Leu Arg Arg Ala Arg Ala Gly Ala Asn Asn Ile Val
                   195                 200                 205
Pro Asn Ser Thr Gly Ala Ala Lys Ala Ile Gly Leu Val Ile Pro Glu
210                 215                 220
Leu Asn Gly Lys Leu Asp Gly Ala Ala Gln Arg Val Pro Val Pro Thr
225                 230                 235                 240
Gly Ser Val Thr Glu Leu Val Ala Val Leu Asn Lys Glu Thr Ser Val
                   245                 250                 255
Glu Glu Ile Asn Ser Val Met Lys Ala Ala Ala Asn Asp Ser Tyr Gly
                   260                 265                 270
Tyr Thr Glu Asp Pro Ile Val Ser Ser Asp Ile Val Gly Met Ser Phe
                   275                 280                 285
Gly Ser Leu Phe Asp Ala Thr Gln Thr Lys Val Gln Thr Val Asp Gly
                   290                 295                 300
Asn Gln Leu Val Lys Val Val Ser Trp Tyr Asp Asn Glu Met Ser Tyr
305                 310                 315                 320
Thr Ala Gln Leu Asp Arg Thr Leu Glu Tyr Phe Ala Lys Ile Ala Lys
                   325                 330                 335

<210> SEQ ID NO 11
<211> LENGTH: 1011
<212> TYPE: DNA
<213> ORGANISM: Streptococcus iniae
<220> FEATURE:
<221> NAME/KEY: CDS
<222> LOCATION: (1)..(1011)

<400> SEQUENCE: 11 atg gta gtt aaa gtt ggt att aac ggt ttc gga cgt atc ggt cgt ctt      48
Met Val Val Lys Val Gly Ile Asn Gly Phe Gly Arg Ile Gly Arg Leu
 1               5                  10                  15 gca ttc cgt cgt att caa aat gtt gaa ggt gtt gaa gta act cgt atc      96
Ala Phe Arg Arg Ile Gln Asn Val Glu Gly Val Glu Val Thr Arg Ile
               20                  25                  30 aat gac ctt aca gat cct aac atg ctt gca cac ttg ttg aaa tat gat     144
Asn Asp Leu Thr Asp Pro Asn Met Leu Ala His Leu Leu Lys Tyr Asp
           35                  40                  45 aca act caa ggt cgt ttt gac ggt aca gtt gaa gtt aaa gat ggt gga     192
Thr Thr Gln Gly Arg Phe Asp Gly Thr Val Glu Val Lys Asp Gly Gly
       50                  55                  60 ttc gaa gtt aac gga agc ttt gtt aaa gtt tct gca gaa cgc gaa cca     240
Phe Glu Val Asn Gly Ser Phe Val Lys Val Ser Ala Glu Arg Glu Pro
65                  70                  75                  80 gca aac att gac tgg gct act gat ggt gta gac atc gtt ctt gaa gca     288
```

|   |   |   |   |   |   |   |   |   |   |   |   |   |   |   |   |     |
|---|---|---|---|---|---|---|---|---|---|---|---|---|---|---|---|-----|
|   |   | Ala | Asn | Ile | Asp | Trp | Ala | Thr | Asp | Gly | Val | Asp | Ile | Val | Leu | Glu | Ala |
|   |   |   |   |   | 85 |   |   |   | 90 |   |   |   | 95 |   |   |     |

```
aca ggt ttc ttc gct tct aaa gca gct gct gaa caa cac att cac gct     336
Thr Gly Phe Phe Ala Ser Lys Ala Ala Ala Glu Gln His Ile His Ala
            100             105             110 aac ggt gcg aaa aaa gtt gtt atc aca gct cct ggt gga aat gac gtt     384
Asn Gly Ala Lys Lys Val Val Ile Thr Ala Pro Gly Gly Asn Asp Val
        115             120             125 aaa aca gtt gtt tac aac act aac cat gat att ctt gat gga act gaa     432
Lys Thr Val Val Tyr Asn Thr Asn His Asp Ile Leu Asp Gly Thr Glu
130             135             140 aca gtt atc tca ggt gct tca tgt act aca aac tgt tta gct cca atg     480
Thr Val Ile Ser Gly Ala Ser Cys Thr Thr Asn Cys Leu Ala Pro Met
145             150             155             160 gct aaa gca tta caa gat aac ttt ggt gta aaa caa ggt tta atg act     528
Ala Lys Ala Leu Gln Asp Asn Phe Gly Val Lys Gln Gly Leu Met Thr
            165             170             175 act atc cat ggt tac act ggt gac caa atg gtt ctt gac gga cca cac     576
Thr Ile His Gly Tyr Thr Gly Asp Gln Met Val Leu Asp Gly Pro His
        180             185             190 cgt ggt ggt gat ctt cgt cgt gct cgt gca gct gca gca aac atc gtt     624
Arg Gly Gly Asp Leu Arg Arg Ala Arg Ala Ala Ala Asn Ile Val
    195             200             205 cct aac tca act ggt gct gct aaa gca atc ggt ctt gtt atc cca gaa     672
Pro Asn Ser Thr Gly Ala Ala Lys Ala Ile Gly Leu Val Ile Pro Glu
    210             215             220 tta aat ggt aaa ctt gac ggt gct gca caa cgt gtt cct gtt cca act     720
Leu Asn Gly Lys Leu Asp Gly Ala Ala Gln Arg Val Pro Val Pro Thr
225             230             235             240 gga tca gta act gaa tta gta gca gtt ctt gaa aaa gat act tca gta     768
Gly Ser Val Thr Glu Leu Val Ala Val Leu Glu Lys Asp Thr Ser Val
            245             250             255 gaa gaa atc aat gca gct atg aaa gca gca gct aac gat tca tac ggt     816
Glu Glu Ile Asn Ala Ala Met Lys Ala Ala Ala Asn Asp Ser Tyr Gly
            260             265             270 tac act gaa gat gct atc gta tca tca gat atc gta ggt att tct tac     864
Tyr Thr Glu Asp Ala Ile Val Ser Ser Asp Ile Val Gly Ile Ser Tyr
        275             280             285 ggt tca tta ttt gat gct act caa act aaa gta caa act gtt gat gga     912
Gly Ser Leu Phe Asp Ala Thr Gln Thr Lys Val Gln Thr Val Asp Gly
290             295             300 aat caa ttg gtt aaa gtt gtt tca tgg tat gac aat gaa atg tct tac     960
Asn Gln Leu Val Lys Val Val Ser Trp Tyr Asp Asn Glu Met Ser Tyr
305             310             315             320 act gct caa ctt gtt cgt act ctt gag tac ttt gca aaa atc gct aaa    1008
Thr Ala Gln Leu Val Arg Thr Leu Glu Tyr Phe Ala Lys Ile Ala Lys
            325             330             335 taa                                                                1011

<210> SEQ ID NO 12
<211> LENGTH: 336
<212> TYPE: PRT
<213> ORGANISM: Streptococcus iniae

<400> SEQUENCE: 12

Met Val Val Lys Val Gly Ile Asn Gly Phe Gly Arg Ile Gly Arg Leu
 1               5                  10                  15

Ala Phe Arg Arg Ile Gln Asn Val Glu Gly Val Glu Val Thr Arg Ile
            20                  25                  30
```

-continued

```
Asn Asp Leu Thr Asp Pro Asn Met Leu Ala His Leu Leu Lys Tyr Asp
         35                  40                  45

Thr Thr Gln Gly Arg Phe Asp Gly Thr Val Glu Val Lys Asp Gly Gly
         50                  55                  60

Phe Glu Val Asn Gly Ser Phe Val Lys Val Ser Ala Glu Arg Glu Pro
 65                  70                  75                  80

Ala Asn Ile Asp Trp Ala Thr Asp Gly Val Asp Ile Val Leu Glu Ala
                 85                  90                  95

Thr Gly Phe Phe Ala Ser Lys Ala Ala Ala Glu Gln His Ile His Ala
                100                 105                 110

Asn Gly Ala Lys Lys Val Val Ile Thr Ala Pro Gly Gly Asn Asp Val
            115                 120                 125

Lys Thr Val Val Tyr Asn Thr Asn His Asp Ile Leu Asp Gly Thr Glu
130                 135                 140

Thr Val Ile Ser Gly Ala Ser Cys Thr Thr Asn Cys Leu Ala Pro Met
145                 150                 155                 160

Ala Lys Ala Leu Gln Asp Asn Phe Gly Val Lys Gln Gly Leu Met Thr
                165                 170                 175

Thr Ile His Gly Tyr Thr Gly Asp Gln Met Val Leu Asp Gly Pro His
            180                 185                 190

Arg Gly Gly Asp Leu Arg Arg Ala Arg Ala Ala Ala Ala Asn Ile Val
            195                 200                 205

Pro Asn Ser Thr Gly Ala Ala Lys Ala Ile Gly Leu Val Ile Pro Glu
        210                 215                 220

Leu Asn Gly Lys Leu Asp Gly Ala Ala Gln Arg Val Pro Val Pro Thr
225                 230                 235                 240

Gly Ser Val Thr Glu Leu Val Ala Val Leu Glu Lys Asp Thr Ser Val
                245                 250                 255

Glu Glu Ile Asn Ala Ala Met Lys Ala Ala Asn Asp Ser Tyr Gly
            260                 265                 270

Tyr Thr Glu Asp Ala Ile Val Ser Ser Asp Ile Val Gly Ile Ser Tyr
        275                 280                 285

Gly Ser Leu Phe Asp Ala Thr Gln Thr Lys Val Gln Thr Val Asp Gly
    290                 295                 300

Asn Gln Leu Val Lys Val Val Ser Trp Tyr Asp Asn Glu Met Ser Tyr
305                 310                 315                 320

Thr Ala Gln Leu Val Arg Thr Leu Glu Tyr Phe Ala Lys Ile Ala Lys
                325                 330                 335
```